(12) United States Patent
Fetissov et al.

(10) Patent No.: US 10,729,770 B2
(45) Date of Patent: Aug. 4, 2020

(54) BACTERIAL INFLUENCE ON REGULATION OF APPETITE VIA CLPB PROTEIN MIMICRY OF ALPHA-MSH

(71) Applicants: Institut National de la Sante et de la Recherche Medicale (INSERM), Paris (FR); Centre Hospitalier Universitaire de Rouen, Rouen (FR); Universite de Rouen, Mont-Saint Aignan (FR); TARGEDYS, Rouen (FR)

(72) Inventors: Serguei Fetissov, Rouen (FR); Emmanuelle De, Mont-Saint-Aignan (FR); Naouel Tennoune, Beauvais (FR); Jonathan Breton, Rouen (FR); Philippe Chan-Tchi-Song, Rouen (FR); Pierre Dechelotte, Rouen (FR); Romain Legrand, Rouen (FR); Gregory Lambert, Châtenay-Malabry (FR)

(73) Assignees: INSTITUT NATIONAL DE LA SANTE ET DE LA RECHERCHE MEDICALE (INSERM), Paris (FR); CENTRE HOSPITALIER UNIVERSITAIRE DE ROUEN, Rouen (FR); UNIVERSITE DE ROUEN, Mont-Saint-Aignan (FR); TARGEDYS, Rouen (FR)

( * ) Notice: Subject to any disclaimer, the term of this patent is extended or adjusted under 35 U.S.C. 154(b) by 0 days.

(21) Appl. No.: 16/032,604

(22) Filed: Jul. 11, 2018

(65) Prior Publication Data
US 2018/0369378 A1 Dec. 27, 2018

Related U.S. Application Data

(63) Continuation-in-part of application No. 15/101,452, filed as application No. PCT/EP2014/007661 on Dec. 4, 2014, now abandoned.

(30) Foreign Application Priority Data

Dec. 5, 2013 (EP) .................................. 13306673
Oct. 2, 2014 (EP) .................................. 14306552

(51) Int. Cl.
*A61K 39/40* (2006.01)
*A61P 1/14* (2006.01)
(Continued)

(52) U.S. Cl.
CPC ............... *A61K 39/40* (2013.01); *A61P 1/14* (2018.01); *C07K 14/245* (2013.01);
(Continued)

(58) Field of Classification Search
CPC ............ A61K 39/40; A61K 2039/545; A61K 2039/55516; A61P 1/14; C07K 2317/76;
(Continued)

(56) References Cited

U.S. PATENT DOCUMENTS 6,716,810 B1 4/2004 Brennan
2011/0206641 A1 8/2011 Berger
(Continued)

FOREIGN PATENT DOCUMENTS

WO 2007085970 8/2007
WO WO-2015082655 A1 * 6/2015 ......... A61K 39/0258

OTHER PUBLICATIONS

Tennoune et al., (Nature. Transl Psychiatry (2014) 4, e458) (Year: 2014).*
(Continued)

*Primary Examiner* — Jana A Hines
(74) *Attorney, Agent, or Firm* — W&C IP

(57) ABSTRACT

The present invention relates to ClpB expressing bacteria and their impact on obesity. The present invention relates to bacterial ClpB protein and ClpB expressing bacteria and
(Continued)

Figure 2A:
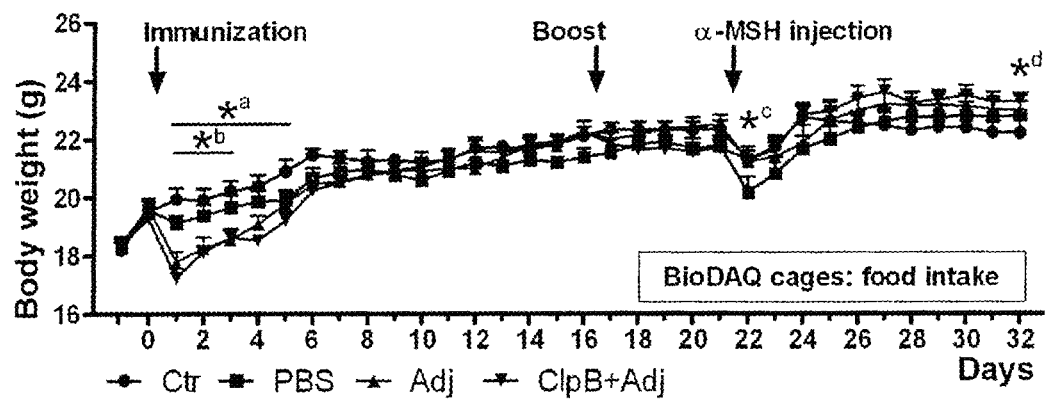

their impact on eating disorders. The invention further relates to compositions comprising antibiotic directed against at least one ClpB expressing bacterium as well as probiotics not expressing ClpB protein and their use in the treatment or prevention of eating disorders. The invention also relates to diagnostic tools for determining whether a subject is likely to respond to a method of treating eating disorders and to methods of immunization against eating disorders.

12 Claims, 17 Drawing Sheets

Specification includes a Sequence Listing.

(51) Int. Cl.
  C07K 14/245 (2006.01)
  C07K 16/12 (2006.01)
  C07K 16/26 (2006.01)
  A61K 39/00 (2006.01)

(52) U.S. Cl.
  CPC .......... C07K 16/1232 (2013.01); C07K 16/26 (2013.01); A61K 2039/545 (2013.01); A61K 2039/55516 (2013.01); C07K 2317/33 (2013.01); C07K 2317/34 (2013.01); C07K 2317/76 (2013.01)

(58) Field of Classification Search
  CPC .............. C07K 16/1232; C07K 16/26; C07K 2317/33; C07K 2317/34; C07K 14/245
  See application file for complete search history.

(56) References Cited

U.S. PATENT DOCUMENTS

2017/0252399 A1  9/2017 Fetissov
2018/0153959 A1  6/2018 Fetissov

OTHER PUBLICATIONS

Didinen et al., (Iranian J of Fisheries Sciences 15(4):1307-1317. Oct. 2016) (Year: 2016).*
Padilla et al., (J of Applied Animal Res. 2015. vol. 2015, Issue 2. entitled The Pathogen Hafnia alvei in Veterinary Medicine: A Review.) (Year: 2015).*
Gunthard et al., (Clin Infect Dis. Jun. 22, 1996(6):1040-5. (Year: 1996).*
Fetissov et al., "Autoantibodies against appetite-regulating peptide hormones and neuropeptides: putative modulation by gut microflora". Nutrition. Apr. 2008;24(4):348-59.
Broadbent, J. et al. "attributes of the heat shock response in three species of dairy lactobacillus" System. Appl. Microbiol. 1997; 20; 12-19.
Xu et al., "Brain-derived neurotrophic factor regulates energy balance downstream of melanocortin-4 receptor". Nat Neurosci. Jul. 2003;6(7):736-42.
Vijay-Kumar et al., "Metabolic syndrome and altered gut microbiota in mice lacking toll-like receptor 5". Science. Apr. 9, 2010;328(5975):228-31.
Parks et al., "Genetic control of obesity and gut microbiota composition in response to high-fat, high-sucrose diet in mice". Cell Metab. Jan. 8, 2013;17(1):141-52.
Power & Schulkin,"Anticipatory physiological regulation in feeding biology: Cephalic phase responses". Appetite. Mar.-May 2008;50(2-3):194-206.
Johnstone et al., "Neuronal activation in the hypothalamus and brainstem during feeding in rats". Cell Metab. Oct. 2006;4(4):313-21.
Haange et al., "Metaproteome analysis and molecular genetics of rat intestinal microbiota reveals section and localization resolved species distribution and enzymatic functionalities". J Proteome Res. Nov. 2, 2012;11(11):5406-17.
Halaas et al., "Weight-reducing effects of the plasma protein encoded by the obese gene". Science. Jul. 28, 1995;269 (5223):543-6.
Glasgow et al., "Rat gastroduodenal motility in vivo: involvement of NO and ATP in spontaneous motor activity". Am J Physiol. Nov. 1998;275(5 Pt 1):G889-96.
Forsythe & Kunze, "Voices from within: gut microbes and the CNS". Cell Mol Life Sci. Jan. 2013;70(1):55-69.
Foucault et al., "In vivo bioluminescence imaging for the study of intestinal colonization by *Escherichia coli* in mice". Appl Environ Microbiol. Jan. 2010;76(1):264-74.
Fetissov & Déchelotte, "The new link between gut-brain axis and neuropsychiatric disorders". Curr Opin Clin Nutr Metab Care. Sep. 2011;14(5):477-82.

* cited by examiner

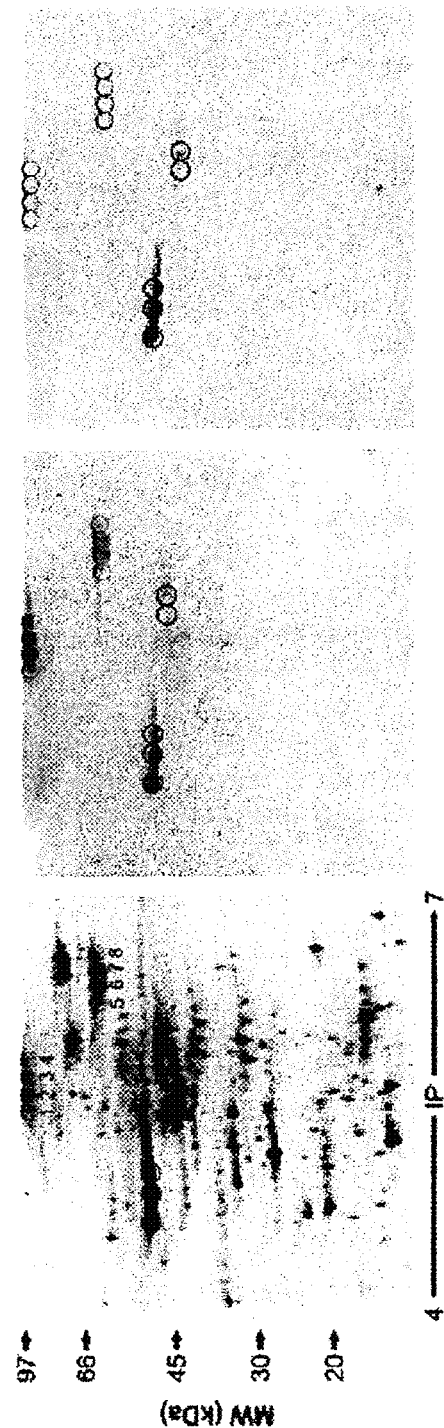
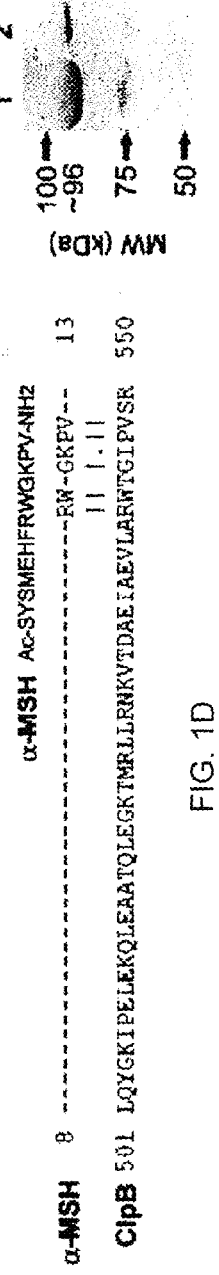
FIG. 1A  FIG. 1B  FIG. 1C
α-MSH     Ac-SYSMEHFRWGKPV-NH2
          ---------RW-GKPV---        13
                   ||·||              
ClpB 501  LQYGKIPELEKQLEAATQLEGKTMRLLRNKVTDAEIAEVLARWTGIPVSR   550
FIG. 1D
FIG. 1E □ before adsorption
■ adsorption with α-MSH $10^{-6}$M

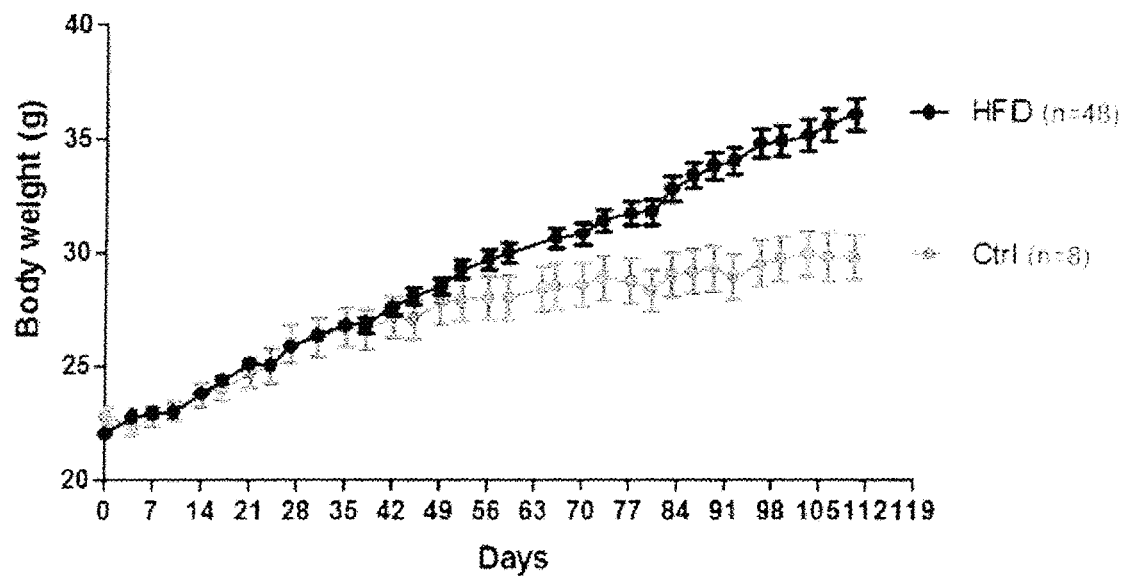
FIG. 18A
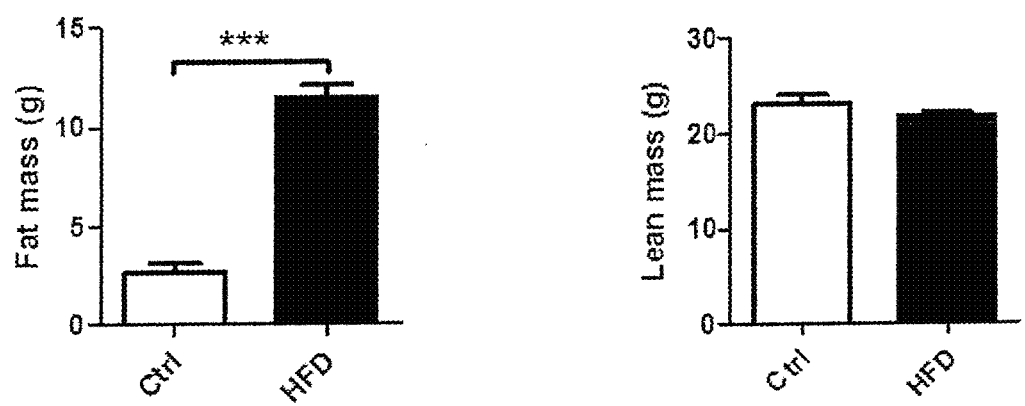
FIG. 18B
FIG. 18C

BACTERIAL INFLUENCE ON REGULATION OF APPETITE VIA CLPB PROTEIN MIMICRY OF ALPHA-MSH

CROSS-REFERENCE TO RELATED APPLICATIONS

This application is a continuation-in-part (CIP) application of USSN Ser. No. 15/101,452 filed Jun. 3, 2016, which itselfwas a Rule 371 filing from international application PCT/EP2014/007661 filed Dec. 4, 2014, which claimed priority to European Application 14306552.2 filed Oct. 2, 2014 and European Application 13306673.8 filed Dec. 5, 2013.

The present invention relates to bacterial ClpB protein and ClpB expressing bacteria and their impact on eating disorders. The invention further relates to compositions comprising antibiotic directed against at least one ClpB expressing bacterium as well as probiotics not expressing ClpB protein and their use in the treatment or prevention of eating disorders. The invention also relates to diagnostic tools for determining whether a subject is likely to respond to a method of treating eating disorders and to methods of immunization against eating disorders.

Eating disorders increased all over the world among both men and women over the last 50 years. There is evidence to suggest that in particular individuals in the western world are at the highest risk of developing them and the degree of westernization increases the risk. With recent advances, the scientists understand more and more the central processes of appetite. It is known that interactions between motivational, homeostatic and self-regulatory control processes are involved in eating behavior, which is a key component in eating disorders.

Recent science discovered a further regulator, the human microbiome. Advances of high-throughput DNA sequencing technologies allowed to explore the human microbiome and thus to make a major step towards the understanding of the molecular relationships between the host and its microbiota. This "second genome", the microbiome, has been described in a catalogue of more than 4-5 million, non-redundant microbial putative genes and 1 to 2,000 prevalent bacterial species. Each individual has at least 160 shared species and a number of well-balanced host-microbial molecular relationships that defines groups of individuals.

It is considered that understanding the essential features of symbiotic relationships between microbial communities and their human host may allow to predict host phenotypes, such as health status, from the particular features of indigenous communities.

The composition of gut microbiota for example has been associated with host metabolic phenotypes including obesity and diabetes as well as some neuropsychiatric disorders suggesting that gut bacteria may influence brain controlled functions and behavior.

In this context, determining the molecular mechanisms linking the microbiota to the host behavior appears, thus, as a necessary step for defining the role of specific microorganisms in host physiology.

The molecular mechanisms at the origin of eating disorders, including anorexia nervosa (AN), bulimia (BN), and binge-eating disorder (BED), are currently unknown. Previous data indicated that immunoglobulins (Igs) or autoantibodies (auto-Abs) reactive with α-melanocyte-stimulating hormone (α-MSH) are involved in regulation of feeding and emotion; however, the origin of such auto-Abs is unknown.

The inventors discovered, using proteomics, that the ClpB chaperon protein of commensal gut bacteria E. Coli K12 is a conformational mimetic of α-melanocyte-stimulating hormone (α-MSH), a neuropeptide involved in the regulation of energy metabolism and emotion.

The inventors show that ClpB-immunized mice produce anti-ClpB IgG crossreactive with α-MSH, influencing food intake, body weight, anxiety and melanocortin receptor 4 signaling. Furthermore, they show that chronic intragastric delivery of E. coli in mice decreased food intake and stimulated formation of ClpB- and α-MSH-reactive antibodies, while ClpB-deficient E. coli did not affect food intake or antibody levels. Finally, they show that plasma levels of anti-ClpB IgG crossreactive with α-MSH are increased in patients with AN, BN and BED, and that the ED (eating disorders) Inventory-2 scores in eating disorders patients correlate with anti-ClpB IgG and IgM.

As a consequence, they show that the bacterial ClpB protein, which is present in several commensal and pathogenic microorganisms, can be responsible for the production of auto-Abs crossreactive with α-MSH, associated with altered feeding and emotion in humans with eating disorders.

In addition, they show increased plasma concentrations of the ClpB protein in patients suffering from eating disorders.

Therefore, the presence of ClpB protein and/or anti-ClpB antibodies can be related to eating disorders and to a dysregulation of appetite and emotion.

The presence of the ClpB protein and/or anti-ClpB antibodies been correlated with eating disorders and dysregulation of appetite, in return reducing the level of ClpB protein and/or anti-ClpB antibodies can result in regulation of appetite and thus be used as a treatment of eating disorders.

Accordingly, the present invention relates to a composition comprising at least one antibiotic directed against at least one ClpB expressing bacterium for use in the treatment or prevention of eating disorders.

The present invention further relates to a non-therapeutic method of regulating appetite in a subject, comprising administering to said subject an effective amount of a composition comprising at least one antibiotic directed against at least one ClpB expressing bacterium.

Accordingly, the present invention also relates to a composition comprising probiotics not expressing ClpB for use in the treatment or prevention of an eating disorder.

The present invention further relates to a non-therapeutic method of regulating appetite in a subject, comprising administering to said subject an effective amount of a composition comprising probiotics not expressing ClpB.

The present invention also relates to a composition comprising a ClpB protein for use as a vaccine or as an immunogenic composition.

In particular, said composition for use, is used in the immunization against eating disorders.

In particular, said composition for use, is used for preventing eating disorders.

The invention also concerns an in vitro method for diagnosing an eating disorder in a subject, which method comprises:
a) measuring the level of ClpB protein and/or anti-ClpB antibodies in a biological sample from said subject;
b) comparing said measured level of ClpB protein and/or anti-ClpB antibodies to a reference value; and
c) deducing therefrom if the subject suffers from an eating disorder.

The present invention further relates to an in vitro method of selecting subjects suffering from an eating disorder as likely to respond to a treatment reducing the level of ClpB protein and/or anti-ClpB antibodies which comprises:
a) measuring the level of ClpB protein and/or anti-ClpB antibodies in a biological sample from said subject;
b) comparing said measured level of ClpB protein and/or anti-ClpB antibodies to a reference value; and
c) selecting the subject for a treatment reducing the level of ClpB protein and/or anti-ClpB antibodies, wherein said treatment reducing the level of ClpB protein and/or anti-ClpB antibodies comprises administering to said subject an effective amount of a composition comprising one antibiotic directed against at least one ClpB expressing bacterium and/or administering to said subject an effective amount of a composition comprising probiotics not expressing ClpB and/or a combination thereof.

The inventors having showed that intragastric delivery of E. coli in mice decreased food intake and body weight gain due to the presence of ClpB protein in bacteria, the invention further relates to a composition comprising probiotics expressing or surexpressing ClpB protein for use in the treatment or prevention of obesity.

DETAILED DESCRIPTION OF THE INVENTION

The inventors discovered, using proteomics, that the ClpB chaperon protein of commensal gut bacteria E.Coli K12 is a conformational mimetic of α-melanocyte-stimulating hormone (α-MSH), a neuropeptide involved in the regulation of energy metabolism and emotion and that the presence of ClpB expressing bacteria results in dysregulated appetite.

Accordingly, the present invention refers to a composition comprising at least one antibiotic directed against at least one ClpB expressing bacterium for use in the treatment or prevention of eating disorders.

As used herein, "ClpB expressing bacterium" refers to bacteria expressing the chaperone protein ClpB.

The "protein disaggregation chaperone", "chaperone protein ClpB", "ClpB protein" or "ClpB" also known as heat shock protein F84.1 is a member of the Hsp100/ClpB family of hexameric AAA+-ATPases. This family comprises bacterial, fungal, and plant Hsp100 ATPases, ClpB being the bacterial representative. As a part of a stress-induced multichaperone system, it is involved in the recovery of the cell from heat-induced damage, in cooperation with the Hsp70 system (DnaK, DnaJ and GrpE) in protein disaggregation, a crucial process for cell survival under stress conditions.

During the infection process, bacterial pathogens encounter stress conditions generated by the host defense to eliminate them and respond to this host defense by increasing the synthesis of heat shock and other stress proteins. In this context, ClpB has been described as an essential factor for acquired thermotolerance and for the virulence and infectivity of several Gram-negative and Gram-positive pathogenic bacteria, such as *Staphylococcus aureus, Francisella turalensis, Listeria monocytogenes, Yersinia enterocolitica,* and *Salmonella thyphimurium.*

In *E. coli* K12 the chaperone protein ClpB also known as heat shock protein F84.1 or htpM and is a protein of 857 amino acids.

Typically, the chaperone protein ClpB comprises or consists of the amino acid sequence of the chaperone protein ClpB from *E. Coli* K12 with SEQ ID NO: 1 (NCBI Reference Number: NP_417083.1, as available on Nov. 6, 2013 and/or UniProtKB/Swiss-Prot Number: P63284, as available on Nov. 6, 2013). Preferably, the amino acid sequence of chaperone protein ClpB comprises or consists of an amino acid sequence 80 to 100% identical to the amino acid sequence of SEQ ID NO: 1. Preferably, the amino acid sequence is 90 to 100% identical, more preferably 95 to 100%, most preferably 95, 96, 97, 98, 99 or 100% identical to the amino acid sequence of SEQ ID NO: 1.

Thus, a ClpB expressing bacterium refers to a bacterium expressing or over-expressing the chaperone protein ClpB as defined above or a polypeptide comprising or consisting of an amino acid sequence 80 to 100% identical to the amino acid sequence of SEQ ID NO: 1, more preferably 95 to 100%, most preferably 95, 96, 97, 98, 99 or 100% identical to the amino acid sequence of SEQ ID NO: 1.

By a polypeptide having an amino acid sequence at least, for example, 95% "identical" to a query amino acid sequence of the present invention, it is intended that the amino acid sequence of the subject polypeptide is identical to the query sequence except that the subject polypeptide sequence may include up to five amino acid alterations per each 100 amino acids of the query amino acid sequence. In other words, to obtain a polypeptide having an amino acid sequence at least 95% identical to a query amino acid sequence, up to 5% (5 of 100) of the amino acid residues in the subject sequence may be inserted, deleted, or substituted with another amino acid.

In the context of the present application, the percentage of identity is calculated using a global alignment (i.e. the two sequences are compared over their entire length). Methods for comparing the identity of two or more sequences are well known in the art. The «needle» program, which uses the Needleman-Wunsch global alignment algorithm (Needleman and Wunsch, 1970 J. Mol. Biol. 48:443-453) to find the optimum alignment (including gaps) of two sequences when considering their entire length, may for example be used. The needle program is, for example, available on the ebi.ac.uk world wide web site. The percentage of identity in accordance with the invention is preferably calculated using the EMBOSS: needle (global) program with a "Gap Open" parameter equal to 10.0, a "Gap Extend" parameter equal to 0.5, and a Blosum62 matrix.

Proteins consisting of an amino acid sequence "at least 80%, 85%, 90%, 95%, 96%, 97%, 98% or 99% identical" to a reference sequence may comprise mutations such as deletions, insertions and/or substitutions compared to the reference sequence. In case of substitutions, the protein consisting of an amino acid sequence at least 80%, 85%, 90%, 95%, 96%, 97%, 98% or 99% identical to a reference sequence may correspond to a homologous sequence derived from another species than the reference sequence.

Amino acid substitutions may be conservative or non-conservative. Preferably, substitutions are conservative substitutions, in which one amino acid is substituted for another amino acid with similar structural and/or chemical properties. The substitution preferably corresponds to a conservative substitution as indicated in the table below.

| Conservative substitutions | Type of Amino Acid |
|---|---|
| Ala, Val, Leu, Ile, Met, Pro, Phe, Trp | Amino acids with aliphatic hydrophobic side chains |
| Ser, Tyr, Asn, Gln, Cys | Amino acids with uncharged but polar side chains |
| Asp, Glu | Amino acids with acidic side chains |
| Lys, Arg, His | Amino acids with basic side chains |
| Gly | Neutral side chain |

ClpB expressing bacteria are well-known from the skilled person and may be identified by any conventional technique such as by bacterial stress-induction or genetic engineering.

In some embodiments, the bacterial strain, in particular the probiotic bacterial strain, is a gram-negative strain.

In one embodiment, the bacterial strain, in particular the probiotic bacterial strain, is a non-pathogenic gram-negative strain.

In one embodiment, the ClpB expressing bacterium is selected from the group constituted of the genus *Staphylococcus aureus, Francisella turalensis, Listeria monocytogenes, Yersinia enterocolitica, Salmonella thyphimurium, Escherichia Coli*, Enterobacteriaceae, *Shigella sonnei, Shigella flexneri, Shigella dysenteriae, Shigella Citrobacter youngae, Salmonella bongori* and *Salmonella enterica*.

In one embodiment, the ClpB expressing bacterium is selected from the group constituted of the taxa *Staphylococcus aureus, Francisella turalensis, Listeria monocytogenes, Yersinia enterocolitica, Salmonella thyphimurium, Escherichia Coli*, Enterobacteriaceae, *Citrobacter youngae, Salmonella bongori* and *Salmonella enterica*.

In some embodiments, the bacterial strain, in particular the probiotic bacterial strain, is a member of the family of Enterobacteriaceae.

In particular, the bacterial strain is a non-pathogenic member of the family of Enterobacteriaceae. In one embodiment, the ClpB expressing bacterium is selected from the group constituted of the genera *Escherichia Coli, Citrobacter youngae, Proteus, Klebsiella, Hafnia, Providencia* and *Enterobacter*.

In one embodiment, the ClpB expressing bacterium is selected from the group constituted of the genera *Escherichia, Proteus* and *Hafnia*.

In some embodiments, the bacterial strain, in particular the probiotic bacterial strain, is an *E. coli* strain. In some embodiments, *E. coli* strains, in particular probiotic *E. coli* strains, for use according to the teachings of present invention include non-pathogenic *E. coli* strains which exert probiotic activity. Example of probiotic *E. coli* strain is the probiotic *Escherichia coli* strain BU-230-98, ATCC Deposit No. 202226 (DSM 12799), which is an isolate of the known, commercially available, probiotic *Escherichia coli* strain M-17. Example of a non-pathogenic *E. coli* strain is *E. coli* Nissle 1917. An example of *E. coli* strain which was not known as probiotic is the laboratory *E. coli* strain K12.

In other embodiments, the bacterial strain is a *Hafnia alvei* strain, such as the *Hafnia alvei* strain AF036 commercialized by Bioprox Company. In still other embodiments, the bacterial strain is a *Proteus vulgaris* strain.

In still other embodiments, a combination of bacterial strains expressing or overexpressing the ClpB protein or variant thereof is used.

The ClpB protein comprises two nucleotide binding domains (ATP1 and ATP2) and two oligomerization domains (NBD1 and NBD2). The N-terminal domain might function as a substrate-discriminating domain, recruiting aggregated proteins to the ClpB hexamer and/or stabilizing bound proteins. The NBD2 domain is responsible for oligomerization, whereas the NBD1 domain stabilizes the hexamer probably in an ATP-dependent manner. The movement of the coiled-coil domain is essential for ClpB ability to rescue proteins from an aggregated state, probably by pulling apart large aggregated proteins, which are bound between the coiled-coils motifs of adjacent ClpB subunits in the functional hexamer.

The inventors identified that the ClpB chaperon protein of commensal gut bacteria *E. coli* K12 is a conformational mimetic of α-melanocyte-stimulating hormone (α-MSH), a neuropeptide involved in the regulation of energy metabolism and emotion.

"α-MSH", also known as "α-Melanocyte-stimulating hormone", "alpha-MSH", "α-MSH", alpha-melanotropin, alpha-melanocortin, or alpha-intermedin, is a naturally occurring endogenous peptide hormone of the melanocortin family, with a tridecapeptide structure. The amino acid sequence of α-MSH preferably comprises or consists of the amino acid sequence SYSMEHFRWGKPV (SEQ ID NO: 3) (Gen Pept Sequence ID, PRF: 223274, as available on Dec. 2, 2013). However, there exist three types of alpha-melanocyte-stimulating hormone that differ in their acetyl status, the desacetyl alpha MSH, which lacks an acetyl group; mono-acetyl alpha MSH, in which the amino group of the Ser-1 of SEQ ID NO: 3 is acetylated; and di-acetyl alpha MSH, in which both amino and hydroxy groups of the Ser-1 of SEQ ID NO: 3 are acetylated. α-MSH as used herein refers in particular to the mono-acetylated α-MSH.

It is critically involved in the regulation of energy balance and increasing energy expenditure via activation of the melanocortin receptors type 4 (MC4R), acting both centrally and peripherally. In both humans and mice, plasma α-MSH levels are associated with body weight changes. Furthermore, α-MSH regulates mood and emotion by increasing anxiety.

"Mimetic" refers to a protein that imitates another protein. This imitation is possible since the protein shares certain characteristics with the protein it mimetics.

A "conformational mimetic" refers to a protein, that shares at least in part the same conformation as another protein.

The inventors demonstrated that the ClpB protein shares a discontinuous sequence homology between amino acids 542 to 548 from SEQ ID NO: 1 with α-MSH, of amino acid sequence 'RWTGIPV' (referenced under SEQ ID NO: 2). Without being bound by theory, this conformation of ClpB allows stimulating the production of antibodies directed against both ClpB and α-MSH.

Thus "conformational mimetic" herein preferably refers to the capability to stimulate antibody production against ClpB as well as auto antibodies against α-MSH.

An "antibiotic directed against at least one ClpB expressing bacterium" refers herein to an antimicrobial compound that inhibits the growth of ClpB expressing bacteria and/or reduces the amount of ClpB expressing bacteria and/or destroys ClpB expressing bacteria.

The antibiotic directed against at least one ClpB expressing bacterium, preferably inhibits the growth, reduces the amount and/or destroys selectively or preferentially ClpB expressing bacteria. Said antibiotic preferably does not negatively affect eukaryotic cells.

Antibiotics targeting specifically ClpB expressing cells are well known from the skilled person and are further described in Martin, I et al. (Journal of Medicinal Chemistry, 2013, 56: 7177-7189).

The antibiotic directed against at least one ClpB expressing bacterium may bind to ClpB and modulate its activity.

In particular, the antibiotic directed against at least one ClpB expressing bacterium modulates
  i) the ATPase activity of ClpB, and/or
  ii) inhibit the free/and or substrate bond form of ClpB and/or
  iii) inhibit the activation of ClpB.

In one embodiment, the antibiotic directed against at least one ClpB expressing bacterium is a salicylaldehyde derivative over a benzylbenzene scaffold, in particular, 5-(2- chlorobenzyl)-2-hydroxy-3-nitrobenzaldehyde (CAS Number 292644-32-7, Sigma Aldrich) or (2-{[(3,4-dichlorophenyl)amino]thioxomethylthio}ethoxy)-N-benzamide (Supplier Number ST034398, TimTec).

A typical dose for an antibiotic directed against at least one ClpB expressing bacterium of the present invention can be, for example, in the range of from about 0.01 mg/kg to about 30 mg/kg; however, doses below or above this exemplary range are envisioned, especially considering the aforementioned factors. The daily oral dosage regimen may be about 0.01 mg/kg to about 30 mg/kg of total body weight, in particular 0.01, 0.1, 0.2, 0.3, 0.4, 0.5, 0.6, 0.7, 0.8, 0.9, 1, 2, 3, 4, 5, 6, 7, 8, 9, 10, 12, 14, 16, 18, 20, 22, 24, 26, 28, 30 mg/kg body weight. Patient progress can be monitored by periodic assessment, and the dose adjusted accordingly.

In the context of the invention, the term "treating" or "treatment", as used herein, means reversing, alleviating, inhibiting the progress of the disorder to which such term applies, or one or more symptoms of such disorder or condition.

"Preventing" refers to measures taken to prevent the disorder to which such term applies from occurrence or, in early stages of a disorder. Preventing further refers to the inhibition of further development of a disorder to which such term applies.

Treatment or prevention of eating disorders preferably refers herein to the reduction of the amount or concentration of ClpB expressing bacteria in the subject to be treated.

In the context of the present invention, a "subject" denotes a human or non-human mammal, such as a rodent (rat, mouse, rabbit), a primate (chimpanzee), a feline (cat), or a canine (dog). Preferably, the subject is human. The subject according to the invention may be in particular a male or a female.

In some embodiments, the subject is an adult (for example, a human subject above the age of 18). In another embodiment, the subject is a child (for example, a human subject below the age of 18). In some embodiments, the subject may be a "patient", i.e. a subject who/which is awaiting the receipt of, or is receiving medical care or was/is/will be the object of a medical procedure according to the methods of the present invention, or is monitored for the development of a disease.

In some embodiments, the subject has a body mass index of between 18.5 and 30.

In the context of this invention, subject is obese and has a BMI superior to 30.

In some embodiments, the subject is moderately obese. A "moderately obese" subject refers to a subject having a BMI of between 30 and 35.

Preferably, the subject according to the invention is older than 13.

Preferably, the subject is a female.

By "eating disorder" (ED) is meant psychiatric illnesses defined by criteria from the Diagnostic and Statistical Manual of Mental Disorders 5th Edition (DSM-5) and earlier editions (DSM-4, etc). Abnormal eating habits may involve either insufficient or excessive food intake to the detriment of an individual's physical and mental health. Bulimia nervosa (BN), anorexia nervosa (AN) and binge eating disorder (BED) are the most common specific forms of eating disorders. According to the DSM-5 criteria, to be diagnosed as having anorexia nervosa a person must display: persistent restriction of energy intake leading to significantly low body weight (in context of what is minimally expected for age, sex, developmental trajectory, and physical health), either an intense fear of gaining weight or of becoming fat, or persistent behavior that interferes with weight gain (even though significantly low weight), disturbance in the way one's body weight or shape is experienced, undue influence of body shape and weight on self-evaluation, or persistent lack of recognition of the seriousness of the current low body weight.

According to the DSM-5 criteria, to be diagnosed as having bulimia nervosa a person must display recurrent episodes of binge eating. An episode of binge eating is characterized by both of the following: eating, in a discrete period of time (e.g. within any 2-hour period), an amount of food that is definitely larger than most people would eat during a similar period of time and under similar circumstances and a sense of lack of control over eating during the episode (e.g. a feeling that one cannot stop eating or control what or how much one is eating), recurrent inappropriate compensatory behavior in order to prevent weight gain, such as self-induced vomiting, misuse of laxatives, diuretics, or other medications, fasting, or excessive exercise. The binge eating and inappropriate compensatory behaviors both occur, on average, at least once a week for three months. Self-evaluation is unduly influenced by body shape and weight.

According to the DSM-5 criteria, to be diagnosed as having binge eating disorder a person must display recurrent episodes of binge eating. An episode of binge eating is characterized by both of the following: eating, in a discrete period of time (e.g. within any 2-hour period), an amount of food that is definitely larger than most people would eat during a similar period of time and under similar circumstances, a sense of lack of control over eating during the episode (e.g. a feeling that one cannot stop eating or control what or how much one is eating). The binge eating episodes are associated with three or more of the following:
  eating much more rapidly than normal;
  eating until feeling uncomfortably full;
  eating large amounts of food when not feeling physically hungry;
  eating alone because of feeling embarrassed by how much one is eating;
  feeling disgusted with oneself, depressed or very guilty afterward.

Binge eating occurs, on average, at least once a week for three months.

Other types of eating disorders include Other Specified Feeding or Eating Disorder (OSFED).

According to the DSM-5 criteria, to be diagnosed as having OSFED a person must present with a feeding or eating behaviors that cause clinically significant distress and impairment in areas of functioning, but do not meet the full criteria for any of the other feeding and eating disorders. A diagnosis might then be allocated that specifies a specific reason why the presentation does not meet the specifics of another disorder (e.g. bulimia nervosa-low frequency). The following are further examples for OSFED:
  Atypical anorexia nervosa: all criteria are met, except despite significant weight loss, the individual's weight is within or above the normal range;
  Binge eating disorder (of low frequency and/or limited duration): all of the criteria for BED are met, except at a lower frequency and/or for less than three months;
  Bulimia nervosa (of low frequency and/or limited duration): all of the criteria for bulimia nervosa are met, except that the binge eating and inappropriate compensatory behavior occurs at a lower frequency and/or for less than three months;

Purging disorder: recurrent purging behavior to influence weight or shape in the absence of binge eating;

Night eating syndrome: recurrent episodes of night eating, eating after awakening from sleep, or by excessive food consumption after the evening meal. The behavior is not better explained by environmental influences or social norms. The behavior causes significant distress/impairment. The behavior is not better explained by another mental health disorder (e.g. BED); Unspecified Feeding or Eating Disorder (UFED). According to the DSM-5 criteria this category applies to where behaviors cause clinically significant distress/impairment of functioning, but do not meet the full criteria of any of the Feeding or Eating Disorder criteria. This category may be used by clinicians where a clinician chooses not to specify why criteria are not met, including presentations where there may be insufficient information to make a more specific diagnosis (e.g. in emergency room settings).

In the context of the present invention, an eating disorder can thus refer to the above mentioned list of disorders.

In one embodiment, the eating disorder is selected from the group consisting of anorexia nervosa (AN), bulimia nervosa (BN), binge eating disorder (BED), overeating, hyperphagia, wasting diseases such as cachexia By "appetite" is meant the desire to eat food, felt as hunger. Appetite exists in all higher life-forms, and serves to regulate adequate energy intake to maintain metabolic needs. It is regulated by a close interplay between the digestive tract, energy storage such as in adipose tissue and liver and the brain. Appetite is assessed in a subject by measuring the amount of food ingested and by assessing the subject's desire to eat.

"Dysregulation of appetite" refers to an abnormal appetite which includes increased appetite as well as decreased appetite which is permanently present or reoccurs several times a week and thus contributes to anorexia nervosa, bulimia nervosa, cachexia, wasting disease, overeating, binge eating disorder and hyperphagia.

In one embodiment, the subject suffers from an eating disorder selected from the group consisting of anorexia nervosa, bulimia nervosa, binge eating disorder, cachexia and wasting diseases and more particularly, anorexia nervosa, bulimia nervosa and binge eating disorder.

"Anorexia" relates to the decreased sensation of appetite thus resulting in a reduced appetite. While the term in non-scientific publications is often used interchangeably with anorexia nervosa, many possible causes exist for a decreased appetite, some of which may be harmless, while others indicate a serious clinical condition or pose a significant risk.

"Anorexia nervosa" (AN) refers in the context of the invention to an eating disorder characterized by immoderate food restriction that is characterized by failure to maintain body weight of at least 85% of the normal body weight. Furthermore the subject suffering from anorexia nervosa has an irrational fear of gaining weight, as well as a distorted body self-perception, where the subject sees him/herself as overweight despite overwhelming evidence to the contrary.

Accordingly, a person suffering from anorexia nervosa preferably disposes at least one of the psychological traits selected from the group consisting of body dissatisfaction, drive for thinness, perfectionism, ineffectiveness, interpersonal distrust, social insecurity and anhedonia. Preferably, a person suffering from anorexia nervosa disposes at least one of the psychological traits selected from the group consisting of body dissatisfaction, drive for thinness and perfectionism.

Still preferably, a person suffering from anorexia nervosa disposes at least one of the psychological traits selected from the group consisting of ineffectiveness, interpersonal distrust, social insecurity and anhedonia.

In a further embodiment, a subject suffering from anorexia nervosa has a BMI inferior to 17.

The "BMI" or "body mass index" is defined as the subject's body mass divided by the square of his height. The formulae universally used in medicine produce a unit of measure of $kg/m^2$.

"Bulimia" or "Bulimia nervosa" is an eating disorder characterized by binge eating and purging, or consuming a large amount of food in a short amount of time followed by an attempt to rid oneself of the food consumed (purging), typically by vomiting, taking a laxative or diuretic, and/or excessive exercise. Some subjects may tend to alternate between bulimia nervosa and anorexia nervosa. Subject suffering from bulimia may be characterized by a normal BMI range, usually inferior to 25.

"Binge eating disorder" or "BED" refers to an eating disorder characterized by binge eating consisting of eating, in a discrete period of time (e.g. within any 2-hour period), an amount of food that is larger than most people would eat in a similar period of time under similar circumstances, and is accompanied by a feeling of loss of control. The binge eating occurs, on average, at least twice a week for 6 months. Contrary to bulimia the binge eating is not associated with the recurrent use of inappropriate compensatory behavior. Subjects suffering from BED are seriously worried about the binge eating. Furthermore, subjects suffering from BED eat until being physically uncomfortable and nauseated due to the amount of food consumed and/or eat when bored or depressed and/or eat large amounts of food even when not really hungry and/or eat alone during periods of normal eating, owing to feelings of embarrassment about food and/or feel disgusted, depressed, or guilty after binge eating. Subjects with binge eating disorder act impulsively and feel a lack of control over their eating. Furthermore, subject suffering from binge eating disorder have problems coping with stress, anxiety, anger, sadness, boredom and worry.

In the context of this invention, subjects suffering of BED are preferably obese and have a BMI superior to 30.

"Overeating" is the consumption of excess food in relation to the energy that an organism expends (or expels via excretion), leading to weight gaining. Overeating can sometimes be a symptom of binge eating disorder or bulimia. Compulsive over eaters depend on food to comfort themselves when they are stressed, suffering bouts of depression, and have feelings of helplessness.

"Hyperphagia", also known as "polyphagia" refers to excessive hunger (compulsive) or increased appetite. In one embodiment hyperphagia may be caused by disorders such as Diabetes, Kleine-Levin Syndrome, the genetic disorders Prader-Willi Syndrome and Bardet Biedl Syndrome.

"Wasting disease" refers to the process by which a debilitating disease causes muscle and fat tissue to "waste" away. Wasting can be caused by an extremely low energy intake (e.g., caused by famine), nutrient losses due to infection, or a combination of low intake and high loss.

"Cachexia" is a wasting syndrome associated with loss of weight and/or muscle atrophy and/or fatigue, weakness, and significant loss of appetite which may be caused by cancer, AIDS, chronic obstructive lung disease, multiple sclerosis, congestive heart failure, tuberculosis, familial amyloid polyneuropathy, mercury poisoning (acrodynia) and hormonal deficiency. Cachexia, or wasting, as it may also be called, is seen with several diseases, such as AIDS, cancer, post hip fracture, chronic heart failure, chronic lung disease such as chronic obstructive lung disease (COLD) and/or chronic obstructive pulmonary disease (COPD), liver cirrhosis, renal failure, and autoimmune diseases such as rheumatoid arthritis and systemic lupus, sepsis and severe infection. Furthermore, wasting is also seen in aging.

In some embodiments, cachexia is caused by cancer.

The foremost sign of cachexia is weight loss, not only of fatty tissue but also of muscle tissue and even bone. This non-fatty tissue is also known as "lean body mass."

In addition, there is loss of appetite, weakness (asthenia), and a drop in hemoglobin level (anemia).

Cachexia is found as the terminal state of many different clinical conditions or in chronic diseases such as cancer, infections, AIDS, congestive heart failure, rheumatoid arthritis, tuberculosis, post-hip fracture, cystic fibrosis and Crohn's disease. It can also occur in elderly people who do not have any obvious symptoms of disease.

"Increased appetite" refers to an appetite wherein a subject has a higher food intake than the body requires. This may or may not result in weight gain.

"Normal appetite" thus refers to a subject having a food intake that corresponds to the amount of food the body requires.

"Decreased appetite" and/or "reduced appetite" refers an appetite wherein a subject has a lower food intake than the body requires. This may or may not result in weight loss.

"Food intake" can be measured using a multitude of techniques including self-reporting using e.g. diaries or questionnaires, measurements of calorie-intake from a buffet meal, using weighing of food prior to ingestion, or weighing and analysis of paired quantities of food. The food intake may be measured on a meal basis, a daily basis, a weekly basis or a monthly basis.

In one embodiment the composition is for decreasing weight gain in the subject.

The composition may be used, for example, to decrease appetite, wherein the increased appetite is due to binge eating disorder or overeating.

In an embodiment of the invention, the treatment results in at least 1% decrease in food intake, such as a decrease of 2%, more preferably 3% or 5% or 7%, and even more preferred 10% below average food intake prior to initiation of treatment.

In another embodiment, the treatment leads to decrease in calorie intake irrespective of changes in food intake, since amount of food ingested may not be directly related to the ingested calorie intake, as the various food items such as fat, carbohydrates and proteins contain different amounts of calories per amount food.

In an embodiment of the invention, the treatment results in a at least 1% decrease in calorie intake, such as a decrease of 2%, more preferably 3%, or 5% or 7%, and even more preferred a decrease of 10% in calorie intake below average calorie intake prior to initiation of treatment.

In one embodiment the composition is for increasing weight gain in the subject.

The composition may be used, for example, to stimulate appetite, wherein the reduced appetite is due to anorexia, anorexia nervosa, bulimia nervosa, cachexia or wasting diseases, in particular anorexia, anorexia nervosa or bulimia nervosa.

In one embodiment of the invention, the treatment results in a 1% increase in food intake, such as an increase of 2%, more preferably 3% or 5% or 7%, and even more preferred 10% above average food intake compared to prior to initiation of treatment.

In another embodiment, the treatment leads to increase in calorie intake irrespective of changes in food intake, since amount of food ingested may not be directly related to the ingested calorie intake, as the various food items such as fat, carbohydrates and proteins, contain different amounts of calories per amount food.

In a preferred embodiment of the invention, the treatment results in a at least 1% increase in calorie intake, such as an increase of 2%, more preferably 3%, or 5% or 7%, and even more preferred 10% in calorie intake compared to prior to initiation of treatment.

In some embodiments, the composition is for use in the treatment or prevention of a disorder selected from the group consisting of anorexia nervosa (AN), bulimia nervosa (BN), binge eating disorder (BED), overeating, hyperphagia, wasting diseases such as cachexia, and more particularly from anorexia nervosa (AN), bulimia nervosa (BN) and binge eating disorder (BED).

Also provided is a method of treating or reducing the chances of occurrence of eating disorders in a subject, said method comprising administering to a subject in need thereof a composition comprising at least one antibiotic directed against at least one ClpB expressing bacterium and/or administering to said subject an effective amount of a composition comprising probiotics not expressing ClpB and/or a combination thereof as described below.

A subject in need thereof is a subject suffering from an eating disorder, as herein defined, in particular selected from the group consisting of anorexia nervosa (AN), bulimia nervosa (BN), binge eating disorder (BED), hyperphagia, wasting diseases such as cachexia, and more particularly from anorexia nervosa (AN), bulimia nervosa (BN) and binge eating disorder (BED).

Also provided is the use of a composition comprising at least one antibiotic directed against at least one ClpB expressing bacterium for the manufacture of a medicament intended for the treatment or prevention of eating disorders, as herein defined.

The inventors discovered that disregulated appetite is associated with the presence of ClpB protein and/or anti-ClpB antibodies and increased plasma levels of anti-α-MSH-reactive antibodies, preferably anti-ClpB IgG and/or IgM and anti-α-MSH-reactive IgG and/or IgM.

In one embodiment, reducing the amount or concentration of ClpB expressing bacteria in a subject results in the normalization of appetite in said subject.

Without being bound by theory, the composition comprising at least one antibiotic directed against at least one ClpB expressing bacterium reduces the amount of ClpB expressing bacteria, thus reducing the level or concentration of ClpB protein and/or anti-ClpB antibodies and/or reducing the level of anti-α-MSH-reactive antibodies, thus resulting in a normalized appetite.

In one embodiment, the composition used in the context of the invention is a pharmaceutical composition.

Pharmaceutical compositions used in the context of the invention are preferably designed to be appropriate for the selected mode or route of administration, and pharmaceutically acceptable diluents, carriers, and/or excipients such as dispersing agents, buffers, surfactants, preservatives, solubilizing agents, isotonicity agents, stabilizing agents, and the like are used as appropriate. Such compositions can be designed in accordance with conventional techniques as disclosed, for example, in Remington, The Science and Practice of Pharmacy, 19th Edition, Gennaro, Ed., Mack Publishing Co., Easton, Pa. 1995.

Suitable carriers for pharmaceutical compositions include any material which, when combined with the antibiotic of the invention retains the molecule's activity and is non-reactive with the subject's immune system.

The pharmaceutical compositions according to the invention may be administered orally in the form of a suitable pharmaceutical unit dosage form. The pharmaceutical compositions of the invention may be prepared in many forms that include tablets, hard or soft gelatin capsules, aqueous solutions, suspensions, and liposomes and other slow-release formulations, such as shaped polymeric gels.

The mode of administration and dosage forms are closely related to the properties of the therapeutic agents or compositions which are desirable and efficacious for the given treatment application. Suitable dosage forms include, but are not limited to, oral, intravenous, rectal, sublingual, mucosal, nasal, ophthalmic, subcutaneous, intramuscular, transdermal, spinal, intrathecal, intra-articular, intra-arterial, subarachnoid, bronchial, and lymphatic administration, and other dosage forms for systemic delivery of active ingredients.

Pharmaceutical compositions of the invention may be administered by any method known in the art, including, without limitation, transdermal (passive via patch, gel, cream, ointment or iontophoretic); intravenous (bolus, infusion); subcutaneous (infusion, depot); transmucosal (buccal and sublingual, e.g., orodispersible tablets, wafers, film, and effervescent formulations; conjunctival (eyedrops); rectal (suppository, enema)); or intradermal (bolus, infusion, depot).

Oral liquid pharmaceutical compositions may be in the form of, for example, aqueous or oily suspensions, solutions, emulsions, syrups or elixirs, or may be presented as a dry product for constitution with water or other suitable vehicle before use. Such liquid pharmaceutical compositions may contain conventional additives such as suspending agents, emulsifying agents, non-aqueous vehicles (which may include edible oils), or preservatives.

Pharmaceutical compositions of the invention may also be formulated for parenteral administration (e.g., by injection, for example, bolus injection or continuous infusion) and may be presented in unit dosage form in ampoules, pre-filled syringes, small volume infusion containers or multi-dose containers with an added preservative. The pharmaceutical compositions may take such forms as suspensions, solutions, or emulsions in oily or aqueous vehicles, and may contain formulating agents such as suspending, stabilizing and/or dispersing agents. Alternatively, the pharmaceutical compositions of the invention may be in powder form, obtained by aseptic isolation of sterile solid or by lyophilization from solution, for constitution with a suitable vehicle, e.g. sterile, pyrogen-free water, before use.

Pharmaceutical compositions suitable for rectal administration wherein the carrier is a solid are most preferably presented as unit dose suppositories. Suitable carriers include cocoa butter and other materials commonly used in the art, and the suppositories may be conveniently formed by admixture of the pharmaceutical composition with the softened or melted carrier(s) followed by chilling and shaping in molds.

For administration by inhalation, the pharmaceutical compositions according to the invention are conveniently delivered from an insufflator, nebulizer or a pressurized pack or other convenient means of delivering an aerosol spray. Pressurized packs may
comprise suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Alternatively, for administration by inhalation or insufflation, the pharmaceutical compositions of the invention may take the form of a dry powder composition, for example, a powder mix of the pharmaceutical composition and a suitable powder base such as lactose or starch. The powder composition may be presented in unit dosage form in, for example, capsules or cartridges or, e.g., gelatin or blister packs from which the powder may be administered with the aid of an inhalator or insufflator.

For intra-nasal administration, the pharmaceutical compositions of the invention may be administered via a liquid spray, such as via a plastic bottle atomizer. Typical of these are the Mistometerg (isoproterenol inhaler-Wintrop) and the Medihaler® (isoproterenol inhaler-Riker).

Pharmaceutical compositions of the invention may also contain excipient such as flavorings, colorings, anti-microbial agents, or preservatives.

The administration regimen may be for instance for a period of at least 2, 3, 4, 5, 6, 7, 8, 9, 10, 15, 20, 25, 30, 35, 40, 45, 50, 55, 60, 65, 70, 75, 80, 85, 90, 95, 100 days.

The dose range depends on the composition to be administered and is defined above.

As is well known in the medical arts, dosages for any one subject depend on many factors, including the patient's size, body surface area, age, the particular compound to be administered, sex, time and route of administration, general health, and other drugs being administered concurrently.

In one aspect of the invention, the method of treatment or prevention of the invention enables maintaining a stable body-weight by administering the composition comprising at least one antibiotic directed against at least one ClpB expressing bacterium.

Overweight or too low body weight might also be considered in certain cultures as a physical appearance that is considered to be less attractive.

Therefore in one embodiment, the invention refers to a non-therapeutic method of regulating appetite in a subject, comprising administering to said subject an effective amount of a composition comprising at least one antibiotic directed against at least one ClpB expressing bacterium.

All the definitions previously mentioned also apply to the said non therapeutical method.

In one embodiment, an effective amount or a therapeutically effective amount is at least the minimal dose, but less than a toxic dose, of an active agent which is necessary to impart therapeutic benefit or benefit to a subject. Stated another way, such an amount for treating eating disorders, for example, is an amount that induces, ameliorates, or otherwise causes an improvement in the state of the subject, as the regulation of food intake.

In one embodiment said non-therapeutic method is a cosmetic method.

As mentioned above, the invention also relates to a composition comprising probiotics not expressing ClpB protein for use in the treatment or prevention of an eating disorder.

All the definitions previously mentioned also apply to the said composition.

In one embodiment, the eating disorder is selected from the group consisting of anorexia nervosa (AN), bulimia nervosa (BN), binge eating disorder (BED), hyperphagia, wasting diseases such as cachexia, and more particularly from anorexia nervosa (AN), bulimia nervosa (BN) and binge eating disorder (BED).

It further relates to a non-therapeutic method of regulating appetite in a subject, comprising administering to said subject an effective amount of a composition comprising probiotics not expressing ClpB protein.

All the definitions previously mentioned also apply to the said non therapeutical method.

By "probiotic" is meant a food additive comprising an effective amount of a microorganism, intended to be introduced in the diet. According to WHO, probiotics are live microorganisms which, when administered in adequate amounts confer a benefit to the host health (WHO, 2001). As used herein, the expression "probiotic bacterial strain" denotes a bacterial strain that has a beneficial effect on the health and well-being of the host.

In the context of the invention, the bacterium introduced in the diet is a bacterium expressing or not expressing ClpB protein. The latter being a bacterium normally expressing the ClpB protein in which the expression of the protein would have been deleted.

In a prefered embodiment, the probiotic strain expresses or overexpresses the ClpB protein.

ClpB expressing bacteria are well-known from the skilled person and may be identified by any conventional technique.

In one embodiment, the ClpB expressing bacterium in which the expression of the protein is deleted is selected from the group constituted of bacteria known as probiotic or commensal non-pathogenic bacteria in humans, e.g. non-pathogenic *Escherichia coli*.

A bacteria not expressing ClpB protein can be prepared by methods known to the skilled person. This can for example be done by DNA recombination.

By "effective amount" is meant an amount of bacteria that allows the manifestation of the desired effect, in the context of the invention, the treatment or prevention of eating disorders. In particular, it is meant an amount of between 1000 million and 10000 million UFC·day-1.

As mentioned above, the invention also relates to a composition comprising a ClpB protein for use as a vaccine or as an immunogenic composition.

By "immunogenic composition" is meant in the context of the present invention a composition comprising a ClpB protein which provokes or immunomodulates (i.e. immunosuppress or immunostimulate) an immune response when administered to an individual or which induces the production of antibodies when administered to an individual.

By "vaccine" is meant a composition, such as the immunogenic composition described herein which is administered to immunomodulate an immune response, that will protect or treat an individual from illness, in particular due to that agent. The vaccine of the present invention is in particular a preventive (prophylactic) vaccine, for administration to the individual prior to the development of the eating disorder.

In particular, said composition is for use in the immunization against eating disorders.

More particularly, said composition is for use for preventing eating disorders.

Also provided is a method of immunization or vaccination in a subject, said method comprising administering to a subject in need thereof a composition comprising a ClpB protein.

In particular, said method is for reducing the chances of occurrence of eating disorders in a subject.

A subject in need thereof is a subject susceptible to suffer from an eating disorder.

Also provided is the use of a composition comprising a ClpB protein for the manufacture of a vaccine or immunogenic composition for the immunization against eating disorders.

In particular, said composition is for the prevention of eating disorders.

In particular, said eating disorder is selected from anorexia nervosa (AN), bulimia nervosa (BN), binge eating disorder (BED), overeating, hyperphagia, wasting diseases such as cachexia, in particular anorexia nervosa, bulimia nervosa and binge eating disorder.

In one embodiment, vaccine or immunogenic compositions can also comprise combinations of ClpB proteins disclosed herein.

Methods of obtaining a vaccine composition or immunogenic composition are well known in the art. Generally such methods involve extracting proteins from bacterial preparations using techniques such as sonication, proteolytic digestion, heat treatment, freeze-thaw treatment, osmotic shock treatment etc. . . . Examples of artificial bacterial preparations include protein preparations either in part or entirely obtained by synthetic or recombinant methods.

A typical dose for a vaccine or immunogenic composition comprising ClpB can be, for example, in the range of from about 0.01 nmol/kg to about 1000 nmol/kg; however, doses below or above this exemplary range are envisioned. In particular, said dose is from about 0.1 nmol/kg to about 100 nmol/kg of total body weight, preferably from about 0.1 nmol/kg to about 20 nmol/kg, more particularly from 0.1 nmol/kg to about 10 nmol/kg, in particular 0.1, 0.2, 0.3, 0.4, 0.5, 0.6, 0.7, 0.8, 0.9, 1, 2, 3, 4, 5, 6, 7, 8, 9, 10 nmol/kg body weight.

As regards to said vaccine and immunogenic compositions, forms suitable for injectable use include sterile aqueous solutions or dispersions and sterile powders for the extemporaneous preparation of sterile injectable solutions or dispersions In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intraarterial, intramuscular, subcutaneous, intratumoral and intraperitoneal administration. In this connection, sterile aqueous media that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion, (see for example, (see for example, Remington: The Science and Practice of Pharmacy, 21$^{st}$ Edition, Lippincot and Williams, 2005). Some variation in dosage will necessarily occur depending on the condition of the subject being treated. Moreover, for human administration, preparations should meet sterility, pyrogenicity, general safety and purity standards as required by FDA Office of Biologics standards.

Sterile injectable solutions are prepared by incorporating the active compounds in the required amount in the appropriate solvent by filtered sterilization.

As used herein, 'carrier' includes, without limitation, solvents, dispersion media, vehicles, coatings, diluents, antibacterial and antifungal agents, isotonic and absorption delaying agents, buffers, carrier solutions, suspensions, colloids, liposomes and virosomes such as those described in Bomsel et al (2011) Immunity 34: 269-280. The use of such media and agents for pharmaceutical active substances is well known in the art.

The phrase 'pharmaceutically-acceptable' or 'pharmacologically-acceptable' refers to molecular entities and compositions that do not produce an allergic or similar untoward reaction when administered to a human. The preparation of an aqueous composition that contains a protein as an active ingredient is well understood in the art. Typically, such compositions are prepared as injectables, either as liquid solutions or suspensions; solid forms suitable for solution in, or suspension in, liquid prior to injection can also be prepared.

In a particular embodiment of the invention, the immunogenic or vaccine composition further comprises one or several adjuvant(s).

The term "adjuvant" as used herein denotes a product which, added to the content of an immunogenic composition, in particular to a vaccine, increases the intensity of the immune reaction induced in the host to which said composition is administered. An adjuvant may in particular increase the quantity of specific antibodies which said mammal is capable of producing after administration of said composition and thus increases the efficiency of immunization.

Preferably, the adjuvant(s) is devoid of side effect in a human host.

Adjuvants include any compound or compounds that act to increase a protective immune response. Adjuvants can include for example, emulsifiers; muramyl dipeptides; avridine; aqueous adjuvants such as aluminum hydroxide; oxygen-containing metal salts; chitosan-based adjuvants, and any of the various saponins, oils, and other substances known in the art, such as Ampfaigen, LPS, bacterial cell wall extracts, bacterial DNA, CpG sequences, synthetic oligonucleotides and combinations thereof (Schijns et al (2000) Curr. Opin. Immunol, 12:456), Mycohacterialplilei (*phlei*) cell wall extract (CWE) (U.S. Pat. No. 4,744,984), *M. phlei* DNA (M-D A), and M-DNA-*M phlei* ceil wall complex (MCC), heat-labile enterotoxin (LT), cholera toxin (CT), cholera toxin B subunit (CTB), polymerised liposomes, mutant toxins, e.g. LTK63 and LTR72, microcapsules, interleukins (e.g. IL-113, IL-2, IL-7, IL-12, INFγ), GM-CSF, MDF derivatives, CpG oligonucleotides, LPS, MPL, phosphophazenes, Adju-Phos®, glucan, antigen formulation, liposomes, DDE, DHEA, DMPC, DMPG, DOC/Alum Complex, Freund's incomplete adjuvant, ISCOMs®, LT Oral Adjuvant, muramyl dipeptide, monophosphoryl lipid A, muramyl tripeptide, and phospatidylethanolamine. Compounds which can serve as emulsifiers include natural and synthetic emulsifying agents, as well as anionic, cationic and nonionic compounds. Oxygen-containing metal salts include salts of Al, K, Ca, Mg, Zn, Ba, Na, Li, B, Be, Fe, Si, Co, Cu, Ni, Ag, Au, and Cr which are sulphates, hydroxides, phosphates, nitrates, iodates, bromates, carbonates, hydrates, acetates, citrates, oxalates, and tartrates, and mixed forms thereof, including aluminium hydroxide, aluminium phosphate, aluminium sulphate, potassium aluminium sulphate, calcium phosphate, Maalox (mixture of aluminium hydroxide and magnesium hydroxide), beryllium hydroxide, zinc hydroxide, zinc carbonate, zinc chloride, and barium sulphateAmong the synthetic compounds, anionic emulsifying agents include, for example, the potassium, sodium and ammonium sails of lauric and oleic acid, the calcium, magnesium and aluminum salts of fatty acids, and organic sulfonates such as sodium lauryl sulfate. Synthetic cationic agents include, for example, cetyltrhethylarnmonlum bromide, while synthetic nonionic agents are exemplified by glycerylesters (e.g., glyceryl monostearate), polyoxyethylene glycol esters and ethers, and the sorbitan fatty acid esters (e.g., sorbitan monopalmitate) and their polyoxyethylene derivatives (e.g., polyoxyethylene sorbitan. monopalmitate). Natural emulsifying agents include acacia, gelatin, lecithin and cholesterol.

Other suitable adjuvants can be formed with an oil component, such as a single oil, a mixture of oils, a water-in-oil emulsion, or an oil-in-water emulsion. The oil can be a mineral oil, a vegetable oil, or an animal oil. Mineral oils are liquid hydrocarbons obtained from petrolatum via a distillation technique, and are also referred to in the art as liquid paraffin, liquid petrolatum, or white mineral oil. Suitable animal oils include, for example, cod liver oil, halibut oil, menhaden oil, orange roughy oil and shark liver oil, all of which are available commercially. Suitable vegetable oils, include, for example, canola oil, almond oil, cottonseed oil, corn oil, olive oil, peanut oil, safflower oil, sesame oil, soybean oil, and the like. Freund's Complete Adjuvant (FCA) and Freund's incomplete Adjuvant (FIA) are two common adjuvants that are commonly used in vaccme preparations, and are also suitable for use in the present invention. Both FCA and FIA are water-in-mineral oil emulsions; however, FCA also contains a killed *Mycobacterium* sp. Particularly preferred adjuvants for mucosal vaccines include galactosyl ceramide (GalCer), as described in Lee et al (2011) Vaccine 29: 417-425.

Immunomodulatory cytokines can also be used in the vaccine compositions to enhance vaccine efficacy, for example, a an adjuvant, Non-limiting examples of such cytokines include interferon alpha (IFN-α), interleukin-2 (IL-2), and granulocyte rnacrophage-colony stimulating factor (GM-CSF), or combinations thereof.

The vaccine and immunogenic compositions, may be administered by intravenous administration, intrarterially, endoscopically, intralesionally, percutaneously, subcutaneously, intramuscular, intrathecally, intraorbitally, intradermally, intraperitoneally, transtracheally, subcuticularly, by intrasternal injection, intravenous, intrarterial, intradermal, transdermal, intramuscular, intranasal, subcutaneous, percutaneous, intratracheal, intraperitoneal, by inhalation or intranasal spraying, by endotracheal route and the like. Administration of the compositions can be by infusion or injection (e.g., intravenously, intramuscularly, intracutaneousiy, subcutaneously, intrathecal, intraduodenally, intraperitoneally, and the like). Additionally, said compositions can be administered by "needle-free" delivery systems.

The injections can be split into multiple injections, with such split inoculations administered preferably substantially concurrently. When administered as a split inoculation, the dose of the immunogen is preferably, but not necessarily, proportioned equally in each separate injection. If an adjuvant is present in the vaccine composition, the dose of the adjuvant is preferably, but not necessarily, proportioned equally in each separate injection. The separate injections for the split inoculation are preferably administered substantially proximal to each other on the patient's body. In some preferred aspects, the injections are administered at least about 1 cm apart from each other on the body. In some preferred aspects, the injections are administered at least about 2.5 cm apart from each other on the body. In highly preferred aspects, the injections are administered at least about 5 cm apart from each other on the body, in some aspects, the injections are administered at least about 10 cm apart from each other on the body, in some aspects, the injections are administered more than 10 cm apart from each other on the body, for example, at least about 12.5, 15, 17.5, 20, or more cm apart from each other on the body.

Various alternative pharmaceutical delivery systems may be employed. Non-limiting examples of such systems include liposomes and emulsions. Certain organic solvents such as dimethylsulfoxide also may be employed. Additionally, the vaccine compositions may be delivered using a sustained-release system, such as semipermeable matrices of solid polymers containing the protein. The various sustained-release materials available are well known by those skilled in the art. Sustained-release capsules may, depending on their chemical nature, release the vaccine compositions over a range of several days to several weeks to several months.

The compositions are ideally administered to a subject in advance of evidence of eating disorder, or in advance of any symptom of an eating disorder.

Administration may be via a parenteral or non-parenteral route. Routes of administration include, e.g. intravenous, intrarterial, intradermal, transdermal, intramuscular, mucosal subcutaneous, percutaneous, intratracheal, intraperitoneal, perfusion and lavage. For example, administration is via a mucosal route, for example via a nasal, oral (via the mucosa of the digestive system), vaginal, buccal, rectal, sublingual, ocular, urinal, pulmonal or otolar (vie the ear) route.

The immunisation may include various 'unit doses.'

A unit dose need not be administered as a single injection but may comprise continuous infusion over a set period of time. A unit dose may contain from about 0.01 nmol/kg to about 1000 nmol/kg. In particular, said dose is from about 0.1 nmol/kg to about 100 nmol/kg of total body weight, preferably from about 0.1 nmol/kg to about 20 nmol/kg, more particularly from 0.1 nmol/kg to about 10 nmol/kg, in particular 0.1, 0.2, 0.3, 0.4, 0.5, 0.6, 0.7, 0.8, 0.9, 1, 2, 3, 4, 5, 6, 7, 8, 9, 10 nmol/kg body weight.

In one embodiment, the vaccine composition may be administered in a single daily dose, or the total daily dosage may be administered in divided doses, for example, two, three or four times daily. Furthermore, the vaccine composition may be administered in intranasal form via topical use of suitable intranasal vehicles, via transdermal routes, using those forms of transdermal skin patches well known to persons skilled in the art, by implantable pumps; or by any other suitable means of administration. To be administered in the form of a transdermal delivery system, for example, the dosage administration will, of course, be continuous rather than intermittent throughout the dosage regimen.

Vaccine administration may further comprise a prime-boost regimen. In these methods, one or more priming immunisations are followed by one or more boosting immunisations. The actual immunogenic composition can be the same or different for each immunisation and the type of immunogenic composition, the route, and formulation of the immunogens can also be varied. One useful prime-boost regimen provides for two priming immunisations, four weeks apart, followed by two boosting immunisations at 4 and 8 weeks after the last priming immunisation.

Immunisation schedules (or regimens) are well known for animals (including humans) and can be readily determined for the particular subject and composition. Hence, the compositions can be administered one or more times to the subject. Preferably, there is a set time interval between separate administrations of the immunogenic composition. While this interval varies for every subject, typically it ranges from 10 days to several weeks, and is often 2, 4, 6 or 8 weeks. For humans, the interval is typically from 2 to 6 weeks. In a particularly advantageous embodiment of the present invention, the interval is longer, advantageously about 10 weeks, 12 weeks, 14 weeks, 16 weeks, 18 weeks, 20 weeks, 22 weeks, 24 weeks, 26 weeks, 28 weeks, 30 weeks, 32 weeks, 34 weeks, 36 weeks, 38 weeks, 40 weeks, 42 weeks, 44 weeks, 46 weeks, 48 weeks, 50 weeks, 52 weeks, 54 weeks, 56 weeks, 58 weeks, 60 weeks, 62 weeks, 64 weeks, 66 weeks, 68 weeks or 70 weeks.

The immunisation regimes typically have from 1 to 6 administrations of the composition, but may have as few as 1, 2, 3, 4 or 5. The methods of inducing an immune response can also include administration of an adjuvant with the composition. In some instances, annual, biannual or other long interval (5-10 years) booster immunisation can supplement the initial immunisation protocol.

A specific embodiment of the invention provides methods of inducing an immune response against an eating disorder in a subject by administering a vaccine or immunogenic composition of the invention, one or more times to a subject wherein the ClpB protein is at a level sufficient to induce a specific immune response in the subject. Such immunisations can be repeated multiple times at time intervals of at least 2, 4 or 6 weeks (or more) in accordance with a desired immunisation regime.

The inventors discovered a correlation between ClpB protein and anti-ClpB antibodies, in particular anti-ClpB IgG and eating disorders, in particular anorexia nervosa and bulimia nervosa.

As a consequence, the present invention also concerns an in vitro method for diagnosing an eating disorder in a subject, which method comprises:
  a) measuring the level of ClpB protein and/or anti-ClpB antibodies in a biological sample from said subject;
  b) comparing said measured level of ClpB protein and/or anti-ClpB antibodies to a reference value; and
  c) deducing if the subject suffers from an eating disorder.

In the context of the invention, the subject produces antibodies directed against the bacterial protein ClpB, called anti-ClpB antibodies.

The antibodies produced by the subject in the context of the invention may be IgM, IgD, IgG, IgA and/or IgE antibodies, in particular IgG and/or IgM antibodies.

In the context of the invention, the presence of said ClpB protein in form of a ClpB expressing bacterial strain increases the production of antibodies directed against ClpB and/or antibodies against α-MSH.

The antibodies produced by the subject that are directed against α-MSH are also called auto-antibodies.

The term "auto-antibody" refers to an antibody produced by the immune system that is directed against a subject's own protein.

Preferably, the anti-ClpB antibody cross-reacts with α-MSH as defined above.

Thus, in one embodiment, the anti-ClpB antibody is also an anti-α-MSH antibody.

An "antibody" or "immunoglobulin" (Ig) may be a natural or conventional antibody in which two heavy chains are linked to each other by disulfide bonds and each heavy chain is linked to a light chain by a disulfide bond. There are two types of light chain, lambda (l) and kappa (k). There are five main heavy chain classes (or isotypes) which determine the functional activity of an antibody molecule: IgM, IgD, IgG, IgA and IgE. Each chain contains distinct sequence domains. The light chain includes two domains or regions, a variable domain (VL) and a constant domain (CL). The heavy chain includes four domains, a variable domain (VH) and three constant domains (CH1, CH2 and CH3, collectively referred to as CH). The variable regions of both light (VL) and heavy (VH) chains determine binding recognition and specificity to the antigen. The constant region domains of the light (CL) and heavy (CH) chains confer important biological properties such as antibody chain association, secretion, trans-placental mobility, complement binding, and binding to Fc receptors (FcR). The Fv fragment is the N-terminal part of the Fab fragment of an immunoglobulin and consists of the variable portions of one light chain and one heavy chain. The specificity of the antibody resides in the structural complementarity between the antibody combining site and the antigenic determinant. Antibody combining sites are made up of residues that are primarily from the hypervariable or complementarity determining regions (CDRs). Occasionally, residues from nonhypervariable or framework regions (FR) influence the overall domain structure and hence the combining site. Complementarity Determining Regions or CDRs refer to amino acid sequences which together define the binding affinity and specificity of the natural Fv region of a native immunoglobulin binding site. The light and heavy chains of an immunoglobulin each have three CDRs, designated CDR1-L, CDR2-L, CDR3-L and CDR1-H, CDR2-H, CDR3-H, respectively. A conventional antibody antigen-binding site, therefore, includes six CDRs, comprising the CDR set from each of a heavy and a light chain V region.

"Framework Regions" (FRs) refer to amino acid sequences interposed between CDRs, i.e. to those portions of immunoglobulin light and heavy chain variable regions that are relatively conserved among different immunoglobulins in a single species. The light and heavy chains of an immunoglobulin each have four FRs, designated FR1-L, FR2-L, FR3-L, FR4-L, and FR1-H, FR2-H, FR3-H, FR4-H, respectively.

As used herein, a "human framework region" is a framework region that is substantially identical (about 85%, or more, in particular 90%, 95%, 97%, 99% or 100%) to the framework region of a naturally occurring human antibody.

As used herein, a "method for diagnosing" or "diagnosing method" or simply "diagnosis" refers to a method for determining or identifying a possible disease or disorder in a subject. In the context of the invention the method of diagnosis relates to determining or identifying an eating disorder, in particular an eating disorder selected from anorexia nervosa (AN), bulimia nervosa (BN), binge eating disorder (BED), overeating, hyperphagia, wasting diseases such as cachexia, in particular anorexia nervosa, bulimia nervosa and binge eating disorder.

As used herein, the term "biological sample" means a substance of biological origin. Examples of biological samples include, but are not limited to blood, plasma, serum or saliva. Preferably, a biological sample according to the present invention is a blood, serum and/or plasma sample, in particular plasma sample. The biological sample according to the invention may be obtained from the subject by any appropriate means of sampling known from the skilled person.

The method of diagnosing an eating disorder according to the invention comprises a step b) of comparing the measured level of ClpB protein and/or anti-ClpB antibodies to a reference value.

Preferably the reference value is measured in a sample from the same tissular origin as the biological sample of the subject of step a) of the methods of the invention.

Preferably, the "reference value" corresponds to the normal level of ClpB protein and/or anti-ClpB antibodies.

As intended herein a "normal level" of ClpB protein and/or anti-ClpB antibodies means that the level of ClpB protein and/or anti-ClpB antibodies in the biological sample is within the norm cut-off values for those ClpB protein and/or anti-ClpB antibodies. The norm is dependant on the biological sample type and on the method used for measuring the level of ClpB protein and/or anti-ClpB antibodies in the biological sample. In particular, the normal level is the mean level of ClpB protein and/or anti-ClpB antibodies in a healthy population.

In particular, the reference value corresponds to the level of ClpB protein and/or anti-ClpB antibodies in a healthy subject. Accordingly, the reference value may correspond to the level of ClpB protein and/or anti-ClpB antibodies in a reference sample derived from a healthy subject.

In particular, the reference value corresponds to the level of ClpB protein and/or anti-ClpB antibodies in a healthy subject, in particular when the level of ClpB protein and/or anti-ClpB antibodies is measured in step a).

As used herein, a "healthy population" means a population constituted of subjects who have not previously been diagnosed with an eating disorder. Subjects of a healthy population preferably also do not otherwise exhibit any symptoms of an eating disorder. In other words, such subjects, if examined by a medical professional, would be characterized as healthy and free of symptoms of disease.

Accordingly, a "healthy subject" means a subject who has not previously been diagnosed with an eating disorder. A healthy subject also does not otherwise exhibit symptoms of an eating disorder. In other words, such healthy subject, if examined by a medical professional, would be characterized as healthy and free of symptoms of disease.

Preferably, a healthy subject does not display any of the eating disorders previously mentioned.

In the context of the invention the level of ClpB protein anti-ClpB antibodies may be measured by any method known to the skilled person, for example by enzyme-linked immunosorbent assay.

In particular, levels of ClpB protein is measured by immunoassay or immunoblots or by analytical methods, like for example mass spectrometry (MS), capillary electrophoresis-mass spectrometry (CE-MS), liquid chromatography coupled to mass spectrometry (LC-MS, LC-MS/MS), for example.

The term "immunoassay" as used according to the present invention includes competition, direct reaction, or sandwich type assays. Such assays include, but are not limited to, agglutination test, enzyme-labelled and mediated immunoassays, such as ELISA, biotin/avidin type assay, radioimmunoassay, immunoelectrophoresis, and immunoprecipitation, and is more directly related to ELISA.

Mass spectrometry (MS), capillary electrophoresis-mass spectrometry (CE-MS), liquid chromatography coupled to mass spectrometry (LC-MS/MS), are all analytical methods very well known by the man skilled in the art which are suitable to carry out the method according to the invention.

In a particular embodiment, levels of ClpB DNA is measured by quantifying the ClpB DNA in the stool of the subject, for example by following the method disclosed in the experimental part below under ClpB DNA assay, or as follows: DNA is extracted from the cultures of bacteria strains and purified from feces using the QIAampR DNA Stool Mini Kit (QIAGEN, France). Bacteria are dissolved in water and boiled at 100° C. during 5 min, after 1 min of centrifugation at 11,000 r.p.m., the supernatant containing the DNA is stored at −20° C. Using the NCBI primer design tool (http://www.ncbi.nlm.nih.aov/tools/primer-blast/), the following nucleotide primers are designed that amplify 180 bp DNA region coding for the ClpB protein fragment containing one identified α-MSH-like epitope Forward: 5'-GCAGCTCGAAGGCAAAACTA-3' (SEQ ID NO: 4) and Reverse: 5'-ACCGCTTCGTTCTGACCAAT-3' (SEQ ID NO: 5) (Invitrogen Custom Primers, Cergy Pontoise, France). PCR is performed in a thermocycler with Micro-Amp tubes (Eppendorf, Hambourg, Germany). The reactionis carried out in a 50 µl volume containing 25 µL of Go Taq R Green Master Mix 2× (Promega, Madison, Wis.), 1 µl (20 pmol) of each primer, 21 µl of bi-distilled water and 1 µl of bacterial DNA. PCR conditions are as follows: 3 min at 94° C. followed by 35 cycles at 94° C. for 30 s, 60° C. for 30 s, and 72° C. for 1.5 min. PCR products are visualized on a 1% agarose gel (Sigma), with the expected size of 180 bp and the specificity validated using ClpB mutant strain.

In particular, levels of antibodies reacting with ClpB are measured using enzyme-linked immunosorbent assay (ELISA).

Typically, the ClpB protein (Delphi Genetics) is coated on a typically Maxisorp plates (Nunc, Rochester, N.Y.) using for exemple 100 µl and a concentration of 2 µg/ml in typically 100 mM $NaHCO_3$ buffer, pH 9.6 for typically 72 h at 4° C. Plates are washed for example (5 min×3) in phosphate-buffered saline (PBS) with typically 0.05% Tween 200, pH 7.4, and then incubated for example overnight at 4° C. with 100 µl of mouse or rat plasma diluted 1:200 in PBS to determine free antibody levels or diluted 1:200 in typically dissociative 3 M NaCl, 1.5 M glycine buffer, pH 8.9 to determine total Antibody levels. The plates are washed (3×) and incubated with typically 100 µl of alkaline phosphatase (AP)-conjugated goat anti-rat IgG (1:2000), anti-rat IgM (1:1000), anti-mouse IgG (1:2000), or anti-mouse IgM (1:1000) all from Jackson ImmunoResearch Laboratories, Inc. (West Grove, Pa.). Following washing (3×), typically 100 µl of p-nitrophenyl phosphate solution (Sigma) is added as alkaline phosphatase substrate. After typically 40 min of incubation at room temperature, the reaction is stopped by adding 3N NaOH. The OD (optiocal density) is determined typically at 405 nm using typically a microplate reader Metertech 960 (Metertech Inc., Taipei, Taiwan). Blank OD values resulting from the reading of plates without addition of plasma samples are subtracted from the sample OD values. Each determination is typically done in duplicate. The variation between duplicate values is typically less than 5%.

Typically a similar protocol is used to measure anti-ClpB IgG and IgM antibodies in human plasma typically diluted 1:400 using typically corresponding anti-human IgG or IgM AP-conjugated antibodies.

Preferably, in particular when the level of anti-ClpB antibodies is measured using enzyme-linked immunosorbent assay, the reference value of anti-ClpB antibodies is in particular measured in OD for anti-ClpB IgG in plasma and the OD value is between 0 and 3, more preferably between 2.0 and 3.0 and/or between 0.0 and 1.0.

Preferably, in the methods of the invention, it is determined whether the measured level of ClpB protein and/or anti-ClpB antibodies is higher (increased) or lower (decreased) than the reference value according to the invention.

The inventors further discovered, that while, in controls, anti-ClpB IgG correlated negatively with the normal range of several psychological traits, in AN patients, anti-ClpB IgG correlated positively with the core psychopathological traits such as body dissatisfaction and drive for thinness.

The method may thus further comprise a step b2) wherein the psychological traits characterizing an eating disorder are evaluated.

In one embodiment, an increased value of anti-ClpB IgG antibodies than the reference value is indicative of the presence of an eating disorder in particular, AN.

In one embodiment psychopathological traits indicating the presence of an eating disorder are body dissatisfaction and drive for thinness.

In a particular embodiment, an increased value of anti-ClpB IgG than the reference value and/or the detection of physical traits associated with an eating disorder in step b2) is indicative for the presence of an eating disorder, in particular, AN.

Methods to evaluate "psychological traits" connected with an eating disorder are known to the skilled in the art.

In one example psychological traits connected with an eating disorder can be assayed using the eating disorder inventory-2.

"Eating Disorder Inventory (EDI)" is a self-report questionnaire used to assess the presence of eating disorders, (a) Anorexia Nervosa both restricting and binge-eating/purging type; (b) Bulimia Nervosa; and (c) Eating disorder not otherwise specified including Binge Eating Disorder (BED). The original questionnaire consisted of 64 questions, divided into eight subscales. EDI-2 refers to a reviewed version of 1991.

In one embodiment, step c) of the method of diagnosis of the invention refers to deducing if the subject suffers from an eating disorder wherein an increased value of anti-ClpB antibodies than the reference value is preferably indicative for the presence of an eating disorder.

In another embodiment, the detection of physical traits with an eating disorder as detected in step b2) is indicative for the presence of an eating disorder.

The method may thus comprise a further step pre-c) of determining the ratio of the level of anti-ClpB IgG that cross-react with α-MSH in said sample compared to the total level of anti-ClpB IgG determined in step a).

The ratio of the level of anti-ClpB IgG that cross-react with α-MSH may be determined for example by preincubating plasma samples of humans diluted 1:400 in PBS with typically $10^{-6}$ M α-MSH peptide (Bachem) for example overnight at 4° C. before adding the samples to typically 96-well Maxisorp plates (Nunc) coated with ClpB protein (Delphi Genetics). IgG antibodies reactive with ClpB are detected typically by ELISA using corresponding anti-human AP-conjugated antibodies (Jackson). The percentage of ClpB IgG that are cross-reactive with α-MSH may be calculated relative to levels of anti-ClpB IgG detected without absorption in each individual plasma sample equal 100%.

In a particular embodiment, an increased ratio of the level of anti-ClpB IgG that cross-react with α-MSH compared to the total level of anti-ClpB antibodies than the reference value is indicative for the presence of an eating disorder.

The invention further relates to a method of treating or reducing the chances of occurrence of an eating disorder in a subject in need thereof, comprising administering to said subject a composition comprising one antibiotic directed against at least one ClpB expressing bacterium and/or administering to said subject a composition comprising probiotics not expressing ClpB and/or a combination thereof, wherein said subject was diagnosed as suffering from an eating disorder by:

a) measuring the level of ClpB protein and/or anti-ClpB antibodies in a biological sample from said subject;

b) comparing said measured level of ClpB protein and/or anti-ClpB antibodies to a reference value; and c) deducing if the subject suffers from an eating disorder.

All the definitions previously mentioned also apply to the said method.

The invention further relates to an in vitro method of selecting subjects suffering from an eating disorder as likely to respond to a treatment reducing the level of ClpB protein and/or anti-ClpB antibodies which comprises:

a) measuring the level of ClpB protein and/or anti-ClpB antibodies in a biological sample from said subject;

b) comparing said measured level of ClpB protein and/or anti-ClpB antibodies to a reference value; and c) selecting the subject for a treatment reducing the level of ClpB protein and/or anti-ClpB antibodies, wherein said treatment reducing the level of ClpB protein and/or anti-ClpB antibodies comprises administering to said subject an effective amount of a composition comprising one antibiotic directed against at least one ClpB expressing bacterium and/or administering to said subject an effective amount of a composition comprising probiotics not expressing ClpB and/or a combination thereof.

In one embodiment, a subject having an increased value of ClpB protein and/or ClpB antibodies than the reference value is selected as being likely to respond to a treatment reducing the level of ClpB protein and/or anti-ClpB antibodies.

In one embodiment, the method thus may further comprise a step b2) wherein the psychological traits characterizing an eating disorder are evaluated as defined above.

Step c) of the method of diagnosis of the invention refers to selecting the subject for a treatment decreasing the level of protein ClpB and/or anti-ClpB antibodies, wherein a subject having an increased value of ClpB protein and/or ClpB antibodies than the reference value is selected as being likely to respond to a treatment reducing the level of ClpB protein and/or anti-ClpB antibodies.

In a particular embodiment, a subject having an increased value of ClpB protein and/or ClpB antibodies than the reference value and/or having physical traits associated with an eating disorder as detected in step b2) is selected as being likely to respond to a treatment decreasing the level of ClpB protein and/or anti-ClpB antibodies.

In one embodiment psychopathological traits indicating the presence of an eating disorder are body dissatisfaction and drive for thinness.

Furthermore, the inventors having showed that chronic intragastric delivery of E. coli in mice decreased food intake, the invention further relates to a composition comprising probiotics overexpressing ClpB protein for use in the treatment or prevention of obesity.

"Obesity" refers herein to a medical condition wherein the subject preferably has a BMI superior to 30.

By "overexpressing" is meant the artificial expression of a protein due to expression of a gene in increased quantity, here the increased expression of the gene encoding for ClpB protein.

In some embodiments, the bacterial strain, in particular probiotic bacterial strain, of the present invention is a bacterium which constitutively expresses the ClpB protein or variant thereof.

In some embodiments, the ClpB protein or variant thereof is overexpressed in the bacterium. Generally, a protein expression is "upregulated" or a protein is "over-expressed" when it is expressed or produced in an amount or yield that is higher than a given base-line yield that occurs in nature at standard conditions. Over-expression of a protein can be achieved, for example, by altering any one or more of: (a) the growth or living conditions of the host cells; (b) the polynucleotide encoding the protein; (c) the promoter used to control expression of the polynucleotide and its copy number in the cell; and (d) the host cells themselves.

In some embodiments, the bacterium is subjected to stress conditions so that the expression of the ClpB protein or variant thereof is up regulated in the bacterium. Stress may be selected from the group consisting of an exposure to heat, temperature changes, mechanical stress, or long term storage, low moisture storage and/or freeze drying or spray drying.

In some embodiments, the ClpB protein or variant thereof is overexpressed in the bacterium. Generally, a protein expression is "upregulated" or a protein is "over-expressed" when it is expressed or produced in an amount or yield that is higher than a given base-line yield that occurs in nature at standard conditions. Over-expression of a protein can be achieved, for example, by altering any one or more of: (a) the growth or living conditions of the host cells; (b) the polynucleotide encoding the protein; (c) the promoter used to control expression of the polynucleotide and its copy number in the cell; and (d) the host cells themselves.

In some embodiments, the bacterium was subjected to stress conditions so that the expression of the ClpB protein or variant thereof is up regulated in the bacterium. Stress may be selected from the group consisting of an exposure to heat, temperature changes, mechanical stress, or long term storage, low moisture storage and/or freeze drying or spray drying.

A bacteria overexpressing ClpB protein can be prepared by methods known to the skilled person. This can for example be done by bacterial transformation with vectors expressing ClpB DNA.

In some embodiments, the bacterial strain, in particular the probiotic bacterial strain, of the present invention is a bacterium which has been genetically engineered for expressing the ClpB protein or variant thereof. Typically, the bacterial strain was transformed with a nucleic acid encoding for the ClpB protein or variant thereof. The term "transformation" means the introduction of a "foreign" (i.e. extrinsic or extracellular) gene, DNA or RNA sequence to a host cell, so that the host cell will express the introduced gene or sequence to produce a desired substance, typically a protein or enzyme coded by the introduced gene or sequence. A host cell that receives and expresses introduced DNA or RNA has been "transformed". The nucleic acid may remain extra-chromosomal upon transformation of a parental microorganism or may be adapted for integration into the genome of the microorganism. Accordingly, the nucleic acid may include additional nucleotide sequences adapted to assist integration (for example, a region which allows for homologous recombination and targeted integration into the host genome) or stable expression and replication of an extrachromosomal construct (for example, origin of replication, promoter and other regulatory sequences). In some embodiments, the nucleic acid is nucleic acid construct or vector. In some embodiments, the nucleic acid construct or vector is an expression construct or vector, however other constructs and vectors, such as those used for cloning are encompassed by the invention. In some embodiments, the expression construct or vector is a plasmid. Typically, the expression construct/vector further comprises a promoter, as herein before described. In some embodiments, the promoter allows for constitutive expression of the genes under its control. However, inducible promoters may also be employed. It will be appreciated that an expression construct/vector of the present invention may contain any number of regulatory elements in addition to the promoter as well as additional genes suitable for expression of the ClpB protein or variant thereof if desired. Methods for transforming bacterial cell with extracellular nucleic acids are well known in the art.

In one embodiment, the ClpB overexpressing bacterium is selecting from bacteria known as probiotic or commensal non-pathogenic bacteria in humans, e.g. non-pathogenic *Escherichia coli*.

By "effective amount" is meant an amount of bacteria that allows the manifestation of the desired effect. In particular, it is meant an amount of between 1000 million and 10000 million UFC·day-1.

Throughout the instant application, the term "comprising" is to be interpreted as encompassing all specifically mentioned features as well optional, additional, unspecified ones. As used herein, the use of the term "comprising" also discloses the embodiment wherein no features other than the specifically mentioned features are present (i.e. "consisting of").

In a particular embodiment, the bacterial strain of the invention is lyophilized, then preferably resuspended before being administered.

Typically, the bacterial strain, in particular the probiotic bacterial strain, of the present invention is administered to the subject by ingestion (i.e. oral route).

In one embodiment, the bacterial strain, in particular the ClpB expressing or overexpressing strain is formulated in a pharmaceutical or nutraceutical formulation.

In some embodiments, the bacterial strain, in particular the probiotic bacterial strain, of the present invention is encapsulated in order to be protected against the stomach. Accordingly, in some embodiments the bacterial strain, in particular the probiotic bacterial strain, of the present invention is formulated in compositions in an encapsulated form so as significantly to improve their survival time. In such a case, the presence of a capsule may in particular delay or prevent the degradation of the microorganism in the gastrointestinal tract. It will be appreciated that the compositions of the present embodiments can be encapsulated into an enterically-coated, time-released capsule or tablet. The enteric coating allows the capsule/tablet to remain intact (i.e., undissolved) as it passes through the gastrointestinal tract, until such time as it reaches the small intestine. Methods of encapsulating live bacterial cells are well known in the art (see, e.g., U.S. patents to General Mills Inc. such as U.S. Pat. No. 6,723,358). For example, micro-encapsulation with alginate and Hi-Maize™ starch followed by freeze-drying has been proved successful in prolonging shelf-life of bacterial cells in dairy products [see, e.g., Kailasapathy K. (2002) Curr Issues Intest Microbiol 3(2), 39-48]. Alternatively, encapsulation can be done with glucomannane fibers such as those extracted from Amorphophallus konjac. Alternatively, entrapment of viable bacteria in sesame oil emulsions may also be used [see, e.g., Hou R. C., Lin M. Y., Wang M. M., Tzen J. T. (2003) J Dairy Sci 86, 424-428]. In some embodiments, agents for enteric coatings are preferably methacrylic acid-alkyl acrylate copolymers, such as Eudragit® polymers. Poly(meth)acrylates have proven particularly suitable as coating materials. EUDRAGIT® is the trade name for copolymers derived from esters of acrylic and methacrylic acid, whose properties are determined by functional groups. The individual EUDRAGIT® grades differ in their proportion of neutral, alkaline or acid groups and thus in terms of physicochemical properties. The skillful use and combination of different EUDRAGIT® polymers offers ideal solutions for controlled drug release in various pharmaceutical and technical applications. EUDRAGIT® provides functional films for sustained-release tablet and pellet coatings. The polymers are described in international pharmacopeias such as Ph.Eur., USP/NF, DMF and JPE. EUDRAGIT® polymers can provide the following possibilities for controlled drug release: gastrointestinal tract targeting (gastroresistance, release in the colon), protective coatings (taste and odor masking, protection against moisture) and delayed drug release (sustained-release formulations). EUDRAGIT® polymers are available in a wide range of different concentrations and physical forms, including aqueous solutions, aqueous dispersion, organic solutions, and solid substances. The pharmaceutical properties of EUDRAGIT® polymers are determined by the chemical properties of their functional groups. A distinction is made between:

poly(meth)acrylates, soluble in digestive fluids (by salt formation) EUDRAGIT® L (Methacrylic acid copolymer), S (Methacrylic acid copolymer), FS and E (basic butylated methacrylate copolymer) polymers with acidic or alkaline groups enable pH-dependent release of the active ingredient. Applications: from simple taste masking via resistance solely to gastric fluid, to controlled drug release in all sections of the intestine.

poly(meth)acrylates, insoluble in digestive fluids: EUDRAGIT® RL and RS (ammonio methacrylate copolymers) polymers with alkaline and EUDRAGIT® NE polymers with neutral groups enable controlled time release of the active by pH-independent swelling.

Enteric EUDRAGIT® coatings provide protection against drug release in the stomach and enable controlled release in the intestine. The dominant criterion for release is the pH-dependent dissolution of the coating, which takes place in a certain section of the intestine (pH 5 to over 7) rather than in the stomach (pH 1-5). For these applications, anionic EUDRAGIT® grades containing carboxyl groups can be mixed with each other. This makes it possible to finely adjust the dissolution pH, and thus to define the drug release site in the intestine. EUDRAGIT® L and S grades are suitable for enteric coatings. EUDRAGIT® FS 30 D (aqueous dispersion of an anionic copolymer based on methyl acrylate, methyl methacrylate and methacrylic acid) is specifically used for controlled release in the colon.

Typically, the bacterial strain, in particular the probiotic bacterial strain, of the present invention is administered to the subject in the form of a pharmaceutical, nutraceutical or food composition. Accordingly, one further aspect of the present invention relates to a pharmaceutical, nutraceutical or food composition comprising an amount of the bacterial strain, in particular the probiotic bacterial strain, of the present invention.

In some embodiments, the food composition that comprises the bacterial strain, in particular the probiotic bacterial strain, of the present invention is selected from complete food compositions, food supplements, nutraceutical compositions, and the like. The composition of the present invention may be used as a food ingredient and/or feed ingredient.

The hereinabove described formulations can be in the form of a solution or as a solid, depending on the use and/or the mode of application and/or the mode of administration.

In one embodiment, the bacterial strain, in particular the probiotic bacterial strain, of the present invention is typically added at any time during the production process of the composition, e.g. they may be added to a food base at the beginning of the production process or they may be added to the final food product.

The composition that comprises the bacterial strain, in particular the probiotic bacterial strain, of the present invention may be solid, semi-solid or liquid. It may be in the form of a medicament, a food product or food supplement, e.g. in the form of tablets, gels, powders, capsules, drinks, bars, etc. For example, the composition may be in the form of a powder packed in a sachet which can be dissolved in water, fruit juice, milk or another beverage.

"Pharmaceutical composition" refers to a composition comprising an active principle in association with a pharmaceutically acceptable vehicle or excipient. A pharmaceutical composition is for therapeutic use, and relates to health. Especially, a pharmaceutical composition may be indicated for treating or preventing obesity. According to the invention, the term "treating a disease" refers to reducing or alleviating at least one adverse effect, disorder or symptom related to obesity. The expression "Preventing a disease" or "Inhibiting the development of a disease" refers to preventing or avoiding the occurrence of obesity and associated adverse effects, disorders or symptoms.

As used herein, the term "food ingredient" or "feed ingredient" includes a formulation which is or can be added to functional foods or foodstuffs as a nutritional supplement.

By "nutritional food" or "nutraceutical" or "functional" food, is meant a foodstuff which contains ingredients having beneficial effects for health or capable of improving physiological functions.

By "food supplement", is meant a foodstuff having the purpose of completing normal food diet. A food supplement is a concentrated source of nutrients or other substances having a nutritional or physiological effect, when they are taken alone or as a combination in small amounts.

According to the invention, "functional food" summarizes foodstuff and corresponding products lately developed to which importance is attributed not only due to them being valuable as to nutrition and taste but due to particular ingredient substances. According to the invention, the middle- or long-term maintenance and promotion of health are of importance. In this context, non-therapeutic uses are preferred. The terms "nutriceuticals", "foodsceuticals" and "designer foods", which also represent embodiments of the invention, are used as synonyms, partly, however, also in a differentiated way. The preventive aspect and the promotion of health as well as the food character of the products are, however, best made clear by the term functional food. In many cases, these relate to products accumulated by assortment and selection (as is also the case in the present invention), purification, concentration, increasingly also by addition. Isolated effective substances, in particular in form of tablets or pills, are not included. Although there is no legal definition of a functional food, most of the parties with an interest in this area agree that they are foods marketed as having specific health effects beyond basic nutritional effects. Accordingly, functional foods are ordinary foods that have components or ingredients (such as those described herein) incorporated into them that impart to the food a specific functional e.g. medical or physiological benefit other than a purely nutritional effect.

In some embodiments, the drink is a functional drink or a therapeutic drink, a thirst-quencher or an ordinary drink. By way of example, the composition of the present invention can be used as an ingredient to soft drinks, a fruit juice or a beverage comprising whey protein, health teas, cocoa drinks, milk drinks and lactic acid bacteria drinks, yoghurt and drinking yoghurt, cheese, ice cream, water ices and desserts, confectionery, biscuits cakes and cake mixes, snack foods, balanced foods and drinks, fruit fillings, care glaze, chocolate bakery filling, cheese cake flavored filling, fruit flavored cake filling, cake and doughnut icing, instant bakery filling creams, fillings for cookies, ready-to-use bakery filling, reduced calorie filling, adult nutritional beverage, acidified soy/juice beverage, aseptic/retorted chocolate drink, bar mixes, beverage powders, calcium fortified soy/plain and chocolate milk, calcium fortified coffee beverage.

The composition can further be used as an ingredient in food products such as American cheese sauce, anti-caking agent for grated & shredded cheese, chip dip, cream cheese, dry blended whip topping fat free sour cream, freeze/thaw dairy whipping cream, freeze/thaw stable whipped topping, low fat and light natural cheddar cheese, low fat Swiss style yoghurt, aerated frozen desserts, hard pack ice cream, label friendly, improved economics & indulgence of hard pack ice cream, low fat ice cream: soft serve, barbecue sauce, cheese dip sauce, cottage cheese dressing, dry mix Alfredo sauce, mix cheese sauce, dry mix tomato sauce and others.

In some embodiments, the composition that comprises the bacterial strain, in particular the probiotic bacterial strain, of the present invention is used with yoghurt production, such as fermented yoghurt drink, yoghurt, drinking yoghurt, cheese, fermented cream, milk based desserts and others. Suitably, the composition can be further used as an ingredient in one or more of cheese applications, meat applications, or applications comprising protective cultures.

In some embodiments, the food composition that comprises the bacterial strain, in particular the probiotic bacterial strain, of the present invention is suitable for preparing meal replacement product. As used herein, the term "meal replacement product" unless otherwise specified, includes any nutritional product containing protein, carbohydrate, lipid, vitamins and minerals, the combination of which is then suitable as a sole or primary nutrition source for a meal. Typically, the meal replacement product comprises at least one carbohydrate source, at least one lipid source and/or at least one protein source. As protein source, any suitable dietary protein may be used, for example animal proteins (such as milk proteins, meat proteins and egg proteins); vegetable proteins (such as soy protein, wheat protein, rice protein, and pea protein); mixtures of free amino acids; or combinations thereof. Milk proteins such as casein and whey, and soy proteins are particularly preferred. The proteins may be intact or hydrolyzed or a mixture of intact and hydrolyzed proteins. It may be desirable to supply partially hydrolyzed proteins (degree of hydrolysis between 2 and 20%), for example for animals believed to be at risk of developing cows' milk allergy. If hydrolyzed proteins are required, the hydrolysis process may be carried out as desired and as is known in the art. For example, a whey protein hydrolysate may be prepared by enzymatically hydrolyzing the whey fraction in one or more steps. If the whey fraction used as the starting material is substantially lactose free, it is found that the protein suffers much less lysine blockage during the hydrolysis process. This enables the extent of lysine blockage to be reduced from about 15% by weight of total lysine to less than about 10% by weight of lysine; for example about 7% by weight of lysine which greatly improves the nutritional quality of the protein source. If the composition includes a fat source, the fat source preferably provides 5% to 40% of the energy of the composition; for example 20% to 30% of the energy. A suitable fat profile may be obtained using a blend of canola oil, corn oil and high-oleic acid sunflower oil. The source of carbohydrates preferably provides 40% to 80% of the energy of the composition. Any suitable carbohydrate may be used, for example sucrose, lactose, glucose, fructose, corn syrup solids, maltodextrins, and mixtures thereof. Typically, substituting one daily meal by an energy restricted diet with a meal replacement contributes to the maintenance of weight after weight loss.

The food composition that comprises the bacterial strain, in particular the probiotic bacterial strain, of the present invention typically comprises carriers or vehicles. "Carriers" or "vehicles" mean materials suitable for administration and include any such material known in the art such as, for example, any liquid, gel, solvent, liquid diluent, solubilizer, or the like, which is non-toxic and which does not interact with any components, in particular with the bacterial strain, of the composition in a deleterious manner. Examples of nutritionally acceptable carriers include, for example, water, salt solutions, alcohol, silicone, waxes, petroleum jelly, vegetable oils, polyethylene glycols, propylene glycol, liposomes, sugars, gelatin, lactose, amylose, magnesium stearate, talc, surfactants, silicic acid, viscous paraffin, perfume oil, fatty acid monoglycerides and diglycerides, petroethral fatty acid esters, hydroxymethyl-cellulose, polyvinylpyrrolidone, and the like.

In some embodiments, the food composition that comprises the bacterial strain, in particular the probiotic bacterial strain, of the present invention comprises an amount of dietary fibers. Dietary fiber passes through the small intestine undigested by enzymes and functions as a natural bulking agent and laxative. Dietary fiber may be soluble or insoluble and in general a blend of the two types is preferred. Suitable sources of dietary fiber include soy, pea, oat, pectin, guar gum, gum Arabic, fructooligosaccharides, galactooligosaccharides, sialyl-lactose and oligosaccharides derived from animal milks. In some embodiments, the dietary fiber is selected among mannans. Mannans (such as glucomannans and galactomannans), such as guar gum, locust bean gum, konjac, and xanthan gum, are present in some plant cell walls. The glucomannans are generally comprised of (1-4)-β-linked glucose and mannose units, while the galactomannans are generally comprised of a (1-4)-β-mannan backbone substituted with single units of (1-6)-α-galactose. Many endospermic legumes, such as guar and locust bean, contain galactomannans in the endosperm during seed development. Glucomannans have also been found as a minor component of cereal grains.

In some embodiments, the food composition that comprises the bacterial strain, in particular the probiotic bacterial strain, of the present invention contains minerals and micronutrients such as trace elements and vitamins in accordance with the recommendations of Government bodies such as the USRDA. For example, the composition may contain per daily dose one or more of the following micronutrients in the ranges given: 300 to 500 mg calcium, 50 to 100 mg magnesium, 150 to 250 mg phosphorus, 5 to 20 mg iron, 1 to 7 mg zinc, 0.1 to 0.3 mg copper, 50 to 200 µg iodine, 5 to 15 µg selenium, 1000 to 3000 µg beta carotene, 10 to 80 mg Vitamin C, 1 to 2 mg Vitamin B1, 0.5 to 1.5 mg Vitamin B6, 0.5 to 2 mg Vitamin B2, 5 to 18 mg niacin, 0.5 to 2.0 µg Vitamin B12, 100 to 800 µg folic acid, 30 to 70 µg biotin, 1 to 5 µg Vitamin D, 3 to 10 µg Vitamin E.

In some embodiments, the composition that comprises the bacterial strain, in particular the probiotic bacterial strain, of the present invention contains emulsifiers. Examples of food grade emulsifiers typically include diacetyl tartaric acid esters of mono- and di-glycerides, lecithin and mono- and di-glycerides. Similarly, suitable salts and stabilizers may be included.

In some embodiments, the food composition that comprises the probiotic bacterial strain of the present invention contains at least one prebiotic. "Prebiotic" means food substances intended to promote the growth of the probiotic bacterial strain of the present invention in the intestines. The prebiotic may be selected from the group consisting of oligosaccharides and optionally contains fructose, galactose, mannose, soy and/or inulin; and/or dietary fibers.

In some embodiments, the composition that comprises the bacterial strain, in particular the probiotic bacterial strain, of the present invention contains protective hydrocolloids (such as gums, proteins, modified starches), binders, film forming agents, encapsulating agents/materials, wall/shell materials, matrix compounds, coatings, emulsifiers, surface active agents, solubilizing agents (oils, fats, waxes, lecithins etc.), adsorbents, carriers, fillers, co-compounds, dispersing agents, wetting agents, processing aids (solvents), flowing agents, taste masking agents, weighting agents, jellifying agents, gel forming agents, antioxidants and antimicrobials. The composition may also contain conventional pharmaceutical additives and adjuvants, excipients and diluents, including, but not limited to, water, gelatin of any origin, vegetable gums, ligninsulfonate, talc, sugars, starch, gum arabic, vegetable oils, polyalkylene glycols, flavoring agents, preservatives, stabilizers, emulsifying agents, buffers, lubricants, colorants, wetting agents, fillers, and the like. In all cases, such further components will be selected having regard to their suitability for the intended recipient.

The invention will now be described in more detail with reference to the following figures and examples.

Sequences

SEQ ID NO: 1 shows the amino acid sequence of the chaperon protein ClpB from *E. Coli* K12 referenced under NCBI Reference Number NP 417083.1 and referenced under Uni-Prot entry P63284.

SEQ ID NO: 2 shows amino acids 542 to 548 of the amino acid sequence of the chaperon protein ClpB from *E. Coli* K12 of SEQ ID NO: 1.

SEQ ID NO: 3 shows the amino acid sequence of α-MSH from *Homo sapiens* referenced under Gen Pept Sequence ID, PRF: 223274.

SEQ ID NO: 4 shows the nucleic acid sequence of the nucleotide primers ClpB.

SEQ ID NO: 5 shows the nucleic acid sequence of the nucleotide primers ClpB.

FIGURES

FIGS. 1A-E: Proteomic identification of molecular mimicry between *E. coli* K12 proteins and α-MSH.

(a) 2D GE of *E. coli* cytoplasmic proteins. (b, c) Immunoblots of *E. coli* proteins detected with Rb anti-α-MSH IgG, preadsorbed (c) or not (b) with α-MSH. Circles in red surround the spots specifically recognized by α-MSH IgG which were used for protein identification. Circles in blue indicate nonspecific spots. Proteins identified in the spots 1-4 are isoforms of ClpB. (d) α-MSH and ClpB amino-acid sequence alignments using the Stretcher program. (e) Western blot of the recombinant ClpB, revealed with anti-α-MSH IgG. Lanes 1 and 2, 20 and 10 µg of ClpB, respectively.

FIGS. 2A-K. ClpB immunization in mice.

ClpB-immunized mice (ClpB+Adj) were compared with mice receiving adjuvant (Adj), PBS or controls (Ctr). (a) Body weight changes during 32 days of the study. Food intake and feeding pattern were studied during the last 2 weeks in the BioDAQ cages. Mean daily food intake (b), meal size (c) and meal number (d) during last 10 days of the study. (e) Food intake during 24 h after injection of α-MSH (100 µg kg-1 body weight, i.p.) or PBS. (f) Plasma levels of ClpB-reactive IgG before and after adsorption with $10^{-6}$M α-MSH. (g) Affinity of anti-ClpB IgG shown as the dissociation equilibrium constants (KD values). (h) Plasma levels of α-MSH-reactive total IgG. (i) Affinity (KD) of anti-α-MSH IgG. (j) cAMP assay in human embryonic kidney-293 cells overexpressing MC4R after stimulation by α-MSH alone or together with IgG (0.5 mg ml$^{-1}$) pooled from ClpB-immunized or from Adj-injected mice. (k) The cAMP assay was performed with IgG depleted from anti-α-MSH IgG. (a) Two-way repeated measurement analysis of variance (ANOVA) before α-MSH injection (100 µg kg$^{-1}$ body weight, i.p.), P<0.0001, Bonferroni post tests *a at least, P<0.05 ClpB group vs Ctr; *b at least, P<0.05 Adj group vs Ctr.; *c, P<0.05, Student's t-test ClpB group vs PBS; and *d, P<0.05, Student's t-test ClpB group vs Ctr. (b) ANOVA P=0.0002, Tukey's post tests *P<0.001, P<0.01, # P<0.05, Student's t-test. (c) ANOVA P=0.007, Tukey's post tests **P<0.01. (e) Student's t-test, *P<0.05. (f, g) ANOVA P<0.0001, Tukey's posttests *P<0.001 ClpB+Adj vs other groups, paired t-test ## P<0.01, ### P<0.001. (h) ANOVA P=0.0002, Tukey's post tests *P<0.001, *P<0.05; (i) Kruskal-Wallis test P=0.003, Dunn's post test **P<0.01, (mean±s.e.m., n=8). (j) ANOVA P=0.005, Tukey's post test *P<0.05; ANOVA P=0.04, Student's t-test # P<0.05, aClpB vs α-MSH, bClpB vs Adj. (mean±s.e.m.; j, n=6, k, n=3).

FIGS. 3A-J: *E. coli* supplementation in mice.

Effects of intragastric daily gavage (days 1-21) in mice with either *E. coli* K12 wild-type (WT), ClpBdeficient (ΔClpB) *E. coli* K12 or LB medium on body weight (a), food intake (b), meal size (c) and meal number (d). (e) PCR detection of a 180-base pair fragment of the bacterial ClpB DNA, first lane, molecular weight marker, second lane DNA from in vitro cultures of *E. coli* K12 WT, third lane DNA from in vitro cultures of *E. coli* K12 ΔClpB, and the remaining lanes DNA from mice feces collected at day 21. Plasma levels in optical density in enzyme-linked immunosorbent assay of anti-ClpB IgM (f) and IgG (g) before and after adsorption with $10^{-6}$M α-MSH.

Plasma levels of anti-α-MSH IgM (h) and IgG (i). (j) Affinity (equilibrium constant) of anti-α-MSH IgG. (a) Two-way repeated measurements analysis of variance (ANOVA), P=0.3, Bonferroni post test day 2, **P<0.01 control (Ctr) vs *E. coli* WT. (b) ANOVA days 1-2, P=0.0006, Tukey's post tests ***P<0.001, *P<0.05, *E. coli* WT vs aCtr and bLB. (c) Kruskal-Wallis (K-W) test third week P=0.0001, Dunn's post tests, *P<0.001, **P<0.01, *E. coli* WT vs aCtr, bLB and CΔClpB. (d) ANOVA days 1-2, P=0.006, Tukey's post tests **P<0.01, *P<0.05, K-W test third week P<0.0001, Dunn's post tests, *P<0.001, P<0.01, *E. coli* WT vs aCtr, bLB and CΔClpB. (f) K-W test, before adsorption P=0.02, Dunn's post tests *P<0.05, ANOVA after adsorption, P<0.0001, Tukey's post tests **P<0.01, *E. coli* WT vs other groups. (g) ANOVA before adsorption, P=0.01, Tukey's post tests *P<0.05, *E. coli* WT vs other groups, paired t-test ## P<0.01. (h) Student's t-test, *E. coli* WT vs other groups *P<0.05. (j) K-W test P=0.02, Dunn's post test *P<0.05, Mann-Whitney test, # P<0.05. (mean±s.e.m., n=8).

FIGS. 4A-F. Anti-ClpB antibodies in ED patients.

Plasma levels of anti-ClpB IgG (a) and IgM (b) in healthy women (control, Ctr) and in patients with AN, BN and BED. Plasma levels of ClpB IgG (c) and IgM (d) before and after adsorption with $10^{-6}$M α-MSH. Percentage of α-MSH crossreactive anti-ClpB IgG (e) and IgM (f). (b) Student's t-test *P<0.05. (c, d) Paired t-tests, *P<0.001, P<0.01. (e) Kruskal-Wallis test P<0.0001, Dunn's post test, **P<0.01, Mann-Whitney test # P<0.05. (f) Analysis of variance P=0.02, Tukey's post test *P<0.05. (mean±s.e.m., Ctr, n=65, AN, n=27 BN, n=32 and BED, n=14).

Figure 5:
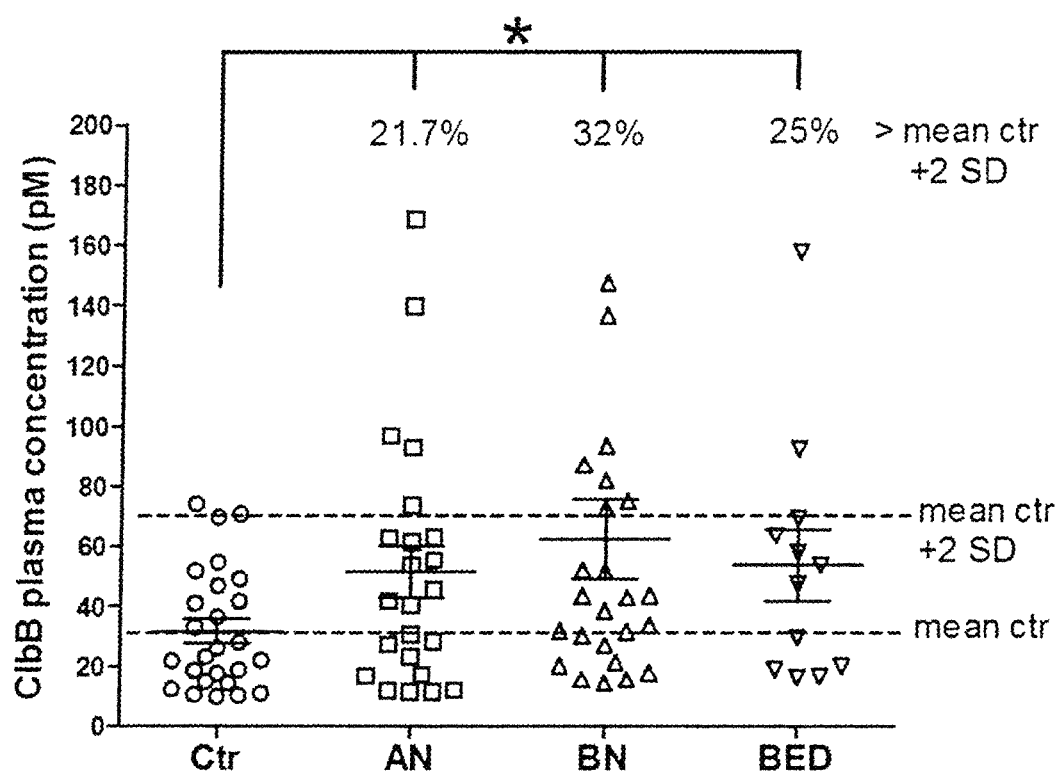

FIG. 5. Plasma concentrations of bacterial ClpB protein in patients with eating disorders and healthy controls (Ctr).

AN, anorexia nervosa, BN, bulimia nervosa, BED, binge-eating disorder. *p<0.05 Student's t-test of mean ClpB concentrations vs. Ctr. Percentage (%) of patients having ClpB concentrations higher than mean+2 standard deviations (SD) of controls.

Figure 6:
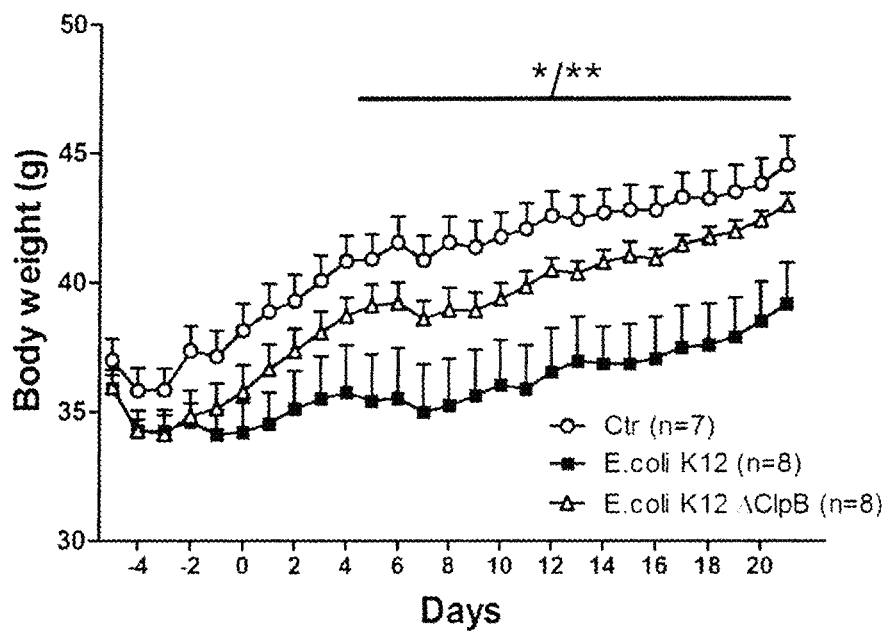

FIG. 6: Body weight dynamics in obese ob/ob mice before and during (Days 0-21) intragastric gavage with *E. coli* K12, *E. coli* K12 ΔClpB, both in Mueller-Hilton (MH) medium, or with MH medium only, as a control (Ctr). 2-way ANOVA, Effect of treatment: p=0.01, Bonferroni post-tests Ctr. vs. *E. coli* K12, *p<0.05 and **p<0.01. Mean±SEM.

Figure 7:
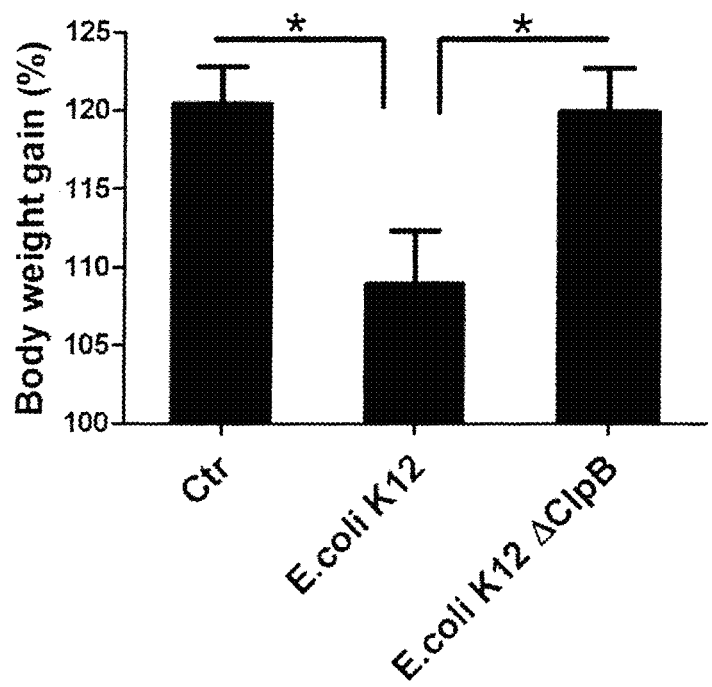

FIG. 7: Percentage of mean body weight change (from the day of randomization=100%) in obese ob/ob mice after 3 weeks of intragastric gavage with *E. coli* K12 (n=8), *E. coli* K12 ΔClpB (n=8), both in Mueller-Hilton (MH) medium, or with the MH medium only, as a control (Ctr., n=7). ANOVA p=0.01, Tukey's post-tests *p<0.05. Mean±SEM.

Figure 8:
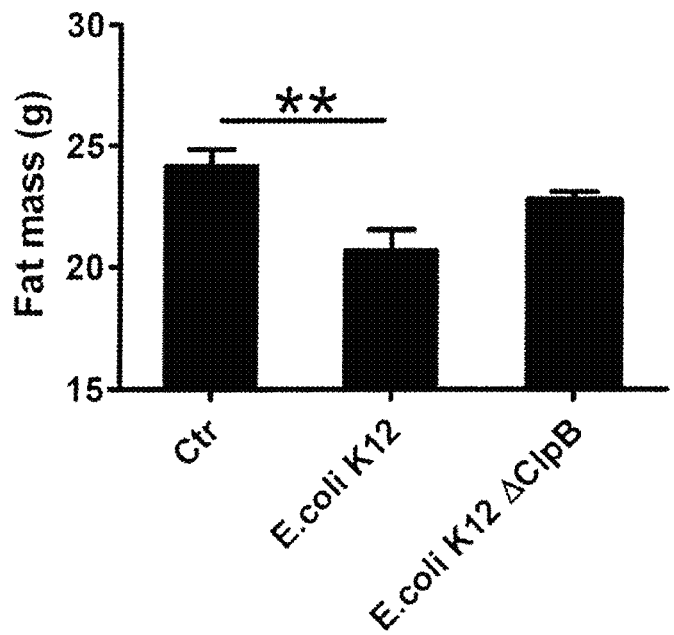

FIG. 8: Fat content in obese ob/ob mice measured by EchoMRI after 3 weeks of intragastric gavage with *E. coli* K12 (n=8), *E. coli* K12 ΔClpB (n=8), both in Mueller-Hilton (MH) medium, or with the MH medium only, as a control (Ctr., n=7). ANOVA p=0.005, Tukey's post-test **p<0.01. Mean±SEM.

Figure 9:
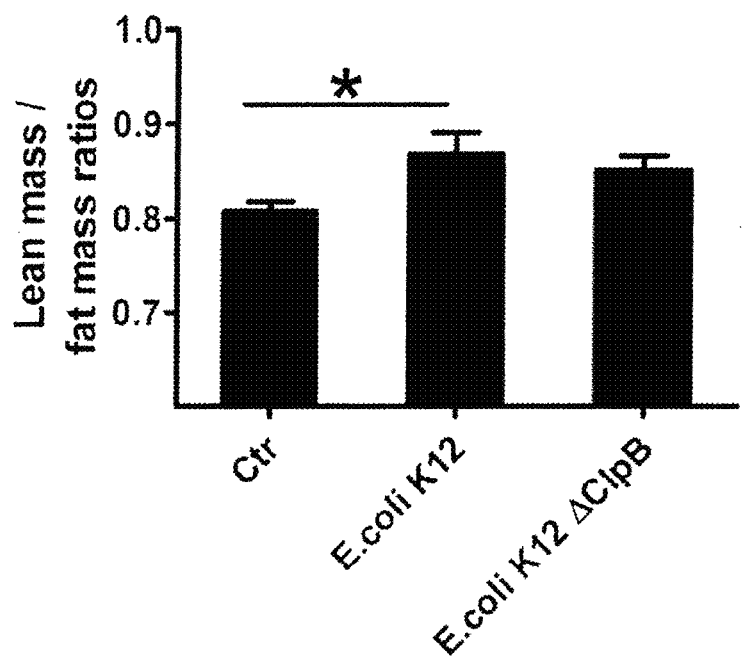

FIG. 9: Lean to fat mass ratios in obese ob/ob mice measured by EchoMRI after 3 weeks of intragastric gavage with *E. coli* K12 (n=8), *E. coli* K12 ΔClpB (n=8), both in Mueller-Hilton (MH) medium, or with the MH medium only, as a control (Ctr., n=7). ANOVA p=0.05, Student's t-test *p<0.05. Mean±SEM.

Figure 10:
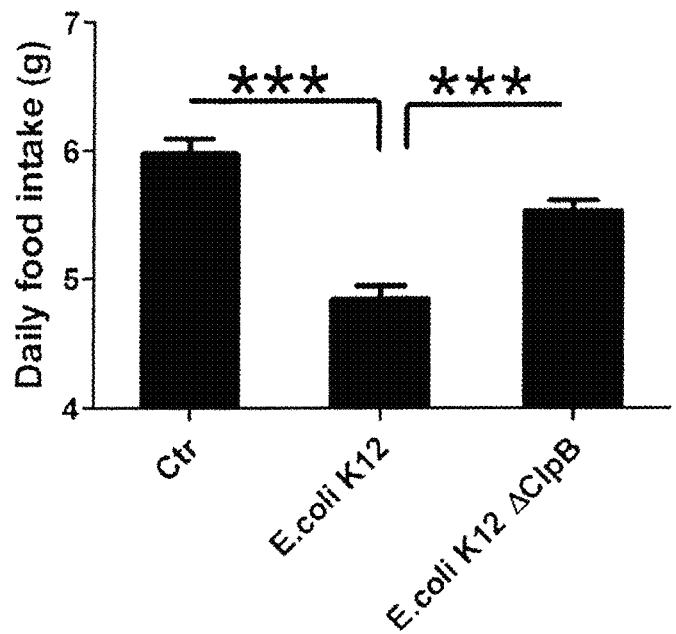

FIG. 10: Mean daily food intake in obese ob/ob mice during 3 weeks of intragastric gavage with *E. coli* K12 (n=8), *E. coli* K12 ΔClpB (n=8), both in Mueller-Hilton (MH) medium, or with the MH medium only, as a control (Ctr., n=7). ANOVA p<0.0001, Tukey's post-test ***p<0.001. Mean±SEM.

Figure 11:
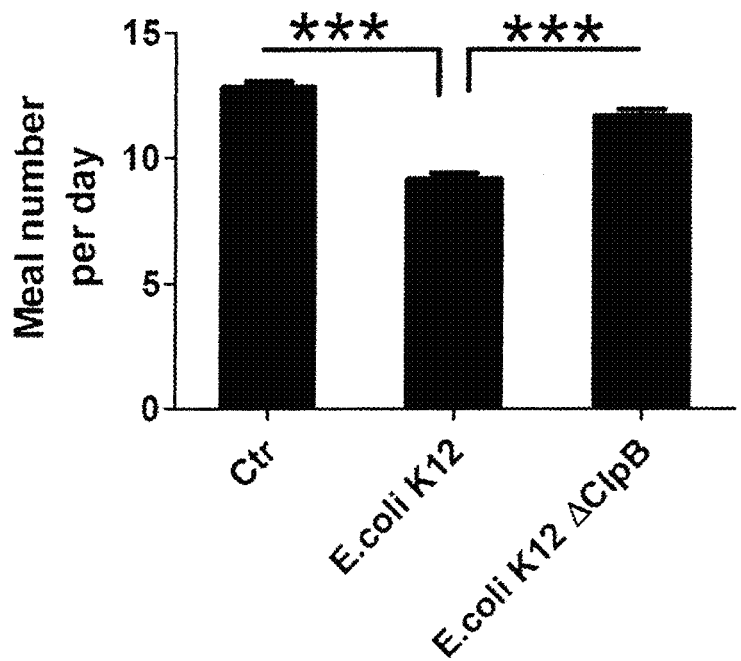

FIG. 11: Mean daily meal number in obese ob/ob mice during 3 weeks of intragastric gavage with *E. coli* K12 (n=8), *E. coli* K12 ΔClpB (n=8), both in Mueller-Hilton (MH) medium, or with the MH medium only, as a control (Ctr., n=7). ANOVA p<0.0001, Tukey's post-test ***p<0.001. Mean±SEM.

Figure 12:
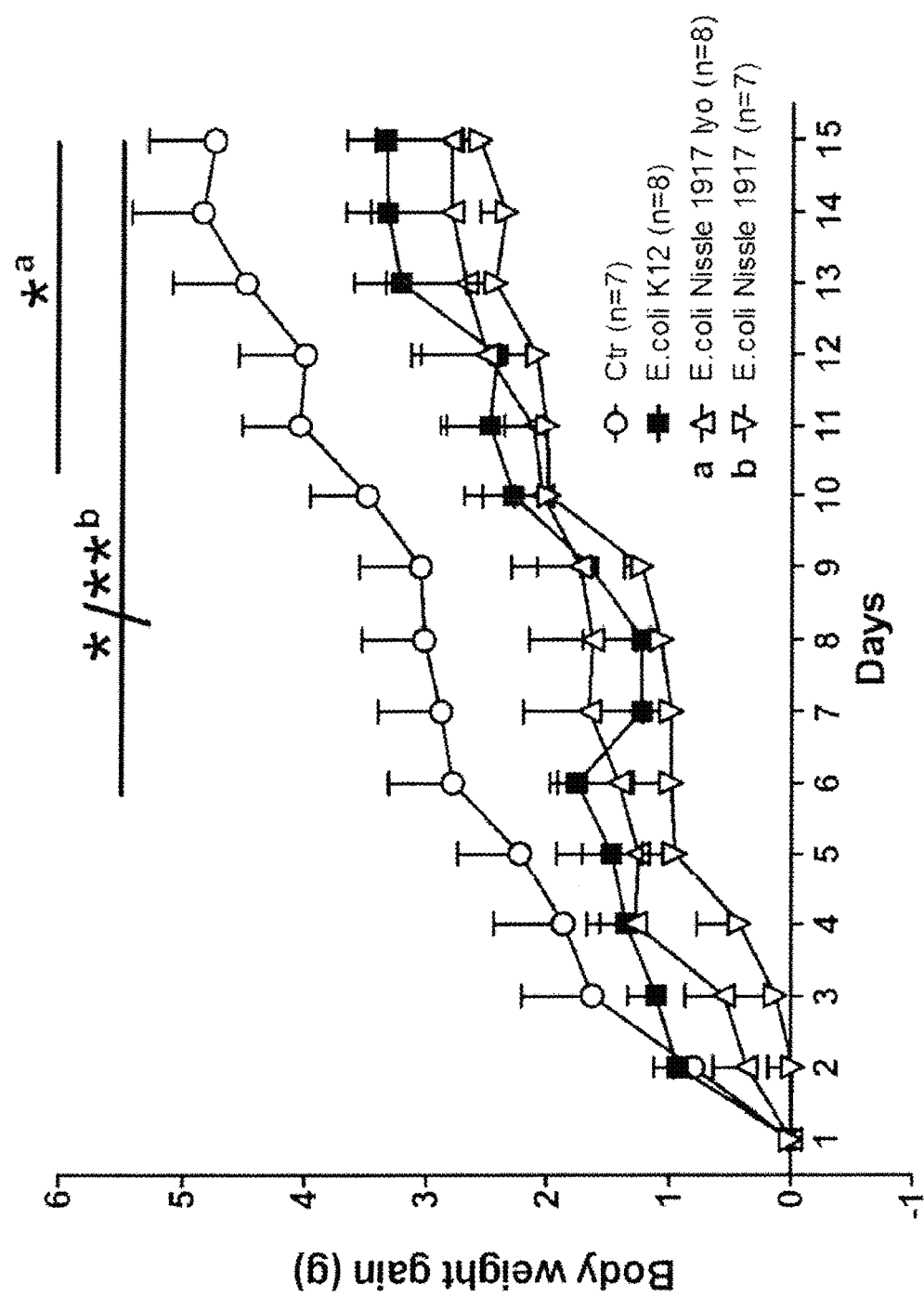

FIG. 12: Daily body weight gain in obese ob/ob mice during intragastric gavage with *E. coli* K12, *E. coli* Niessle 1917, *E. coli* Niessle 1917 lyophilized (lyo), all in Mueller- Hilton (MH) medium, or with MH medium only, as a control (Ctr). 2-way ANOVA, p=0.02, Bonferroni post-tests a, Ctr. vs. *E. coli* Niessle 1917 lyo and b, Ctr. vs. *E. coli* Niessle 1917, *p<0.05 and **p<0.01. Mean±SEM.

Figure 13:
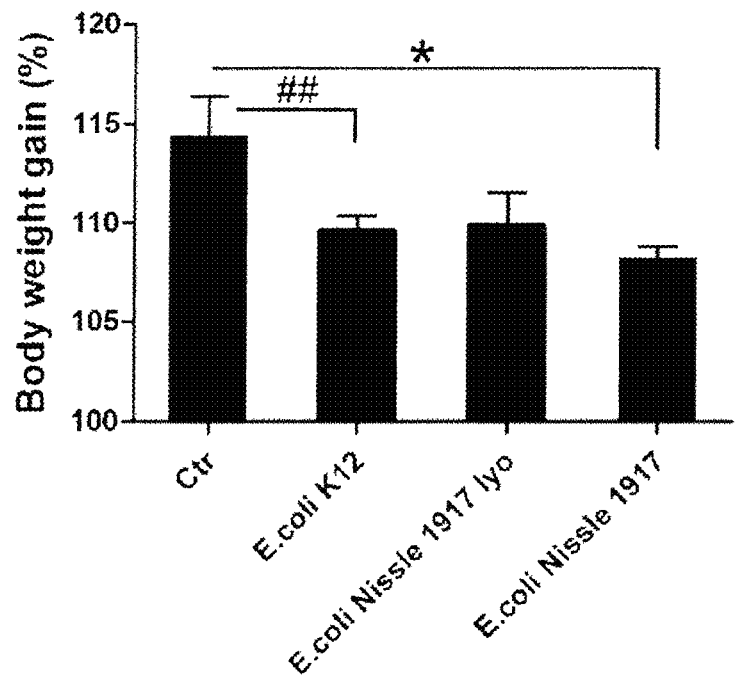

FIG. 13: Percentage of mean body weight change (from the day of randomization=100%) in obese ob/ob mice after 2 weeks of intragastric gavage with *E. coli* K12, *E. coli* Niessle 1917, *E. coli* Niessle 1917 lyophilized (lyo), all in Mueller-Hilton (MH) medium, or with MH medium only, as a control (Ctr). Kruskal-Wallis p<0.01, Dunn's post-test *p<0.05, Mann-Whitney test ## p<0.01. Mean±SEM.

Figure 14:
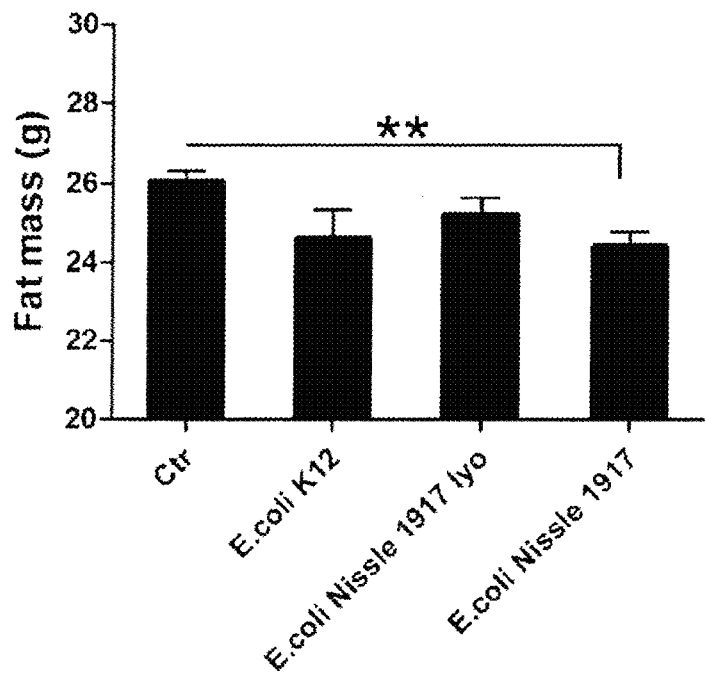

FIG. 14: Fat content in obese ob/ob mice measured by EchoMRI after 2 weeks of intragastric gavage with *E. coli* K12, *E. coli* Niessle 1917, *E. coli* Niessle 1917 lyophilized (lyo), all in Mueller-Hilton (MH) medium, or with MH medium only, as a control (Ctr). Student's t-test **p<0.01. Mean±SEM.

Figure 15:
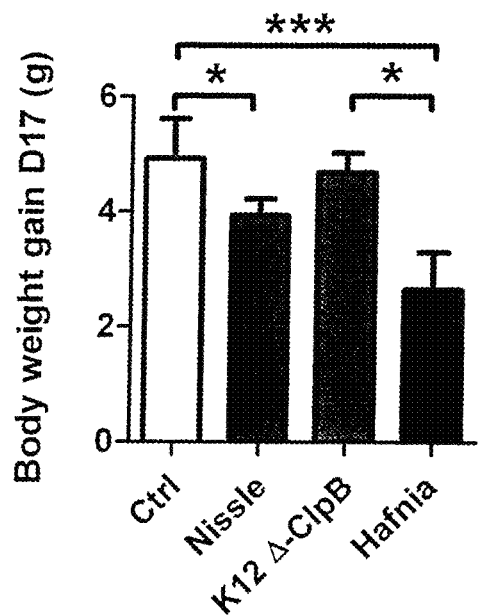

FIG. 15: Body weight gain (in g) in obese ob/ob mice after 17 days of intragastric gavage with *E. coli* Niessle 1917 (Nissle) (n=15), *E. coli* K12 (K12 Δ-ClpB) (n=15) or *Hafnia alvei* AF036 (*Hafnia*) (n=15), all in Mueller-Hilton (MH) medium, or with MH medium only, as a control (Ctrl) (n=12).

Figure 16:
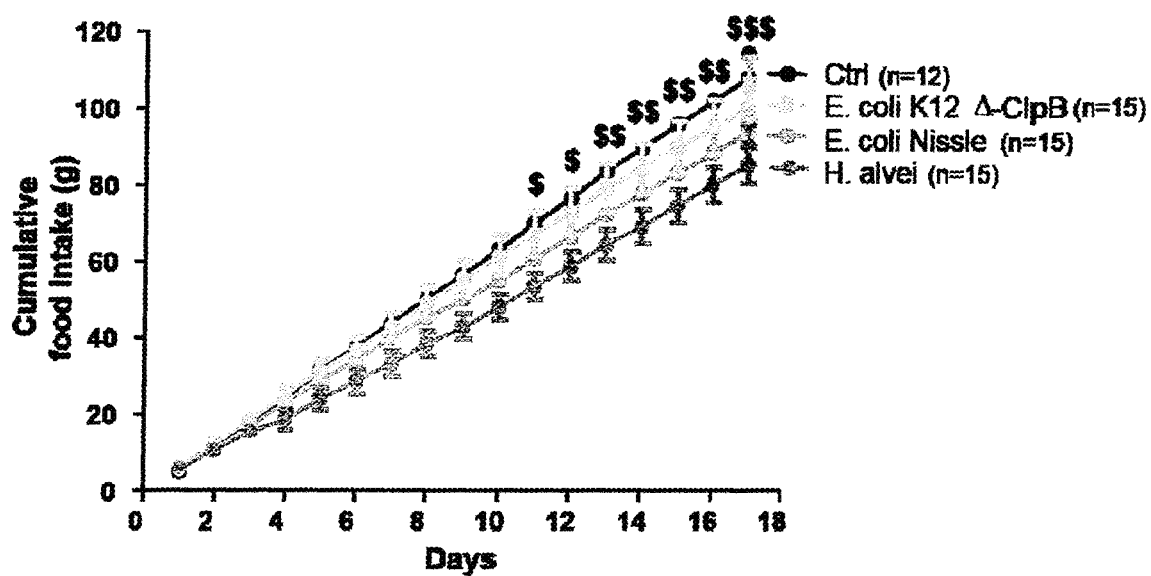

FIG. 16: Cumulative food intake (in g) in obese ob/ob mice after 17 days of intragastric gavage with *E. coli* Niessle 1917 (Nissle) (n=15), *E. coli* K12 (K12 Δ-ClpB) (n=15) or *Hafnia alvei* AF036 (*Hafnia*) (n=15), all in Mueller-Hilton (MH) medium, or with MH medium only, as a control (Ctrl) (n=12).

Figure 17A:
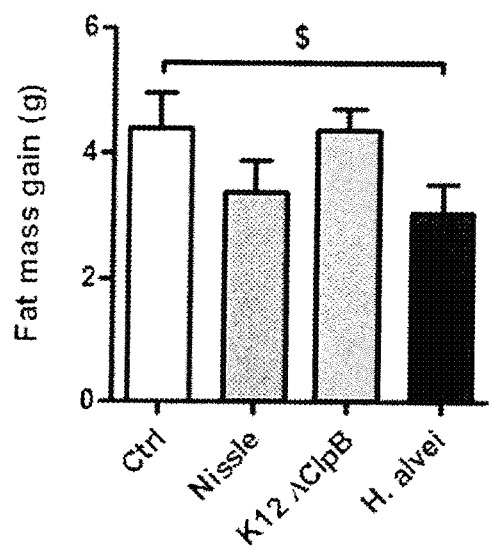
Figure 17B:
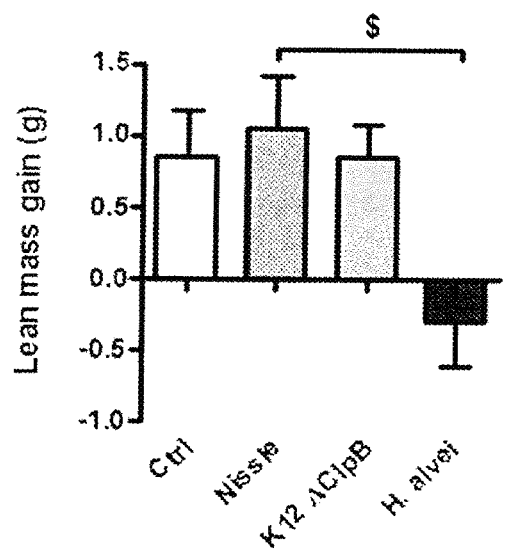
Figure 17C:
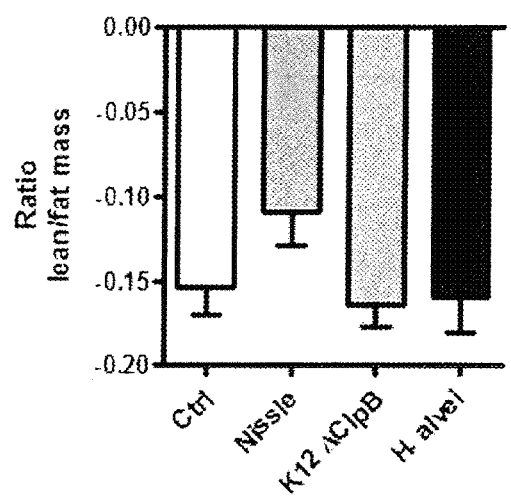

FIGS. 17A-C: Fat and lean mass gain in obese ob/ob mice measured by EchoMRI after 17 days of intragastric gavage with *E. coli* Niessle 1917 (Nissle) (n=15), *E. coli* K12 (K12 ΔClpB) (n=15) or *Hafnia alvei* AF036 (*H. alveri*) (n=15), all in Mueller-Hilton (MH) medium, or with MH medium only, as a control (Ctrl) (n=12). A. Fat mass gain (in g). B. Lean mass gain (in g). C. Lean-to-fat mass ratios.

FIGS. 18A-C: High fat diet validation. A. Body weight (in g) in mice fed with a high fat/high carbs diet (HFD) (n=48) and in mice fed with a control diet (Ctrl) (n=8). B. Fat mass (in g). C. Lean mass (in g).

Figure 19:
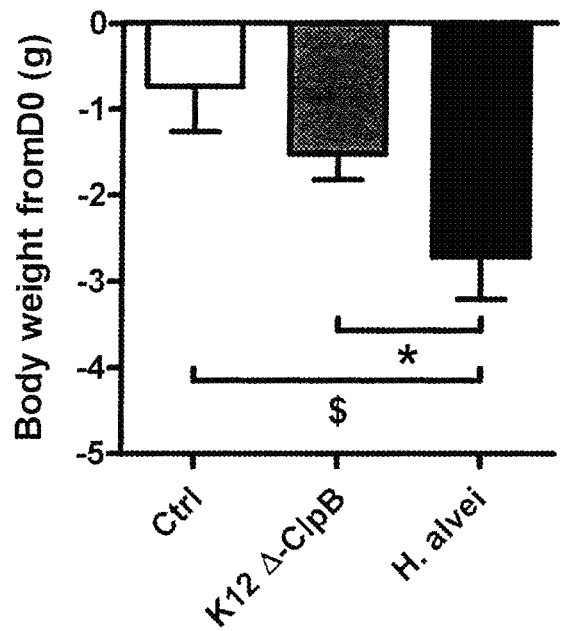

FIG. 19: Reduction in body weight gain from D0 in high fat diet (HFD)-induced obese mice after 14 days of intragastric gavage with *E. coli* K12 (K12 Δ-ClpB) or *Hafnia alvei* AF036 (*H. alvei*), all in Mueller-Hilton (MH) medium, or with MH medium only, as a control (Ctrl).

Figure 20A:
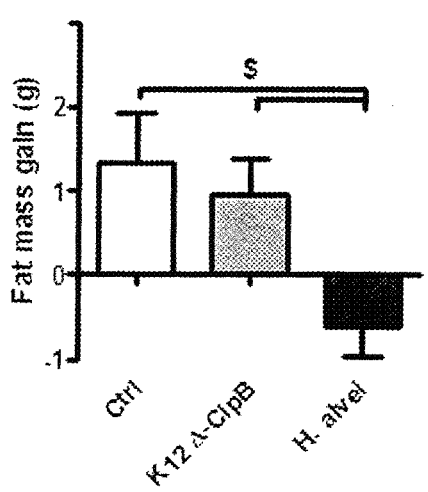
Figure 20B:
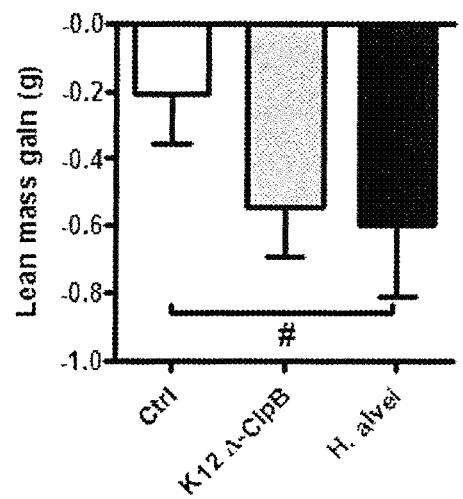

FIGS. 20A-B: Fat and lean mass gain from D0 in high fat diet (HFD)-induced obese mice after 14 days of intragastric gavage with *E. coli* K12 (K12 Δ-ClpB) or *Hafnia alvei* AF036 (*H. alvei*), all in Mueller-Hilton (MH) medium, or with MH medium only, as a control (Ctrl). A. Fat mass gain (in g). B. Lean mass gain (in g).

EXAMPLES

The following examples demonstrate that the ClpB chaperon protein of commensal gut bacteria *E. Coli* K12 is a conformational mimetic of α-melanocyte-stimulating hormone (α-MSH), a neuropeptide involved in the regulation of energy metabolism and emotion. They also reveal a molecular link between ClpB expressing gut bacteria and the regulation of motivated behavior and emotion via production of ClpB protein and anti-ClpB antibodies crossreactive with α-MSH. They further support the involvement of ClpB-expressing microorganisms in increased ClpB protein and ClpB antibody production and establishment of abnormal feeding behavior and emotion.

Example 1

Materials and Methods

*E. coli* K12 Culture and Protein Extraction

The bacterial strain used in this study was *E. coli* K12, provided by UMR 6270 CNRS Laboratory in Rouen University, France. *E. coli* K12 was grown in 250 ml Luria Bertani (LB) broth (MP Biomedicals, Illkirch, France) at 37° C. for 24 h. Protein extraction was performed as described by Marti et al. (PLoS ONE 2011, e26030). In brief, bacteria were harvested by centrifugation at 4000 g for 30 min at 4° C. and the resulting pellet was resuspended in extraction buffer (300 mM NaCl and 20 mM Tris-HCl, pH 8). The suspension was disrupted by sonication (3×3 min, pulse ON 1 s, OFF 1 s at 21% of amplitude) and centrifuged at 10 000 g for 10 min at 4° C. The supernatant was recovered and ultracentrifuged at 4° C. for 45 min at 60 000 g to further separate proteins into cytoplasmic (supernatant) and envelope (pellet) fractions. Protein concentrations were measured using 2-D Quant Kit (GE Healthcare, Piscataway, N.J., USA).

Two-Dimensional Polyacrylamide Gel Electrophoresis

For two-dimensional (2D) polyacrylamide gel electrophoresis (PAGE), 400 µg of *E. coli* K12 protein extract were added to iso-electro focusing buffer (7M urea, 2M thiourea and 0.5% ampholytes, pH 4-7, 20 mM DTT, 2 mM TBP, 2% CHAPS and 0.005% bromophenol blue) and solubilized for 60 min at room temperature with slight shaking. The first-dimensional gel separation was carried out using ReadyStrip IPG Strip (18 cm, pH 4-7 NL, Bio-Rad, Marnes-la-Coquette, France). After 24 h of passive rehydration of the strip with iso-electro focusing buffer, the protein sample was added to the strips through a loading cup placed at 1.5 cm from the cathode. Isoelectro focusing was performed with the Ettan IPGphor 3 System (GE Healthcare, Orsay, France) in four steps (31 500 Vh): 500 V for 1 h, 1000 V gradient, 10 000 V gradient and 10 000 V for 2 h. After two equilibration steps with 2% DTT and 2.5% iodoacetamide, respectively, the second dimension, that is, a SDS-PAGE, (10% polyacrylamide gel, 20 cm×18-cm×1 mm) was performed on an Ettan Daltsix vertical electrophoresis system (GE Healthcare) with 12 mA per gel. After SDS-PAGE, the 2D gel was fixed for 2 h in 2% (vol:vol) orthophosphoric acid and in 50% (vol:vol) methanol at room temperature. Gels were then rinsed with water, and the protein spots were visualized by CBB G-250 (Bio-Rad) staining (34% (vol:vol) methanol, 17% (wt:vol) ammonium sulfate, 2% (vol:vol) orthophosphoric acid and 0.66 g CBB G-250 per liter).

Immunoblotting

Following 2D-PAGE, *E. coli* cytoplasmic proteins were transferred onto Hybond-ECL PVDF membrane (GE Healthcare) via a dry transfer method (Trans Blot Cell, Bio-Rad, USA) and a constant current of 0.8 mA.cm$^{-2}$ of the membrane size for 2 h. After transfer, membranes were blocked with 5% (wt:vol) milk (Regilait, France) in phosphate-buffered saline (PBS; 10 mmol·l$^{-1}$ Tris, pH 8, and 150 mmol·l$^{-1}$ NaCl) plus 0.05% (vol:vol) Tween 20. After washes, membranes were incubated overnight at 4° C. with polyclonal rabbit anti-α-MSH IgG (1:1000, Peninsula Laboratories, San Carlos, Calif., USA), followed by washes and incubation with polyclonal swine anti-rabbit horseradish peroxidase-conjugated Igs (1:3000; Dako, Trappes, France). Immunoblots were revealed by the ECL detection system (GE Healthcare) and were scanned with ImageScanner II (GE Healthcare) previously calibrated by using a greyscale marker (Kodak) and digitalized with Labscan 6.00 software (GE Healthcare). The same procedure was performed after adsorption of rabbit anti-α-MSH IgG with $10^{-6}$M of α-MSH peptide (Bachem AG, Bubendorf, Switzerland) overnight at 4° C.

Protein Identification

The protein spots of interest were excised from CBB G-250-stained 2D gels using the Ettan Spot Picker (GE Healthcare), and automated in-gel digestion of proteins was performed on the Ettan Digester (GE Healthcare). Protein extracts were then resuspended in 10 µl of 5% (vol:vol) acetonitrile/0.1% (vol:vol) formic acid and then analyzed with a nano-LC1200 system coupled to a 6340 Ion Trap mass spectrometer equipped with a nanospray source and an HPLC-chip cube interface (Agilent Technologies, Courtaboeuf, France). In brief, peptides were enriched and desalted on a 40-n=1 RPC18 trap column and separated on a Zorbax (30-nm pore size, 5-µm particle size) C18 column (43 mm long×75 µm inner diameter; Agilent Technologies). A 9-min linear gradient (3-80% acetonitrile in 0.1% formic acid) at a flow rate of 400 nl·$min^{-1}$ was used, and the eluent was analyzed with an Ion Trap mass spectrometer. For protein identification, MS/MS peak lists were extracted and compared with the protein databases by using the MASCOT Daemon version 2.2.2 (Matrix Science) search engine. The searches were performed with the following specific parameters: enzyme specificity, trypsin; one missed cleavage permitted; no fixed modifications; variable modifications, methionine oxidation, cysteine carbamidomethylation, serine, tyrosine and threonine phosphorylation; monoisotopic; peptide charge, 2+ and 3+; mass tolerance for precursor ions, 1.5 Da; mass tolerance for fragmentations, 0.6 Da; ESI-TRAP as instrument; taxonomy, $E.\ coli$; National Center for Biotechnology Information (NCBI) database (NCBInr 20120531 (18280215 sequences, 6265275233 residues); Bethesda, Md., USA). Protein hits were automatically validated if they satisfied one of the following criteria: identification with at least two top-ranking peptides (bold and red) each with a MASCOT score of 454 (Po0.01), or at least two top-ranking peptides each with a MASCOT score of 447 (Po0.05). To evaluate false-positive rates, all the initial database searches were performed using the 'decoy' option of MASCOT. Results were considered relevant if the false-positive rate never exceeded 1%.

Protein Identification from OFFGEL

High-resolution $E.\ coli$ K12 protein separation into 24 fractions was done onto the 3100 OFFGEL fractionator using the OFFGEL pH3-10 kit (Agilent Technologies). Protein samples (400 µg) preparation and assembly of all parts of the OFFGEL systems were done according to the procedures described in the Agilent Quick start Guide. OFFGEL fractionation was performed using the standard program OG24PRO with maximum limited current parameters (8000 V, 50 µA and 200 mW) until 64 KVh was reached after 30 h. At the end of the experiment, all fractions were transferred into a 0.8-ml deep well (Thermo Fisher Scientific, Illkirch, France) and stored at −20° C. Nine protein-containing fractions recovered from the central part of the OFFGEL were studied by western blot using rabbit anti-α-MSH IgG (Peninsula Laboratories) followed by protein identification as described above.

Immunization and Behavior in Mice

All experimental protocols were conducted according to US National Institutes of Health guidelines and EU directives, and animal experiments were approved by the Institutional Ethical Committees. Two-month-old male C57Bl6 mice (Janvier Laboratories, L'Arbresle, France) were acclimated to the animal facility for 1 week with 12 h light-dark cycle, lights on at 0700 hours and were kept in standard mouse-holding cages (n=8) each. Mice were fed ad libitum with standard pelleted rodent chow (RM1 diet, SDS, UK) with drinking water always available and were manipulated daily by gentle holding and measuring body weight. During acclimatization, mice were distributed between four cages to obtain the similar mean body weight per mouse per cage. After 1 week of acclimatization, mice from each cage were assigned to one of four study group and received following treatments: (i) Group 1, ClpB immunization (n=8): ClpB protein (Delphi Genetics, Gosselies, Belgium) 50 µg per mouse in 200 µl of 1:1 (vol:vol) of PBS with Complete Freund's Adjuvant (Sigma, St Louis, Mo., USA), intraperitoneally (i.p.); (ii) Group 2, adjuvant injection controls (n=8): 200 µl of Complete Freund's Adjuvant in PBS (1:1 (vol:vol), i.p.); (iii) Group 3, PBS injection controls (n=8): 200 µl of PBS (i.p.); and (iv) Group 4, intact controls (n=8): received no injections, and then all mice were returned to their holding cages. Fifteen days later, mice were given a boost immunization and the following treatments: (i) Group 1 (n=8), ClpB protein (Delphi Genetics) 50 µg per mouse in 200 µl of 1:1 (vol:vol) of PBS with Incomplete Freund's Adjuvant (Sigma) i.p.; (ii) Group 2 (n=8): 200 µl of Incomplete Freund's Adjuvant in PBS (1:1 (vol:vol), i.p.); (iii) Group 3, (n=8): 200 µl of PBS (i.p.); and iv) Group 4, (n=8): received no injections. Next day after the boost, mice were placed individually into the BioDAQ mouse cages (Research Diets, Inc., New Brunswick, N.J., USA) each equipped with an automatic feeding monitor. Food (Serlab, Montataire France) and drinking water were available ad libitum and body weight was measured daily. After 3 days of acclimatization to the BioDAQ cages, mice received the following treatments: Groups 1, 2 and 3 (each n=8), that is, mice that have been immunized with ClpB, injected with adjuvants and with PBS, respectively, all received an acute injection of α-MSH peptide (Bachem AG), 100 µg·$kg^{-1}$ body weight in 100 µl of PBS (i.p.) at 1000 hours. The control mice (n=8) received PBS only (i.p.). Feeding data was continuously monitored and analyzed using the BioDAQ data viewer 2.3.07 (Research Diets). For the meal pattern analysis, the inter-meal interval was set at 300 s.

After the feeding study, mice were placed in individual mouse-holding cages with food and water available ad libitum, and were analyzed for locomotor activity and anxiety in 0-maze (Med Associate, Inc., St Albans, Vt., USA) tests performed during 2 consecutive days. Two hours after the 0-maze test, mice were killed by decapitation in a guillotine and trunk blood was collected into EDTA-containing tubes. Plasma was separated by centrifugation at 3500 r.p.m. (1.4 g) for 10 min at 4° C. and stored at −80° C. before assay.

Locomotor Activity and Anxiety Tests

After feeding study in the BioDAQ cages, mice were analyzed for locomotor activity using a Versamax Animal Activity Monitor (AccuScan Instruments, Inc., Columbus, Ohio, USA). Next day after the locomotor activity test, all mice were tested for their anxiety in an elevated O-maze. The elevated-O-maze is a variation of more commonly used elevated plusmaze pharmacologically validated for anxiety testing in rodents. The advantage of the O-maze is that it lacks the ambiguous central square of the traditional plusmaze. The O-maze consisted of a circular infrared platform (outer diameter 120 cm) elevated 80 cm above the floor, featuring two open and two closed segments made of gray plastic. The closed segments were enclosed by walls extending 20 cm above the surface of the maze and covered with a black infrared plexiglas lid. Each test started by placing the mouse into one of the two closed segments. The test lasted 5 min and was recorded using a video camera placed above the O-maze and the EthoVision video tracking software (Noldus IT, Wageningen, The Netherlands). Measurements of distance and time spent in the open and closed segments were analyzed. Between each mouse tests, the 0-maze was cleaned with 30% ethanol.

ClpB and α-MSH Autoantibody Assay

Plasma levels of auto-Abs reacting with ClpB, α-MSH and adrenocorticotropic hormone were measured using enzyme-linked immunosorbent assay according to a published protocol (Fetissov S O., Methods Biol Mol 2011). In brief, ClpB protein (Delphi Genetics), α-MSH or adrenocorticotropic hormone peptides (Bachem AG) were coated onto 96-well Maxisorp plates (Nunc, Rochester, N.Y., USA) using 100 µl and a concentration of 2 µg·ml$^{-1}$ in 100 mM NaHCO$_3$ buffer, pH 9.6, for 72 h at 4° C. Plates were washed (5 min for three times) in PBS with 0.05% Tween 200, pH 7.4, and then incubated overnight at 4° C. with 100 µl of mouse plasma diluted 1:200 in PBS to determine free auto-Ab levels or diluted 1:200 in dissociative 3M NaCl and 1.5M glycine buffer, pH 8.9, to determine total auto-Ab levels. The plates were washed (three times) and incubated with 100 µl of alkaline phosphatase (AP)-conjugated goat antimouse IgG (1:2000) or anti-mouse IgM (1:1000), all obtained from Jackson ImmunoResearch Laboratories, Inc. (West Grove, Pa., USA). Following washing (three times), 100 µl of p-nitrophenyl phosphate solution (Sigma) was added as AP substrate. After 40 min of incubation at room temperature, the reaction was stopped by adding 3 N NaOH. The optical density was determined at 405 nm using a microplate reader Metertech 960 (Metertech Inc., Taipei, Taiwan). Blank optical density values resulting from the reading of plates without addition of plasma samples were subtracted from the sample optical density values. Each determination was done in duplicate. The variation between duplicate values was inferior to 5%. Similar protocol was used to measure anti-ClpB IgG and IgM in human plasma (1:400) using corresponding anti-human IgG or IgM AP-conjugated antibodies (1:2000, Jackson ImmunoResearch Laboratories, Inc.).

Absorptions of ClpB Antibodies with α-MSH

Plasma samples of mice, diluted 1:200 in PBS, or humans, diluted 1:400 in PBS, were preincubated with 10$^{-6}$M α-MSH peptide (Bachem AG) overnight at 4° C. before adding the samples to 96-well Maxisorp plates (Nunc) coated with ClpB protein (Delphi Genetics). IgG and IgM antibodies reactive with ClpB were detected by enzyme-linked immunosorbent assay using corresponding anti-mouse or anti-human AP-conjugated antibodies (Jackson ImmunoResearch Laboratories, Inc.) as described above. Percentage of ClpB antibodies crossreactive with α-MSH were calculated relative to levels of anti-ClpB antibodies detected without absorption in each individual plasma sample equal 100%.

IgG Purification from Plasma

IgG purification and affinity assay were performed according to a published protocol (Legrand et al., Protoc Exch 2014, doi:10.1038/protex2014.004). Extraction of plasma globulins was done by plasma acidification and separation on C18 SEP column (Phoenix Pharmaceuticals, Burlingame, Calif., USA), then 500 µl of mouse plasma was mixed with 500 µl of buffer A (1% trifluoroacetic acid in water). The column was activated in 1 ml of buffer B (60% acetonitrile in 1% trifluoroacetic acid) by 3 min centrifugation with 700 r.p.m. and rinsed three times with 3 ml of buffer A. Diluted plasma (1:1 in buffer A) was added to the column and the effluent (1 ml) was saved (frozen at −20° C.) for further purification of IgG. Total IgG were purified from the effluents of mouse plasma samples using the Melon Gel Kit (Thermo Fisher Scientific, Rockford, Ill., USA). Plasma effluents diluted 1:4 in kit's purification buffer was added on washed melon gel deposited in a column. Column was spun 1 min at 6000 r.p.m., and the IgG containing effluent was saved and frozen at −20° C. before lyophilization. Lyophilized IgG were reconstituted in the HBS-EP buffer (GE Healthcare, Piscataway, N.J., USA). For the cyclic adenosine monophosphate (cAMP) experiment, IgG purified from eight mice of the ClpB and of the adjuvant control group were combined, respectively, into two pools that were divided in two parts. One part was used directly in cAMP assay and the other was further purified using affinity chromatography for α-MSH (Bachem AG) coated on activated UltraLink beads (Pierce, Rockford, Ill., USA). The α-MSH IgGdepleted IgG effluents were saved, lyophilized and diluted in PBS.

Affinity Kinetics Assay

Affinity kinetics of mouse IgG for ClpB and α-MSH was determined by a biospecific interaction analysis based on the surface plasmon resonance phenomenon on a BIAcore 1000 instrument (GE Healthcare). α-MSH (Bachem AG) or ClpB protein (Delphi Genetics) were diluted to 0.5 mg·ml$^{-1}$ in 10 mM sodium acetate buffer, pH 5.0 (GE Healthcare), and were covalently coupled on the sensor chips CM5 (GE Healthcare) by using the amine coupling kit (GE Healthcare). All measures were performed on the same α-MSH or ClpB-coated chips. For the affinity kinetic analysis, a multicycle method was run with five serial dilutions of each IgG sample: 3360, 1680, 840, 420 and 210 (nmol), including a duplicate of 840 nmol and a blank sample (HBS-EP buffer only). Each cycle included 2 min of analyte injection and 5 min of dissociation with flow speed 30 µl·min$^{-1}$ at 25° C.

Between injections of each sample, the binding surface was regenerated with 10 mM NaOH, resulting in the same baseline level of the sensorgram. The affinity kinetic data were analyzed using BiaEvaluation 4.1.1 program (GE Healthcare). For fitting kinetic data, the Langmuir's 1:1 model was used, and the sample values were corrected by subtracting the blank values.

In Vitro cAMP Assay

Stable cell line of human embryonic kidney-293 cells expressing human MC4R was generated using a lentiviral transduction technology and purchased from Amsbio (Oxon, UK). High expression of MC4R mRNA in transfected cells was validated by reverse transcription PCR in Amsbio and in our laboratory. The presence of the transgene in cells before each experiment was verified by the visualization at a fluorescence microscope of the green fluorescent protein, which gene was inserted in the same with MC4R lentivector but under a different promoter. The α-MSH peptide (Bachem AG) was diluted in the induction buffer: PBS, 500 µM IBMX, 100 µM RO 20-1724 (Sigma), 20 mM MgCl2 to the final concentrations of 2, 1, 750, 500, 250, 100, 75, 50 and 10 nM corresponding to the α-MSH doses of 0.6, 3, 4.5, 6, 15, 30, 45, 60 and 120 pmol, respectively, and also included one blank sample. After unfreezing, the cells were cultured in 250 ml tissue culture flasks (BD-Falcon, Beckton-Dickinson, Bedford, Mass., USA) in Dulbecco's modified Eagle medium 4.5 g·l$^{-1}$ glucose (Eurobio, Courtaboeuf, France) supplemented with (2 mM L-glutamine, 10% fetal calf serum, 0.1 mM nonessential amino acids and 1% penicillin-streptavidin) in humidified cell culture incubator at 37° C., 5% CO2 for 8-10 days. At the day of experiment, cultured MC4R human embryonic kidney-293 cells were treated with 0.25% trypsin-EDTA (Sigma-Aldrich) and cell pellets were resuspended in PBS to obtain 5000 cells per well (10 NI) in a nontreated bioluminescence white 96-microwell plate (Nunc, Roskilde, Denmark). The cAMP production was measured using the bioluminescent assay cAMP-Glo Max Assay kit (Promega, Madison, Wis., USA) according to the manufacturer's instructions. In brief, the cells were incubated for 15 min at room temperature with different concentrations of α-MSH peptide alone or α-MSH together with mouse IgG pools from ClpB-immunized or adjuvant control groups, and which were added to the cells just before α-MSH. Serial dilutions of cAMP standard (provided by the kit) were assayed on the same microplate. cAMP detection solution was added to each well, then the cells were homogenized by agitation and centrifuged 2 min at 1000 r.p.m. and then incubated for 20 min at 23° C. Kinase-Glo reagent substrate was added in each well and after 10 min of incubation at 23° C., the luminescence was read with a bioluminescence instrument (Safas Spectrometer, Monaco). Three tests for each dilution were performed in separate wells and were repeated at two separate days resulting in n=6 for each point of the cAMP activation curve when native IgG were used. After depletion of native IgG from anti-α-MSH IgG fraction, the same experiment was performed with each α-MSH concentration and IgG as described above.

E. Coli Gavage in Mice

One-month-old male C57BI6 mice (Janvier Laboratories) were acclimated to the animal facility for 1 week and maintained as described above. Mice were distributed into four groups (n=8 in each) as follows: (i) gavaged with 108 E. coli K12 bacteria; (ii) gavaged with 108 E. coli K12 bacteria deficient for ClpB; (iii) gavaged with LB medium only; and (iv) controls that did not receive any treatments. The ClpB mutant strain was generated in the Bernd Bukau's Laboratory (ZMBH, Heidelberg University, Heidelberg, Germany) and was kindly provided together with the corresponding wildtype (WT) E. coli bacteria by Dr Axel Mogk. Mice were placed individually into the BioDAQ cages (Research Diets) and intragastrically gavaged daily before the onset of dark phase for 21 days with 0.5 nil of LB medium with or without bacteria. During the last day of gavage, mice feces were collected and frozen. After gavage, mice were killed by decapitation and trunk blood was collected into EDTA-containing tubes. Plasma was separated by centrifugation at 3500 r.p.m. (1.4 g) for 10 min at 4° C. and stored at −80° C. before assay. Plasma levels of anti-ClpB and anti-α-MSH IgG and IgM were assayed as described above.

ClpB DNA Assay

DNA was extracted from the cultures of the WT and ClpB mutant strains, and was also purified from mice feces using the QIAampR DNA Stool Mini Kit (Qiagen, France). Bacteria were dissolved in water and boiled at 100° C. during 5 min, after 1 min of centrifugation at 11 000 r.p.m., the supernatant containing the DNA was stored at −20° C. Using the NCBI primer design tool (http://www.ncbi.nlm.nih.gov/tools/primer-blast/), we designed the following nucleotide primers that amplify 180-base pair DNA region coding for the ClpB protein fragment containing one identified α-MSH-like epitope (FIG. 1e), forward: 5'-GCAGCTCGAAGGCAAAACTA-3' (SEQ ID NO: 4) and reverse: 5'-ACCGCTTCGTTCTGACCAAT-3' (SED ID NO: 5) (Invitrogen Custom Primers, Cergy Pontoise, France). PCR was performed in a thermocycler with MicroAmp tubes (Eppendorf, Hambourg, Germany). The reaction was carried out in a 50-μl volume containing 25 μl of Go Taq Green Master Mix 2×(Promega), 1 μl (20 pmol) of each primer, 21 μl of bi-distilled water and 1 μl of bacterial DNA. PCR conditions were as follows: 3 min at 94° C. followed by 35 cycles at 94° C. for 30 s, 60° C. for 30 s and 72° C. for 1.5 min. PCR products were visualized on a 1% agarose gel (Sigma), with the expected size of 180 base pair and the specificity validated using ClpB mutant strain.

Plasma Concentrations of Bacterial ClpB Protein

Plasma concentrations of bacterial ClpB were measured using enzyme-linked immunosorbent assay (ELISA) according to the following protocol. Rabbit polyclonal anti-ClpB IgG, customly generated by Delphi Genetics (Gosselies, Belgium), were coated on to 96-well Maxisorp plates (Nunc, Rochester, N.Y.) using 100 μl and a concentration of 2 μg/ml in 100 mM $NaHCO_3$ buffer, pH 9.6 for 24 h at 4° C. Plates were washed (5 min×3) in phosphate-buffered saline (PBS) with 0.05% Tween 200, pH 7.4. The recombinant ClpB protein, customly generated by Delphi Genetics, as a standard, was serially diluted to 5, 10, 25, 50, 70, 100 and 150 pM in the sample buffer (PBS, sodium azide 0.02%, pH 7.4) and added to the wells in duplicates. The plasma samples from patients with eating disorders and healthy controls (1:25 in sample buffer) were added to the remaining wells in duplicates and the ClpB standards and plasma samples were incubated 2 h at room temperature (RT). Plates were washed (5 min×3) in PBS with 0.05% Tween 200, pH 7.4. Mouse monoclonal anti-ClpB IgG (1:500 in sample buffer), customly generated by Delphi Genetics and pre-screened for having no cross-reactivity with α-MSH, were added to the wells and incubated 90 min at room temperature. Plates were washed (5 min×3) in PBS with 0.05% Tween 200, pH 7.4. Goat anti-mouse IgG conjugated with alkaline phosphatase (1:2000 in sample buffer) from Jackson ImmunoResearch Laboratories, Inc. (West Grove, Pa.) were added to the wells and incubated for 90 min at RT. Plates were washed (5 min×3) in PBS with 0.05% Tween 200, pH 7.4 and then 100 μl of p-nitrophenyl phosphate solution (Sigma, St. Louis, Mo.) was added as alkaline phosphatase substrate. After 40 min of incubation at room temperature, the reaction was stopped by adding 3N NaOH. The optical density (OD) was determined at 405 nm using a microplate reader Metertech 960 (Metertech Inc., Taipei, Taiwan). Blank OD values resulting from the reading of plates without addition of plasma samples or ClpB protein standard dilutions were subtracted from the sample OD values. Plasma concentrations of ClpB was calculated based on the OD of the ClpB standard curve and was adjusted for the plasma dilution.

Statistical Analysis

Data were analyzed and the graphs were plotted using the GraphPad Prism 5.02 (GraphPad Software Inc., San Diego, Calif., USA). Normality was evaluated by the Kolmogorov-Smirnov test. Group differences were analyzed by the analysis of variance or the nonparametric Kruskal-Wallis test with the Tukey's or Dunn's post tests, respectively, according to the normality results. Body weight changes were analyzed with two-way repeated measurements analysis of variance and the Bonferroni post tests. Individual groups were compared using the Student's t-test or the Mann-Whitney test according to the normality results. Effects of absorptions of ClpB antibodies with α-MSH were analyzed using paired t-test. Pearson's or Spearman's correlation coefficients were calculated according to the normality of the variable. The cAMP production was analyzed using a nonlinear regression fit (log(α-MSH) vs normalized cAMP response), which equation was Y=100/(1+10(Log EC50–X)×HillSlope). Data are shown as mean±s.e.m., and for all test, P<0.05 was considered statistically significant.

Results

Proteomic Identification of Bacterial α-MSH Mimetics

To identify bacterial proteins with molecular mimicry to α-MSH, a research strategy based on proteomic technology was developed. Total protein was extracted from *E. coli* K12 cultures, the cytoplasmic fraction was resolved by 2D gel electrophoresis (FIG. 1a) and transferred to a polyvinylidene difluoride membrane. To increase the probability of detection of multiple α-MSH-like epitopes in bacterial proteins, the membrane was revealed with polyclonal anti-α-MSH IgG. 13 immunopositive protein spots were found (FIG. 1b), among which the spots 1-8 disappeared after preadsorption of antibodies with $10^{-6}$M α-MSH (FIG. 1c), confirming specific α-MSH-mimetic epitopes. Using mass spectrometry, protein spots 1,2,3 and 4, displaying the strongest α-MSH-like staining, were identified as isoforms of the heat-shock protein named ClpB, a 857-a.a. protein, 857 amino acid protein disaggregation chaperone or ClpB, MW 95526 (molecular weight: 95526 Da, accession number: NP_417083.1, SEQ ID NO: 1). Less intensely stained α-MSH-like spots 5-8 (with the highest MASCOT scores of 880, 877, 874 and 800, respectively) were isoforms of the 548-a.a. protein chaperonin GroEL, (molecular weight: 57293 Da; accession number: YP_001732912.1). An alternative strategy of *E. coli* protein separation was also used, using an OFFGEL fractionator followed by one-dimensional gel electrophoresis and western blot with anti-α-MSH IgG preadsorbed or not with α-MSH (data not shown). One band was specifically recognized by anti-α-MSH IgG and was found to contain the ClpB protein (with the highest MASCOT score of 1065). Based on these results, ClpB was selected as a target protein for further validation of its molecular mimicry with α-MSH. To analyze the amino-acid sequence homology between α-MSH and bacterial ClpB, both sequences were aligned in the Emboss Stretcher program that uses the Needleman-Wunsch algorithm (http://www.ebi.ac.uk/Tools/emboss/). The alignments revealed a site of the ClpB protein displaying discontinuous 5 a.a. sequence homology with α-MSH (FIG. 1d). This putative α-MSH-like epitope was located in an inter-helical loop of the ClpB protein structure indicating that it is exposed on the protein surface, that is, accessible to auto-Abs binding. Western blot of the recombinant ClpB protein revealed with anti-α-MSH IgG showed a 96-kDa band (FIG. 1e), confirming that the ClpB protein contains α-MSH-like epitope(s). These results show that the presence of at least five consecutive amino-acid sequence homology, according to the molecular mimicry concept is not an obligatory condition for bacterial proteins to be recognized by IgG crossreacting with a neuropeptide.

Immunization of Mice with COB

Figure 2B:
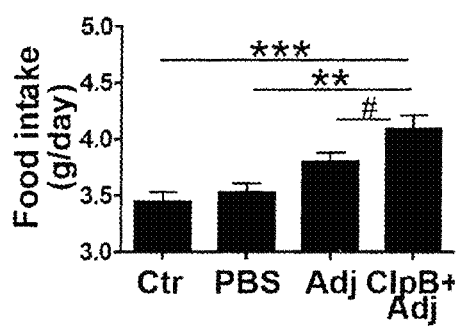
Figure 2C:
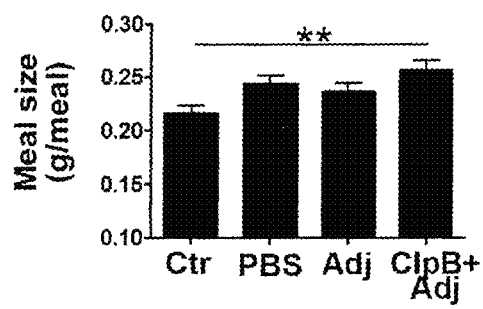
Figure 2D:
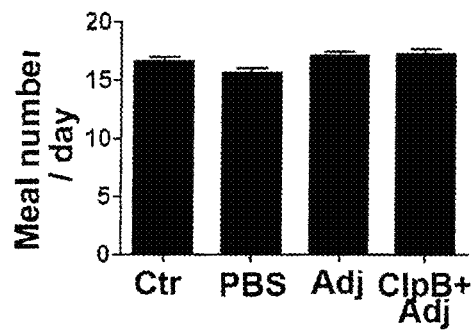
Figure 2E:
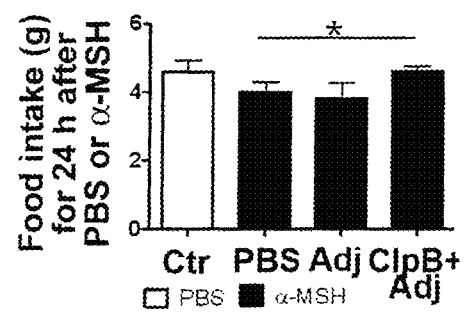
Figure 2F:
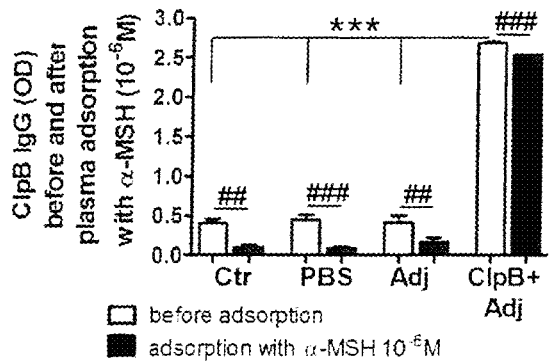
Figure 2G:
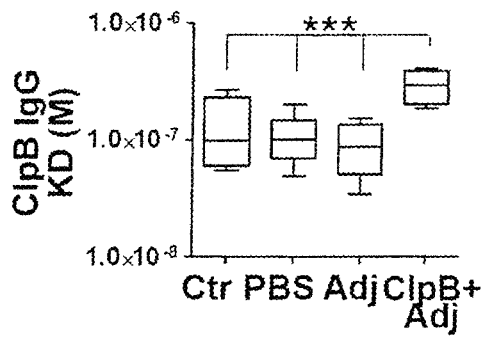
Figure 2H:
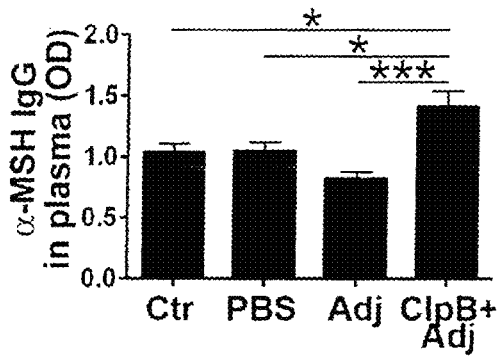
Figure 2I:
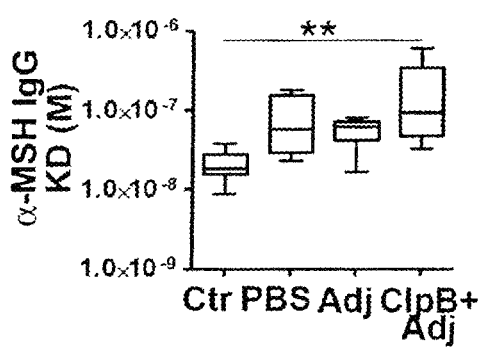

To investigate whether *E. coli* ClpB may induce auto-Abs crossreactive with α-MSH, influencing feeding and anxiety, mice were immunized with the recombinant bacterial ClpB protein. Mice that received ClpB together with adjuvant or adjuvant alone displayed lower body weight for a few days after injections (FIG. 2a). However, 4 weeks later, ClpB-immunized mice had higher body weight (+5%) vs controls (FIG. 2a). The mean daily food intake, as measured during the last 10 days of the experiment, was also higher (+13%) in ClpB-immunized mice as compared with other groups (FIG. 2b). The increase in food intake was owing to increased meal size (FIG. 2c), as meal number did not change (FIG. 2d), indicating that the ClpB immunization interfered with satiation rather than with hunger mechanisms. This is in agreement with the known role of α-MSH to induce satiation. To further validate the relevance of ClpB immunization to α-MSH anorexigenic effect, mice received i.p. injection of α-MSH. The following 24 h food intake and body weight were not affected in ClpB-immunized mice (FIG. 2e), indicating that they were not sensitive to the anorexigenic effect of administered α-MSH that was present in nonimmunized mice. After the feeding experiments, locomotor activity and anxiety related behavior in mice were studied in the open field and O-maze tests. The total locomotor activity and the time spent in the open vs border areas did not significantly differ between the study groups (data not shown). However, in the closed arms of the O-maze, the ClpB-immunized mice moved a shorter distance as compared with controls (data not shown) and spent less time as compared with all other groups (data not shown), indicating decreased anxiety. To confirm the efficiency of immunization, plasma levels of anti-ClpB IgG were assayed and their affinity measured. In ClpB immunized mice, a strong increase in anti-ClpB IgG levels (FIG. 2f) with lower affinities (FIG. 2g) were found, in agreement with recent IgG induction. Increased plasma levels of α-MSH-reactive IgG were also found in ClpB-immunized mice (FIG. 2h); these IgG were similarly characterized by lower affinities for α-MSH, as compared with controls (FIG. 2i). Adsorption of mouse plasma with α-MSH, significantly reduced plasma levels of anti-ClpB IgG, confirming that a fraction, but not all of the anti-ClpB IgG, were crossreactive with α-MSH (FIG. 2f). Plasma levels of α-MSH IgM auto-Abs did not significantly differ between the groups (data not shown). Whether ClpB immunization may induce auto-Abs crossreacting with the adrenocorticotropic hormone, a 39-a.a. peptide containing the α-MSH sequence was also analyzed. No significant differences in plasma adrenocorticotropic hormone-reactive IgG were found (data not shown), showing the selectivity of the conformational mimicry between ClpB and α-MSH.

Mouse IgG Effects on MC4R Signaling

Figure 2J:
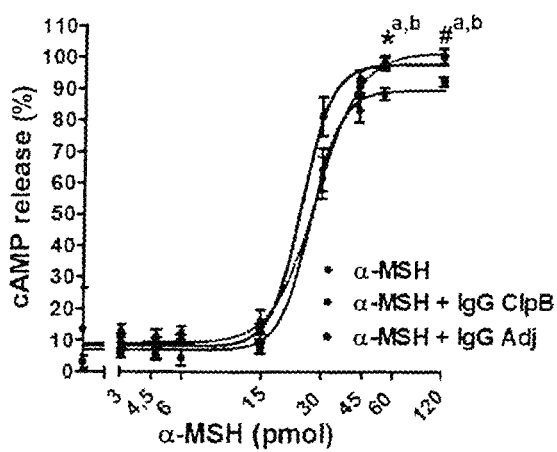
Figure 2K:
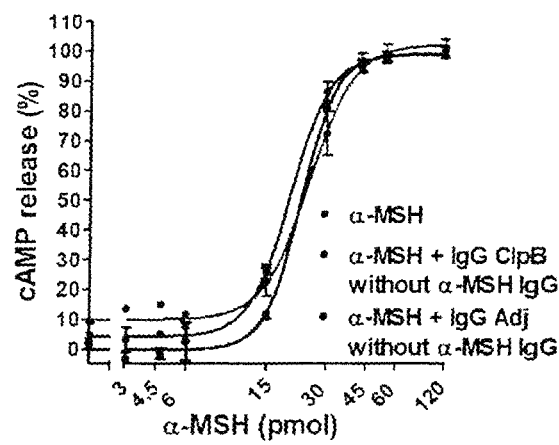

To determine the impact of ClpB immunization-induced α-MSH crossreactive IgG on MC4R signaling, their effects on α-MSH-induced cAMP production in MC4R-expressing cells were studied. cAMP concentrations were found to be lower when α-MSH was preincubated with IgG from ClpB-immunized mice, as compared with α-MSH alone or α-MSH preincubated with IgG from adjuvant injected mice, with a reduction of 8-10% at the two highest α-MSH concentrations (FIG. 2j). After depletion of α-MSH-reactive IgG from the pooled IgG, the remaining IgG from the ClpB immunized mice did not show any effect on α-MSH-induced cAMP release (FIG. 2k), indicating that anti-α-MSH crossreactive IgG in ClpB-immunized mice were responsible for lowering cAMP production in response to α-MSH. The reduction in MC4R activation and signaling may, hence, account for the increased food intake and decreased anxiety observed in ClpB-immunized mice.

Intragastric Delivery of *E. coli* in Mice

Figure 3A:
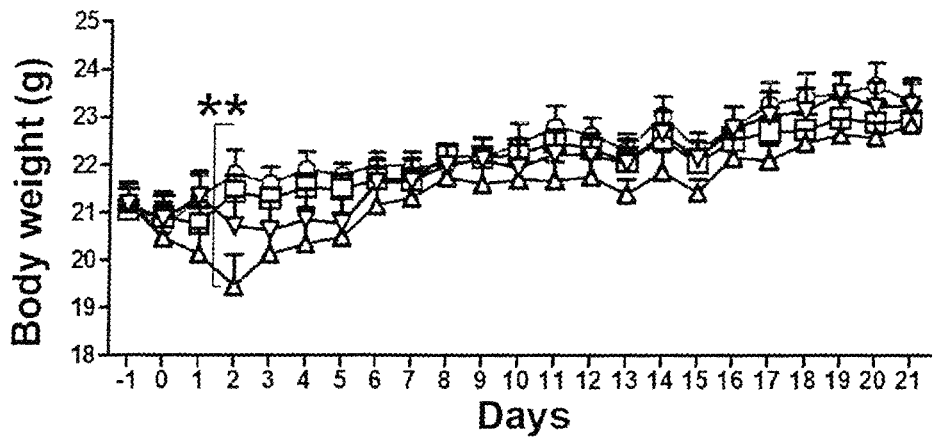
Figure 3B:
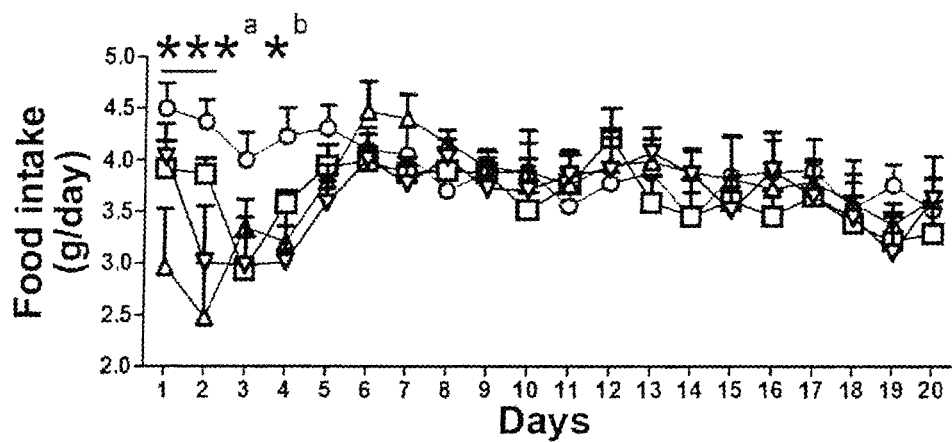
Figure 3C:
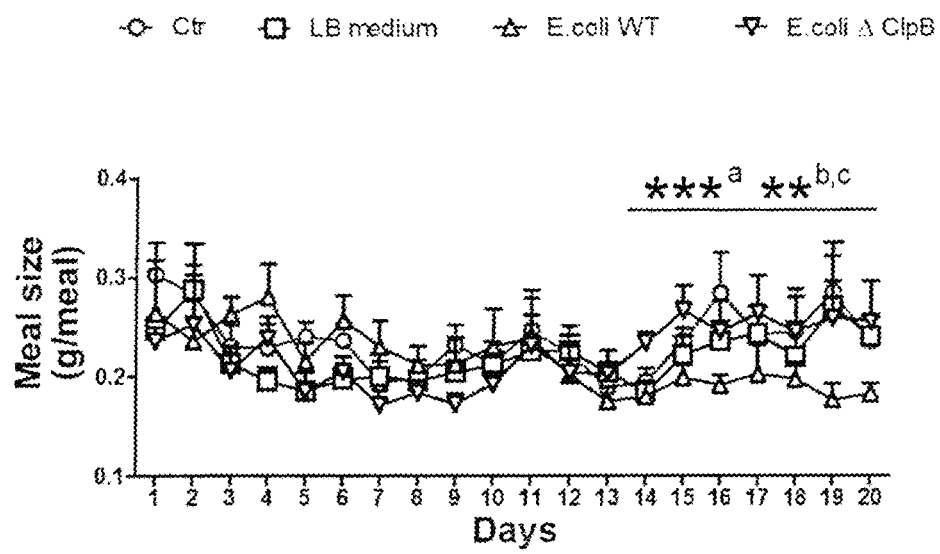
Figure 3D:
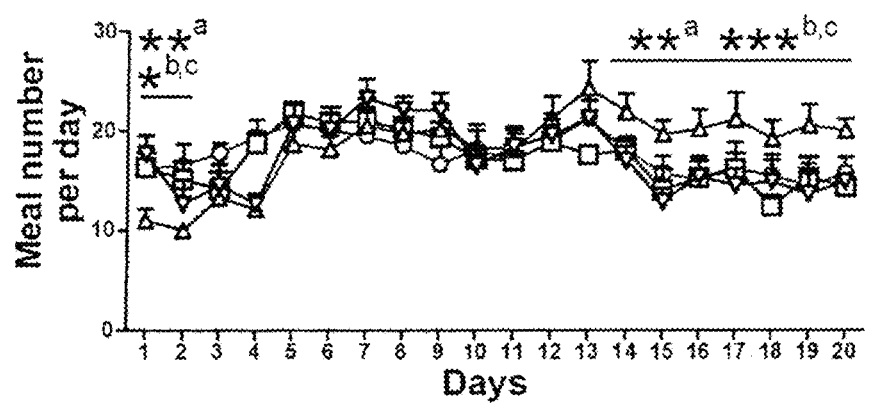
Figure 3E:
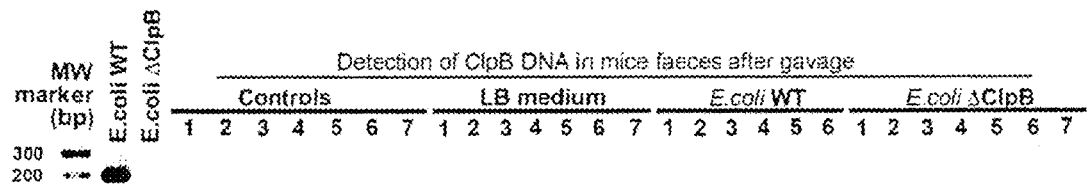
Figure 3F:
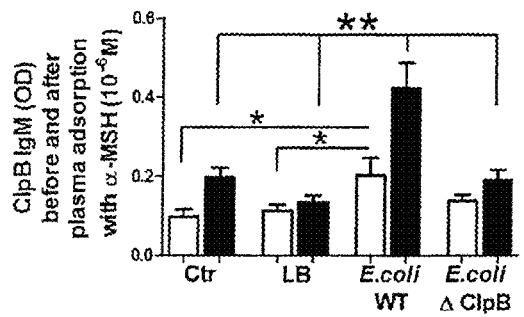
Figure 3G:
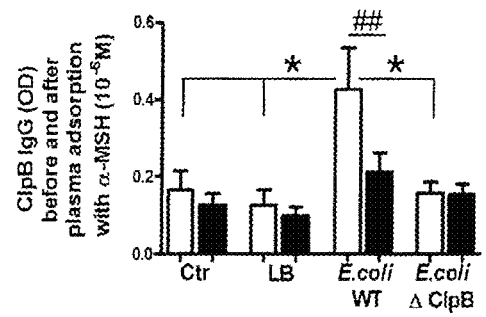
Figure 3H:
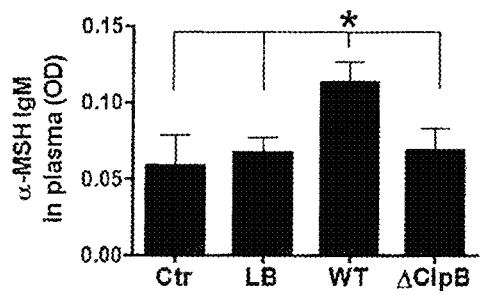
Figure 3I:
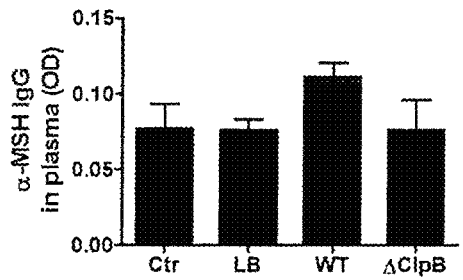
Figure 3J:
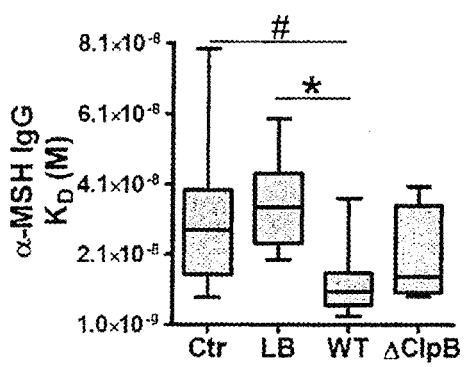

To test whether *E. coli* may induce immunogenic response against the ClpB protein, resulting in production of anti-ClpB auto-Abs crossreactive with α-MSH, WT and ΔClpB strains of *E. coli* K12 were given daily to mice by intragastric gavage during 3 weeks. Another group of mice was gavaged with the bacterial culture medium only, and the control group did not receive any treatment. The first days of gavage were accompanied by a decrease in body weight and food intake in mice receiving WT *E. coli*, which then gradually returned to control levels (FIGS. 3a and b). Again, during the last week of gavage, feeding pattern was affected in mice receiving E. coli WT showing a decrease in meal size but increase in meal number (FIGS. 3c and d). Remarkably, mice receiving ΔClpB E. coli did not significantly differ from controls in either body weight gain, food intake or feeding pattern at any time point. These data support specific involvement of bacterial ClpB in the host acute decrease of food intake as well as in the chronic regulation of feeding pattern following E. coli infection. Expectedly, ClpB DNA was more abundant in feces of mice receiving E. coli WT, although its low level was detected in some control mice (FIG. 3e). After 3 weeks of gavage, plasma levels of both anti-ClpB IgM and IgG were elevated in mice that received E. coli WT as compared with controls and ΔClpB E. coli groups (FIGS. 3f and g). Adsorption of plasma with α-MSH reduced anti-ClpB IgG levels in E. coli WT-gavaged mice (FIG. 3g), indicating the presence of anti-ClpB IgG crossreactive with α-MSH. Interestingly, plasma levels of the IgM class of anti-ClpB auto-Abs were increased after adsorption with α-MSH, suggesting that α-MSH caused dissociation of α-MSH IgM immune complexes crossreactive with ClpB that were increased in E. coli WT-gavaged mice (FIG. 3f). Plasma levels of anti-α-MSH IgM were also increased by E. coli WT delivery as compared with all other groups (FIG. 3h), while anti-α-MSH reactive IgG were only slightly increased without reaching significance (FIG. 3i). Nevertheless, affinity kinetic analysis of α-MSH IgG revealed lower values of the dissociation equilibrium constants in E. coli-gavaged mice (FIG. 3j), without significant changes of the association or dissociation rates (data not shown). These changes, including increased levels of the IgM class of α-MSH reactive auto-Abs, might reflect an immune response towards ClpB as to a novel antigen. In fact, low or undetectable levels of ClpB DNA in feces of mice that did not receive E. coli WT indicates that ClpB-expressing microorganisms were not major gut commensals in the studied mice. Thus, in contrast to ClpB-immunized mice, which showed increased levels of low-affinity anti-α-MSH IgG associated with increased meal size and body weight gain, E. coli-gavaged mice showed increased production of both anti-α-MSH-reactive IgM and IgG with increased affinities associated with decreased meal size and body weight.

Anti-ClpB Antibodies in ED Patients

Figure 4A:
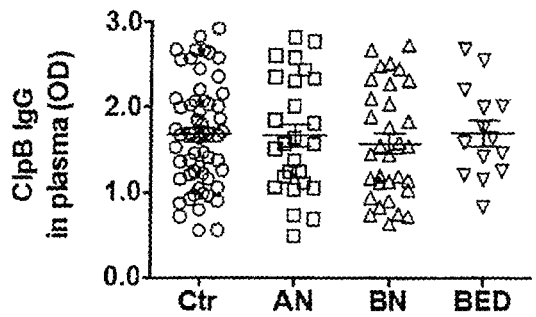
Figure 4B:
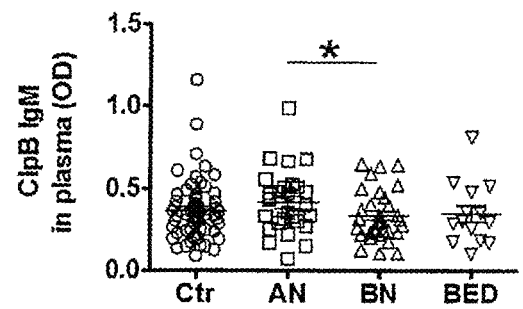
Figure 4C:
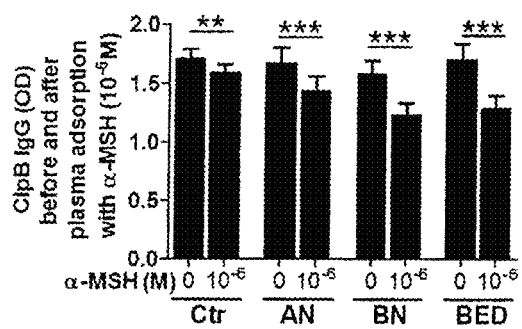
Figure 4D:
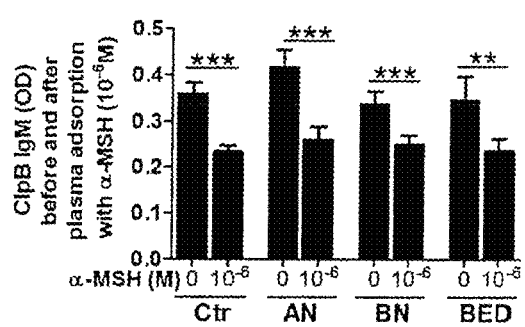
Figure 4E:
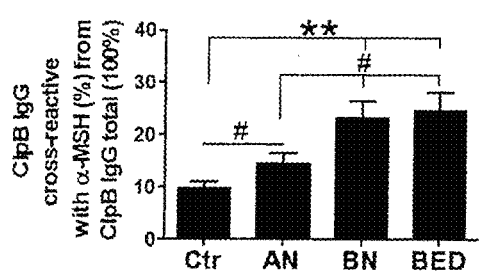
Figure 4F:
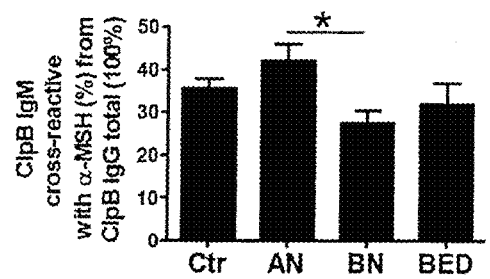

As the ability of the E. coli ClpB protein to stimulate production of α-MSH crossreactive auto-Abs was validated, the relevance of bacterial ClpB to ED was next determined by studying anti-ClpB antibodies in patients with AN, BN or BED. It was found that both anti-ClpB IgG and IgM were readily detectable in plasma of ED patients as well as healthy subjects with no significant differences of their mean levels (FIGS. 4a and b). However, there was high variability in all study groups, indicating a different individual history in encountering ClpB-like antigens. To verify whether human anti-ClpB antibodies similarly were crossreactive with α-MSH, plasma samples were adsorbed with $10^{-6}$M α-MSH, leading to significant reduction of anti-ClpB IgG and IgM detectable levels in all study groups (FIGS. 4c and d). Further, the relative levels of α-MSH crossreactive anti-ClpB IgG were increased in all three groups of ED patients, in particular BN and BED vs healthy controls (FIG. 4e). Elevated levels of α-MSH crossreactive anti-ClpB IgM were found in AN as compared with BN (FIG. 4f). To further determine the relevance of anti-ClpB IgG and IgM to ED, it was studied whether their plasma levels may correlate with behavioral traits in ED patients and controls measured by the EDI-2. It was found that in controls, ClpB IgG correlated inversely with the normal range of a few psychological traits, but in AN patients, ClpB IgG levels correlated positively with the core psychopathological traits such as body dissatisfaction and drive for thinness (Table 1). Moreover, in AN and BED patients, EDI-2 subscale scores correlated with ClpB IgM in the opposite way, being negative in AN but positive in BED (Table 1). However, in BED patients, ClpB IgM correlated negatively with age, suggesting that the highest anti-ClpB IgM levels were associated with the acute form of the disease. Remarkably, the correlations found in AN patients between ClpB IgG or IgM and drive for thinness or interpersonal distrust, respectively, resembled closely the correlations between the same psychological traits and α-MSH-reactive IgG or IgM found in a different group of AN patients in a previous study.

TABLE 1

Significant correlations between plasma levels of anti-ClpB IgG and IgM and psychological traits in eating disorder patients and controls (Contr.) assayed by the Eating Disorder Inventory-2.

| ClpB | | | | |
|---|---|---|---|---|
| ClpB IgG (Contr.) | Maturity fears $r = -0.31$ * | Impulse regulation $r = -0.26$ * | Social insecurity $r = -0.26$ * | |
| ClpB IgG (AN) | Body dissatisfaction $r = 0.4$ * | Drive for thinness $r = 0.35$ * | Perfectionism $r = 0.38$ * | |
| ClpB IgM (AN) | Ineffectiveness $r = -0.42$ * | Interpersonal distrust $r = -0.58$ ** | Social insecurity $r = -0.52$ ** | Anhedonia $r = -0.35$ * |
| ClpB IgM (BED) | Bulimia $r = 0.53$ * | Perfectionism $r = 0.6$ * | Age $r = -0.74$ ** | |

All Spearman's r * $p < 0.05$, ** $p < 0.01$, except Pearson's r * $p < 0.05$ for perfectionism. (n = 65 Contr., n = 27 AN, and n = 14 BED).

Plasma Concentrations of Bacterial ClpB Protein

ClpB protein was detected in plasma samples of all study subjects ranging from 10 pM to 180 pM with a mean level of about 30 pM in healthy controls. Mean plasma levels of ClpB were significantly elevated in all groups of patients with eating disorders, including AN, BN and BED (see FIG. 5). By applying the common criteria of a diagnostically-relevant changes of concentrations equal or exceeding 2 standard deviations, 21.7% of AN, 32% of BN and 25% of BED patients showed increased levels of plasma ClpB.

Conclusion

The results reveal a molecular link between ClpB expressing gut bacteria and the regulation of motivated behavior and emotion via production of ClpB protein and anti-ClpB antibodies crossreactive with α-MSH. It shows that specific alterations of gut microbiota may lead to behavioral and emotional abnormalities as observed in ED patients. The findings of increased levels of ClpB protein and anti-ClpB IgG crossreactive with α-MSH in ED patients and correlations of anti-ClpB antibodies with patient's psychopathological traits support the involvement of ClpB-expressing microorganisms in increased ClpB antibody production and establishment of abnormal feeding behavior and emotion.

In conclusion, the results identify ClpB as a protein responsible for the origin of auto-Abs crossreactive with α-MSH, associated with psychopathological traits in ED patients and, hence, that ClpB-expressing microorganisms as a novel specific target for diagnostics and treatment of ED.

Example 2

This example demonstrates the effect of ClpB-expressing bacteria on obese ob/ob mice.

Genetically obese ob/ob mice were acclimated to the animal facility for 1 week and maintained as described above. Mice were intragastrically gavaged with (i) $10^8$ *E. coli* K12 bacteria (expressing ClpB); (ii) $10^8$ *E. coli* K12 bacteria deficient for ClpB; both in Mueller-Hilton (MH) medium or with (iii) MH medium only, as a control. The ClpB mutant strain was generated in the Bernd Bukau's Laboratory (ZMBH, Heidelberg University, Heidelberg, Germany) and was kindly provided together with the corresponding wildtype (WT) *E. coli* bacteria by Dr. Axel Mogk. Mice were placed individually into the BioDAQ cages (Research Diets) and intragastrically gavaged daily for 21 days as indicated.

The inventors showed that gavage with *E. coli* K12 WT bacteria induced a 56% reduction in weight gain (FIGS. 6 and 7), a reduced fat mass/lean mass ratio (FIGS. 8 and 9) and a reduction of 20% of the total food intake (FIGS. 10 and 11), which was not observed with *E. coli* K12 bacteria deficient for ClpB.

Example 3

This example demonstrates the effect of other strains of bacteria expressing ClpB on obese ob/ob mice.

Genetically obese ob/ob mice were acclimated to the animal facility for 1 week and maintained as described above. Mice were intragastrically gavaged with (i) $10^8$ *E. coli* K12 bacteria (expressing ClpB); (ii) $10^8$ *E. coli* Niessle 1917 bacteria (expressing ClpB) (iii) $10^8$ *E. coli* Niessle 1917 bacteria (expressing COB) in lyophilized form; all in Mueller-Hilton (MH) medium or with (iv) MH medium only, as a control. Mice were intragastrically gavaged daily for 14 days as indicated.

The inventors showed that gavage with any strain of *E. coli* ClpB-expressing bacteria induced a reduction in weight gain (FIGS. 12 and 13) and a reduction in fat content (FIG. 14).

Example 4

This example demonstrates the effect of ClpB-expressing *Hafnia alvei* on obese ob/ob mice.

Genetically obese ob/ob mice were acclimated to the animal facility for 1 week and maintained as described above. Mice were intragastrically gavaged with (i) $10^8$ *Hafnia alvei* AF036 bacteria (expressing ClpB); (ii) $10^8$ *E. coli* K12 bacteria deficient for ClpB; (iii) $10^8$ *E. coli* Niessle 1917 bacteria (expressing ClpB); all in Mueller-Hilton (MH) medium or with (iv) MH medium only, as a control.

The inventors show that treatment with *Hafnia alvei* induced a significant decrease in body weight gain as compared to obese controls (FIG. 15). Moreover, the decrease in body weight gain was associated with a decrease of cumulative food intake (FIG. 16), and with a decrease of both fat and lean masses, without alteration of the lean/fat mass ratio (FIG. 17).

Example 5

This example demonstrates the effect of ClpB-expressing *Hafnia alvei* on high fat diet-induced obese mice.

One-month-old male C571316 mice (Janvier Laboratories) were induced with high fat/high carbs diet for 2 weeks. Mice were then intragastrically gavaged with (i) $10^8$ *Hafnia alvei* AF036 bacteria (expressing ClpB); (ii) $10^8$ *E. coli* K12 bacteria deficient for ClpB; both in Mueller-Hilton (MH) medium or with (iii) MH medium only, as a control. Mice were placed individually into the BioDAQ cages (Research Diets) and intragastrically gavaged daily for 21 days as indicated.

Induction of obesity by high fat diet was validated by measurement of mean body weight (FIG. 18A), fat mass (FIG. 18B) and lean mass (FIG. 18C) in a group induced and a group non-induced for obesity.

The inventors showed that gavage with any strain of *Hafnia alvei* ClpB-expressing bacteria induced a reduction in weight gain (FIG. 19) and a reduction in fat content (FIG. 20).

The invention claimed is:

1. A method of treating obesity, said method comprising orally administering a composition to a human or non-human mammal subject in need thereof; wherein said composition comprises an effective amount of one or more probiotic strains expressing the ClpB protein comprising the SEQ ID NO: 2 amino acid sequence and presenting 80 to 100% identity with the SEQ ID NO: 1 amino acid sequence;
   wherein the probiotic strains:
      constitutively express the ClpB protein,
         are subjected to stress conditions so that the expression of the ClpB protein is up-regulated, or
         are genetically engineered for expressing the ClpB protein, and
   wherein the effective amount decreases at least 10% the food intake compared to the food intake prior to the initiation of the treatment.

2. The method according to claim 1, wherein the one or more probiotic strains are overexpressing ClpB protein.

3. The method according to claim 1, wherein the one or more probiotic strains are gram-negative bacteria.

4. The method according to claim 1, wherein the one or more probiotic strains are non-pathogenic gram-negative bacteria.

5. The method according to claim 1, wherein the one or more probiotic strains are bacteria of the Enterobacteriaceae family.

6. The method according to claim 1, wherein the one or more probiotic strains are non-pathogenic bacteria of the Enterobacteriaceae family.

7. The method according to claim 1, wherein the one or more probiotic strains is non-pathogenic *Escherichia coli*.

8. The method according to claim 1, wherein the one or more probiotic strains is of the genus *Hafnia*.

9. The method according to claim 1, wherein the one or more probiotic strains is *Hafnia alvei*.

10. The method according to claim 1, wherein the one or more probiotic strains are genetically modified.

11. The method according to claim 1, wherein the one or more probiotic strains are administered at a dose between 1000 million and 10000 million UFC·day$^{-1}$.

12. The method according to claim 1, wherein the one or more probiotic strains are administered to the subject in the form of a pharmaceutical composition.

\* \* \* \* \*

UNITED STATES PATENT AND TRADEMARK OFFICE
CERTIFICATE OF CORRECTION

PATENT NO. : 10,729,770 B2
APPLICATION NO. : 16/032604
DATED : August 4, 2020
INVENTOR(S) : S Fetissov et al.

Page 1 of 1

It is certified that error appears in the above-identified patent and that said Letters Patent is hereby corrected as shown below:

On the Title Page

Item (72) Nicolas Lucas of Rouen, FRANCE should be added as an inventor.

Signed and Sealed this
Fourth Day of May, 2021

Drew Hirshfeld
*Performing the Functions and Duties of the*
*Under Secretary of Commerce for Intellectual Property and*
*Director of the United States Patent and Trademark Office*

SEQUENCE LISTING

```
<160> NUMBER OF SEQ ID NOS: 5

<210> SEQ ID NO 1
<211> LENGTH: 857
<212> TYPE: PRT
<213> ORGANISM: Escherichia coli

<400> SEQUENCE: 1

Met Arg Leu Asp Arg Leu Thr Asn Lys Phe Gln Leu Ala Leu Ala Asp
1               5                   10                  15

Ala Gln Ser Leu Ala Leu Gly His Asp Asn Gln Phe Ile Glu Pro Leu
            20                  25                  30

His Leu Met Ser Ala Leu Leu Asn Gln Glu Gly Gly Ser Val Ser Pro
        35                  40                  45
```

```
Leu Leu Thr Ser Ala Gly Ile Asn Ala Gly Gln Leu Arg Thr Asp Ile
     50                  55                  60

Asn Gln Ala Leu Asn Arg Leu Pro Gln Val Glu Gly Thr Gly Gly Asp
 65                  70                  75                  80

Val Gln Pro Ser Gln Asp Leu Val Arg Val Leu Asn Leu Cys Asp Lys
                 85                  90                  95

Leu Ala Gln Lys Arg Gly Asp Asn Phe Ile Ser Ser Glu Leu Phe Val
                100                 105                 110

Leu Ala Ala Leu Glu Ser Arg Gly Thr Leu Ala Asp Ile Leu Lys Ala
                115                 120                 125

Ala Gly Ala Thr Thr Ala Asn Ile Thr Gln Ala Ile Glu Gln Met Arg
130                 135                 140

Gly Gly Glu Ser Val Asn Asp Gln Gly Ala Glu Asp Gln Arg Gln Ala
145                 150                 155                 160

Leu Lys Lys Tyr Thr Ile Asp Leu Thr Glu Arg Ala Glu Gln Gly Lys
                165                 170                 175

Leu Asp Pro Val Ile Gly Arg Asp Glu Glu Ile Arg Arg Thr Ile Gln
                180                 185                 190

Val Leu Gln Arg Arg Thr Lys Asn Asn Pro Val Leu Ile Gly Glu Pro
                195                 200                 205

Gly Val Gly Lys Thr Ala Ile Val Glu Gly Leu Ala Gln Arg Ile Ile
210                 215                 220

Asn Gly Glu Val Pro Glu Gly Leu Lys Gly Arg Arg Val Leu Ala Leu
225                 230                 235                 240

Asp Met Gly Ala Leu Val Ala Gly Ala Lys Tyr Arg Gly Glu Phe Glu
                245                 250                 255

Glu Arg Leu Lys Gly Val Leu Asn Asp Leu Ala Lys Gln Glu Gly Asn
                260                 265                 270

Val Ile Leu Phe Ile Asp Glu Leu His Thr Met Val Gly Ala Gly Lys
                275                 280                 285

Ala Asp Gly Ala Met Asp Ala Gly Asn Met Leu Lys Pro Ala Leu Ala
290                 295                 300

Arg Gly Glu Leu His Cys Val Gly Ala Thr Thr Leu Asp Glu Tyr Arg
305                 310                 315                 320

Gln Tyr Ile Glu Lys Asp Ala Ala Leu Glu Arg Arg Phe Gln Lys Val
                325                 330                 335

Phe Val Ala Glu Pro Ser Val Glu Asp Thr Ile Ala Ile Leu Arg Gly
                340                 345                 350

Leu Lys Glu Arg Tyr Glu Leu His His Val Gln Ile Thr Asp Pro
                355                 360                 365

Ala Ile Val Ala Ala Thr Leu Ser His Arg Tyr Ile Ala Asp Arg
370                 375                 380

Gln Leu Pro Asp Lys Ala Ile Asp Leu Ile Asp Glu Ala Ala Ser Ser
385                 390                 395                 400

Ile Arg Met Gln Ile Asp Ser Lys Pro Glu Glu Leu Asp Arg Leu Asp
                405                 410                 415

Arg Arg Ile Ile Gln Leu Lys Leu Glu Gln Gln Ala Leu Met Lys Glu
                420                 425                 430

Ser Asp Glu Ala Ser Lys Lys Arg Leu Asp Met Leu Asn Glu Glu Leu
                435                 440                 445

Ser Asp Lys Glu Arg Gln Tyr Ser Glu Leu Glu Glu Trp Lys Ala
                450                 455                 460
```

-continued

```
Glu Lys Ala Ser Leu Ser Gly Thr Gln Thr Ile Lys Ala Glu Leu Glu
465                 470                 475                 480

Gln Ala Lys Ile Ala Ile Glu Gln Ala Arg Arg Val Gly Asp Leu Ala
            485                 490                 495

Arg Met Ser Glu Leu Gln Tyr Gly Lys Ile Pro Glu Leu Glu Lys Gln
        500                 505                 510

Leu Glu Ala Ala Thr Gln Leu Glu Gly Lys Thr Met Arg Leu Leu Arg
    515                 520                 525

Asn Lys Val Thr Asp Ala Glu Ile Ala Glu Val Leu Ala Arg Trp Thr
530                 535                 540

Gly Ile Pro Val Ser Arg Met Met Glu Ser Glu Arg Glu Lys Leu Leu
545                 550                 555                 560

Arg Met Glu Gln Glu Leu His His Arg Val Ile Gly Gln Asn Glu Ala
            565                 570                 575

Val Asp Ala Val Ser Asn Ala Ile Arg Arg Ser Arg Ala Gly Leu Ala
        580                 585                 590

Asp Pro Asn Arg Pro Ile Gly Ser Phe Leu Phe Leu Gly Pro Thr Gly
    595                 600                 605

Val Gly Lys Thr Glu Leu Cys Lys Ala Leu Ala Asn Phe Met Phe Asp
610                 615                 620

Ser Asp Glu Ala Met Val Arg Ile Asp Met Ser Glu Phe Met Glu Lys
625                 630                 635                 640

His Ser Val Ser Arg Leu Val Gly Ala Pro Pro Gly Tyr Val Gly Tyr
            645                 650                 655

Glu Glu Gly Gly Tyr Leu Thr Glu Ala Val Arg Arg Pro Tyr Ser
        660                 665                 670

Val Ile Leu Leu Asp Glu Val Glu Lys Ala His Pro Asp Val Phe Asn
    675                 680                 685

Ile Leu Leu Gln Val Leu Asp Asp Gly Arg Leu Thr Asp Gly Gln Gly
690                 695                 700

Arg Thr Val Asp Phe Arg Asn Thr Val Ile Met Thr Ser Asn Leu
705                 710                 715                 720

Gly Ser Asp Leu Ile Gln Glu Arg Phe Gly Glu Leu Asp Tyr Ala His
            725                 730                 735

Met Lys Glu Leu Val Leu Gly Val Val Ser His Asn Phe Arg Pro Glu
        740                 745                 750

Phe Ile Asn Arg Ile Asp Glu Val Val Phe His Pro Leu Gly Glu
    755                 760                 765

Gln His Ile Ala Ser Ile Ala Gln Ile Gln Leu Lys Arg Leu Tyr Lys
770                 775                 780

Arg Leu Glu Glu Arg Gly Tyr Glu Ile His Ile Ser Asp Glu Ala Leu
785                 790                 795                 800

Lys Leu Leu Ser Glu Asn Gly Tyr Asp Pro Val Tyr Gly Ala Arg Pro
            805                 810                 815

Leu Lys Arg Ala Ile Gln Gln Ile Glu Asn Pro Leu Ala Gln Gln
        820                 825                 830

Ile Leu Ser Gly Glu Leu Val Pro Gly Lys Val Ile Arg Leu Glu Val
    835                 840                 845

Asn Glu Asp Arg Ile Val Ala Val Gln
850                 855

<210> SEQ ID NO 2
<211> LENGTH: 7
<212> TYPE: PRT
```

```
<213> ORGANISM: Escherichia coli

<400> SEQUENCE: 2

Arg Trp Thr Gly Ile Pro Val
1               5

<210> SEQ ID NO 3
<211> LENGTH: 13
<212> TYPE: PRT
<213> ORGANISM: Homo sapiens

<400> SEQUENCE: 3

Ser Tyr Ser Met Glu His Phe Arg Trp Gly Lys Pro Val
1               5                   10

<210> SEQ ID NO 4
<211> LENGTH: 20
<212> TYPE: DNA
<213> ORGANISM: Artificial Sequence
<220> FEATURE:
<223> OTHER INFORMATION: primer

<400> SEQUENCE: 4
gcagctcgaa ggcaaaacta                                           20

<210> SEQ ID NO 5
<211> LENGTH: 20
<212> TYPE: DNA
<213> ORGANISM: Artificial Sequence
<220> FEATURE:
<223> OTHER INFORMATION: primer

<400> SEQUENCE: 5
accgcttcgt tctgaccaat                                           20
```